United States Patent [19]

Shimada et al.

[11] Patent Number: 5,159,087

[45] Date of Patent: Oct. 27, 1992

[54] AROMATIC DIOLEFINIC COMPOUNDS, AROMATIC DIETHYL COMPOUNDS AND ELECTROPHOTOGRAPHIC PHOTOCONDUCTORS COMPRISING ONE AROMATIC DIETHYL COMPOUND

[75] Inventors: Tomoyuki Shimada, Numazu; Masaomi Sasaki, Susono; Mitsuru Hashimoto, Numazu, all of Japan

[73] Assignee: Ricoh Company, Ltd., Tokyo, Japan

[21] Appl. No.: 642,686

[22] Filed: Jan. 17, 1991

Related U.S. Application Data

[60] Continuation-in-part of Ser. No. 394,765, Aug. 16, 1989, abandoned, which is a division of Ser. No. 171,422, Mar. 21, 1988, Pat. No. 4,886,846.

[30] Foreign Application Priority Data

| Mar. 28, 1987 | [JP] | Japan | 62-77105 |
| Apr. 21, 1987 | [JP] | Japan | 62-98393 |
| Apr. 21, 1987 | [JP] | Japan | 62-98394 |
| Jun. 9, 1987 | [JP] | Japan | 62-142178 |
| Oct. 20, 1987 | [JP] | Japan | 62-266068 |
| Oct. 27, 1987 | [JP] | Japan | 62-272783 |

[51] Int. Cl.$^5$ ............................................. C07D 209/82
[52] U.S. Cl. ..................................... 548/440; 430/79; 549/68; 564/307; 564/427; 564/429; 564/434
[58] Field of Search .......................... 548/440; 430/79

[56] References Cited

U.S. PATENT DOCUMENTS

| 4,451,548 | 5/1984 | Kinoshita | 430/79 |
| 4,521,605 | 6/1985 | Okazaki et al. | 430/79 |

FOREIGN PATENT DOCUMENTS

| 150853 | 9/1982 | Japan | 430/79 |
| 212455 | 12/1982 | Japan | 430/79 |
| 212456 | 12/1982 | Japan | 430/79 |
| 135953 | 7/1985 | Japan | 430/79 |

*Primary Examiner*—Richard L. Raymond
*Assistant Examiner*—Scott C. Rand
*Attorney, Agent, or Firm*—Oblon, Spivak, McClelland, Maier & Neustadt

[57] ABSTRACT

Aromatic diolefinic compounds including 1,4-divinyl-benzene derivatives, which are useful not only as organic photoconductive materials for electrophotography, but also as intermediates for producing diethyl aromatic compounds which are also useful as organic photoconductive materials for electrophotography, the aromatic diethyl compounds, an electrophotographic photoconductor containing any of the above aromatic diethyl compounds in a photosensitive layer thereof, and a charge transporting medium containing any of the aromatic diethyl compound are disclosed.

7 Claims, 12 Drawing Sheets

AROMATIC DIOLEFINIC COMPOUNDS, AROMATIC DIETHYL COMPOUNDS AND ELECTROPHOTOGRAPHIC PHOTOCONDUCTORS COMPRISING ONE AROMATIC DIETHYL COMPOUND

This application is a continuation-in-part (CIP) of application Ser. No. 07/394,765 having a U.S. filing date of Aug. 16, 1989, now abandoned, which is a divisional of application Ser. No. 07/171,422 having a U.S. filing date of Mar. 21, 1988, now U.S. Pat. No. 4,886,846.

BACKGROUND OF THE INVENTION

The present invention relates to aromatic diolefinic compounds including 1,4-divinylbenzene derivatives, aromatic diethyl compounds, and electrophotographic photoconductors containing any of the above aromatic compounds.

Conventionally, a variety of inorganic and organic electrophotographic photoconductors are known. As inorganic photoconductors for use in electrophotography, there are known types, in which the photoconductive material is, for instance, selenium, cadmium sulfide, and zinc oxide. In an electrophotographic process a photoconductor is first exposed to corona charges in the dark, so that the surface of the photoconductor is electrically charged uniformly. The thus uniformly charged photoconductor is then exposed to original light images and the portions exposed to the original light images selectively become electroconductive so that electric charges dissipate from the exposed portions of the photoconductor, whereby latent electrostatic images corresponding to the original light images are formed on the surface of the photoconductor. The latent electrostatic images are then developed by the so-called toner which comprises a colorant, such as a dye or a pigment, and a binder agent made, for instance, of a polymeric material; thus, visible developed images can be obtained on the photoconductor. It is necessary that photoconductors for use in electrophotography have at least the following fundamental properties: (1) chargeability to a predetermined potential in the dark; (2) minimum electric charge dissipation in the dark; and (3) quick dissipation of electric charges upon exposure to light.

While the above-mentioned inorganic electrophotographic. photoconductors have many advantages over other conventional electrophotographic photoconductors, at the same time they have several shortcomings from the viewpoint of practical use.

For instance, a selenium photoconductor, which is widely used at present and sufficiently meets the above-mentioned requirements (1) to (3), has the shortcoming that its production is difficult and, accordingly, its production cost is high. Further, it is difficult to work it into the form of a belt due to its poor flexibility, and it is so vulnerable to heat and mechanical shocks that it must be handled with the utmost care.

Cadmium sulfide photoconductors and zinc oxide photoconductors are. prepared by dispersing cadmium sulfide or zinc oxide in a binder resin. They can be produced inexpensively compared with selenium photoconductors and are also used commonly in practice. However, the cadmium sulfide and zinc oxide photoconductors are poor in surface smoothness, hardness, tensile strength and wear resistance. Therefore, they are not suitable as photoconductors for use in plain paper copiers in which the photoconductors are used in quick repetition.

Recently, organic electrophotographic photoconductors, which are said not to have such shortcomings of the inorganic electrophotographic photoconductors, have been proposed, and some of them are in fact employed for practical use. Representative examples of such organic electrophotographic photoconductors are an electrophotographic photoconductor comprising poly-N-vinylcarbazole and 2,4,7-trinitro-fluorene-9-one (U.S. Pat. No. 3,484,237), a photoconductor in which poly-N-vinylcarbazole is sensitized by a pyrylium salt type dyestuff (Japanese Patent Publication 48-25658), a photoconductor containing as the main component an organic pigment (Japanese Laid-Open Patent Application 47-37543), and a photoconductor containing as the main component an eutectic crystaline complex (Japanese Laid-Open Patent Application 47-10735).

Although the above-mentioned organic electrophotographic photoconductors have many advantages over other conventional electrophotographic photoconductors, they still have several shortcomings from the viewpoint of practical use, in particular, in terms of cost, production, durability and electrophotographic photosensitivity.

SUMMARY OF THE INVENTION

It is therefore an object of the present invention to provide novel aromatic diolefinic compounds including 1,4-divinylbenzene derivatives, which are useful not only as organic photoconductive materials for electrophotography, but also as intermediates for producing diethyl aromatic compounds which are also useful as organic photoconductive materials for electrophotography.

Another object of the present invention is to provide novel aromatic diethyl compounds which are useful as organic photoconductive materials for electrophotography.

A further object of the present invention is to provide electrophotographic photoconductors containing any of the above aromatic diethyl compounds, which has high photosensitivity and does not give rise to difficulties in producing the photoconductor, and which is comparatively inexpensive and excellent in durability.

The aromatic diolefinic compounds according to the present invention have the following general formula (I):

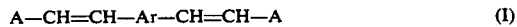

$$A-CH=CH-Ar-CH=CH-A \qquad (I)$$

wherein A represents an N-substituted carbazolyl group which may have a substituent such as an alkyl group having 1 to 5 carbon atoms and a phenyl group which may have a substituent such as an alkyl group having 1 to 5 carbon atoms and an alkoxyl group having 1 to 5 carbon atoms; or

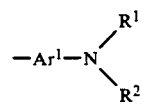

wherein $Ar^1$ represents an unsubstituted or substituted aromatic hydrocarbon group or a heterocyclic group, and $R^1$ and $R^2$ each represent an unsubstituted or substituted alkyl group, or an unsubstituted or substituted aryl group; and Ar represents an unsubstituted or substituted aromatic hydrocarbon group.

The above aromatic diolefinic compounds can be prepared by reacting a phosphorous compound of formula (Ia) with an aldehyde compound of formula (Ib) in the presence of a basic catalyst by Wittig reaction:

Y—CH₂—Ar—CH₂—Y     (Ia)

wherein Y represents a triphenylphosphonium group of the formula

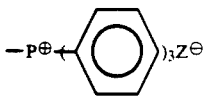

in which $Z^\ominus$ indicates a halogen ion such as Br, I and Cl; or a dialkylphosphonate group of the formula —PO(OR)₂ in which R represents an alkyl group having 1 to 5 carbon atoms and Ar represents an unsubstituted or substituted aromatic hydrocarbon group.

A—CHO     (Ib)

where A represents an N-substituted carbazolyl group which may have a substituent such as an alkyl group having 1 to 5 carbon atoms and a phenyl group which may have a substituent such as an alkyl group having 1 to 5 carbon atoms and an alkocysl group having 1 to 5 carbon atoms; or

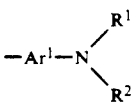

wherein Ar¹ represents an unsubstituted or substituted aromatic hydrocarbon group or a heterocyclic group, and R¹ and R² each represent an unsubstituted or substituted alkyl group, or an unsubstituted or substituted aryl group.

The 1,4-divinylbenzene derivatives according to the present invention have the following general formula (II):

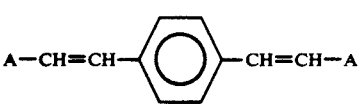     (II)

wherein A is the same as that defined in the above mentioned general formula (I).

The above 1,4-divinylbenzene derivatives can be prepared by reacting a phosphorous compound of formula (IIa) with the above mentioned aldehyde compound of formula (Ib) in the presence of a basic catalyst i the same manner as in the case of the aromatic diolefinic compounds of the above general formula (I):

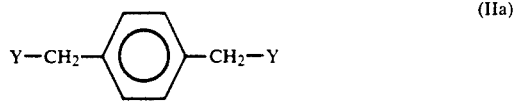     (IIa)

wherein Y is the same as that defined in the previously mentioned formula (Ia).

The aromatic diethyl compounds according to the present invention have the following general formula (III):

A—CH₂CH₂—Ar—CH₂CH₂—A     (III)

wherein A represents an N-substituted carbazolyl group which may have a substituent such as an alkyl group having 1 to 5 carbon atoms and a phenyl group which may have a substituent such as an alkyl group having 1 to 5 carbon atoms and an alkoxyl group having 1 to 5 carbon atoms; or

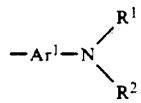

wherein Ar¹ represents an unsubstituted or substituted aromatic hydrocarbon group or a heterocyclic group, and R¹ and R² each represent an unsubstituted or substituted alkyl group, or an unsubstituted or substituted aryl group; and Ar represents an unsubstituted or substituted aromatic hydrocarbon group.

The above aromatic diethyl compounds can be prepared by reducing the aromatic olefinic compound of the previously mentioned formula (I), or by the so-called modified Wittig reaction between a phosphoric acid ester and an aldehyde.

The electrophotographic photoconductor according to the present invention comprises a photoconductive layer containing one aromatic diolefinic compound, or one aromatic diethyl compound, and an electroconductive support for supporting the photoconductive layer thereon.

DETAILED DESCRIPTION OF THE PREFERRED EMBODIMENTS

Figure 1:
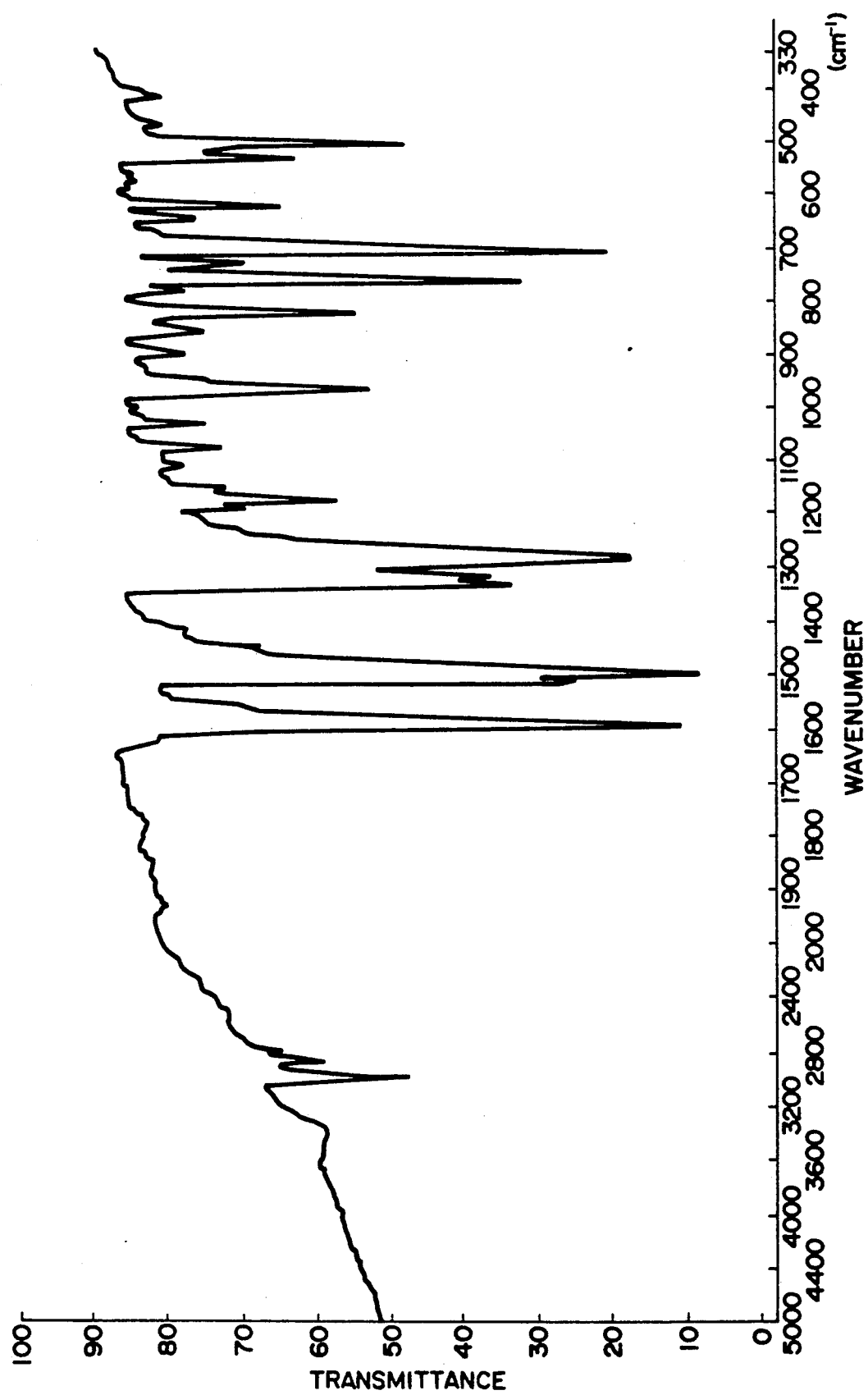
FIG. 1 is an infrared spectrum of aromatic diolefinic compound No. 1-1, 1,3-bis(4-N,N-diphenylaminostyryl)benzene, according to the present invention.

The aromatic diolefinic compounds according to the present invention have the following general formula (I):

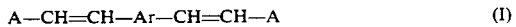  (I)

A—CH=CH—Ar—CH=CH—A wherein A represents an N-substituted carbazolyl group which may have a substituent such as an alkyl group having 1 to 5 carbon atoms and a phenyl group which may have a substituent such as an alkyl group having 1 to 5 carbon atoms and an alkoxyl group having 1 to 5 carbon atoms; or

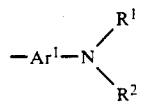

wherein $Ar^1$ represents an unsubstituted or substituted aromatic hydrocarbon group or a heterocyclic group, and $R^1$ and $R^2$ each represent an unsubstituted or substituted alkyl group, or an unsubstituted or substituted aryl group; and Ar represents an unsubstituted or substituted aromatic hydrocarbon group.

Examples of the aromatic hydrocarbon group represented by Ar or $Ar^1$ are a phenylene group, a naphthylene group, a biphenylene group, an anthranylene group, and an N-substituted carbazole group, each of which may have a substitutent, for example, an alkyl group having 1 to 5 carbon atoms, an alkoxyl group having 1 to 5 carbon atoms and halogen such as F, Cl and Br.

An example of the heterocyclic group represented by $Ar^1$ is a thienylene group.

Examples of the alkyl group represented by $R^1$ and $R^2$ are an alkyl group having 1 to 5 carbon atoms and a benzyl group.

An example of the aryl group represented by $R^1$ and $R^2$ is a phenyl group.

Examples of a substituent of the groups represented by $R^1$ and $R^2$ are an alkyl group having 1 to 5 carbon atoms, an alkoxyl group having 1 to 5 carbon atoms, halogen, a phenyl group, and a cyano group.

The above aromatic diolefinic compounds can be prepared by reacting one mole of a phosphorous compound of formula (Ia) with two moles of an aldehyde compound of formula (Ib) in the presence of a basic catalyst at temperatures ranging from room temperature to about 100° C.:

  (Ia)

Y—CH$_2$—Ar—CH$_2$—Y wherein Y represents a triphenylphosphonium group of the formula

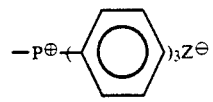

in which $Z^\ominus$ indicates a halogen ion such as Br, I and Cl; or a dialkylphosphonate group of the formula —PO(OR)$_2$ in which R represents an alkyl group having 1 to 5 carbon atoms and Ar represents an unsubstituted or substituted aromatic hydrocarbon group.

  (Ib)

A—CHO where A represents an N-substituted carbazolyl group which may have a substituent such as an alkyl group having 1 to 5 carbon atoms and a phenyl group which may have a substituent such as an alkyl group having 1 to 5 carbon atoms and an alkoxyl group having 1 to 5 carbon atoms; or

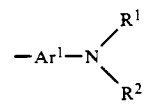

wherein $Ar^1$ represents an unsubstituted or substituted aromatic hydrocarbon group or a heterocyclic group, and $R^1$ and $R^2$ each represent an unsubstituted or substituted alkyl group, or an unsubstituted or substituted aryl group.

The 1,4-divinylbenzene derivatives according to the present invention have the following general formula (II):

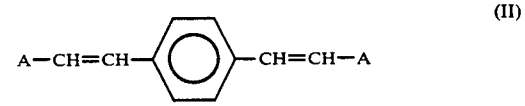  (II)

wherein A is the same as that defined in the above mentioned general formula (I).

The above 1,4-divinylbenzene derivatives can be prepared by reacting one mole of a phosphorous compound of formula (IIa) with two moles of the previously mentioned aldehyde compound of formula (Ib) in the same manner as in the case of the above aromatic diolefinic compounds of the formula (I).

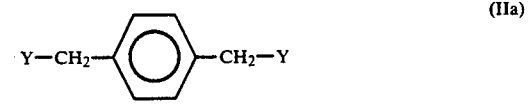  (IIa)

wherein Y represents a triphenylphosphonium group of the formula

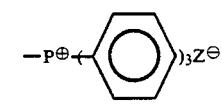

in which $Z^\ominus$ indicates a halogen ion such as Br, I and Cl; or a dialkylphosphonate group of the formula —PO(OR)$_2$ in which R represents an alkyl group having 1 to 5 carbon atoms and Ar represents an unsubstituted or substituted aromatic hydrocarbon group.

The phosphorous compounds of the formula (Ia) or formula (IIa) can be prepared without difficulty, for example, by heating a corresponding xylylene dihalide and a trialkyl phosphite or triphenylphosphine without any solvent or in a solvent, such as toluene, tetrahydrofuran or N,N-dimethylformamide. As the trialkyl phosphite, those having alkyl groups with 1 to 4 carbon atoms, in particular, those having methyl groups or ethyl groups are preferable for use in the present invention.

As mentioned above, any of the thus prepared phosphorous compounds of the formula (Ia) or (IIa) is allowed to react with the aldehyde compound of the formula (Ib) in the presence of a basic catalyst at temperatures ranging from room temperature to about 100° C.

As the basic catalyst for the above reaction, sodium hydroxide, potassium hydroxide, sodium amide, sodium hydride, and alcoholates such as sodium methylate and potassium tert-butoxide, can be employed.

As the reaction solvent, the following can be employed: methanol, ethanol, isopropanol, butanol, 2-methoxyethanol, 1,2-dimethoxyethane, bis(2-methoxyethyl)ether, dioxane, tetrahydrofuran, toluene, xylene, dimethyl sulfoxide, N,N-dimethylformamide, N-methylpyrrolidone and 1,3-dimethyl-2-imidazolidinone.

Of the above solvents, polar solvents, for example,

The reaction temperature for the above reaction can be set in a relatively wide range, depending upon (i) the stability of the solvent employed in the presence of the basic catalyst, (ii) the reactivities of the condensation components, that is, the phosphorous compounds of the formulae (Ia) and (IIa) and the aldehyde compound of the formula (Ib), and (iii) the properties of the basic catalyst which works as a condensation agent in this reaction. When, for example, a polar solvent is employed as the reaction solvent, the reaction temperature can be set in the range of room temperature to about 100° C., more preferably in the range of room temperature to about 80° C. However, if it is desired to shorten the reaction time or when a less reactive condensation agent is employed, the reaction temperature can be elevated beyond the aforementioned range.

Preparation of aromatic diolefinic compounds of the formula (I), A—CH=CH—Ar—CH=CH—A, will now be explained in detail with reference to the following examples:

SYNTHESIS EXAMPLE 1-1

Synthesis of 1,3-bis(4-N,N-diphenylaminostyryl)benzene 60 ml of N,N-dimethylformamide was added to a mixture of 3.78 g (10.0 mmol) of m-xylene-α,α'-diyl tetraethyldiphosphonate and 5.47 g (20.0 mmol) of 4-N,N-diphenylaminobenzaldehyde. To this mixture, 3.37 g (30 mmol) of potassium tert-butoxide was added over a period of 10 minutes, with stirring, with the temperature of the reaction mixture maintained at 27°~32° C. After the addition of the potassium tert-butoxide, the reaction mixture was stirred at room temperature for 5 hours and then diluted with 500 ml of water. The reaction mixture was extracted with toluene. The organic layer portion of the extract was washed with water and then dried with magnesium sulfate. The toluene was removed by evaporation from the organic layer portion, whereby a yellow oily material was obtained. The yellow oily material was chromatographed over a column of silica gel-toluene/n-hexane (volume ratio of 1/2), so that a yellow material was obtained. The thus obtained yellow material was recrystallized from a mixed solvent of ethanol and 2-butanone, whereby 3.70 g of 1,3-bis(4-N,N-diphenylaminostyryl)benzene, aromatic olefinic compound No. 1-1 according to the present invention, was obtained as light yellow crystals in a 60.0% yield. The melting point of the product was at 178.0°~180.0° C.

The result of the elemental analysis of the thus obtained 1,3-bis(4-N,N-diphenylaminostyryl)benzene were as follows:

|  | % C | % H | % N |
|---|---|---|---|
| Found | 89.61 | 5.73 | 4.28 |
| Calculated | 89.58 | 5.88 | 4.54 |

The above calculation was based on the formula for 1,3-bis(4-N,N-diphenylaminostyryl)benzene of $C_{46}H_{36}N_2$.

An infrared spectrum of the above synthesized 1,3-bis(4-N,N-diphenylaminostyryl)benzene, taken by use of a KBr pellet, is shown in FIG. 1, indicating a peak at 960 cm$^{-1}$ which is characteristic of the C—H out-of-plane deformation vibrations of a trans olefine.

SYNTHESIS EXAMPLES 1-2 THROUGH 1-9

Aromatic diolefinic compounds No. 1-2 to No. 1-9 as shown in the following Table 1 were obtained in the same manner as in Synthesis Example 1-1.

TABLE 1

A—CH=CH—Ar—CH=CH—A

| Synthesis Examples No. | Ar | A | m.p. (°C.) | Elemental Analysis Found (Calculated) % C | % H | % N |
|---|---|---|---|---|---|---|
| 1-2 | | 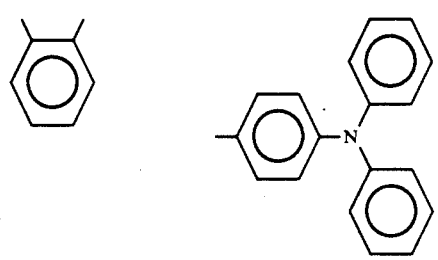 | 184.0~186.0 | 89.28 (89.56) | 5.86 (5.89) | 4.56 (4.54) |

TABLE 1-continued
A—CH=CH—Ar—CH=CH—A
| Synthesis Examples No. | Ar | A | m.p. (°C.) | Elemental Analysis Found (Calculated) | | |
|---|---|---|---|---|---|---|
| | | | | % C | % H | % N |
| 1-3 | 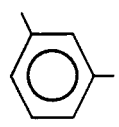 | 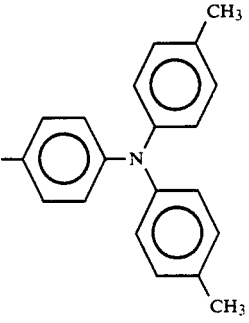 | 238.0~240.5 | 87.56 (89.23) | 6.92 (6.60) | 4.07 (4.17) |
| 1-4 | 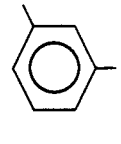 | 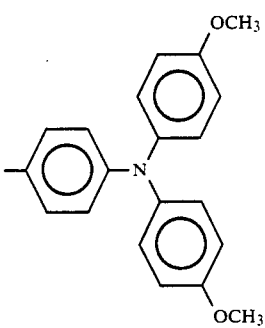 | 207.0~212.0 | 81.28 (81.49) | 5.91 (6.02) | 3.50 (3.80) |
| 1-5 | 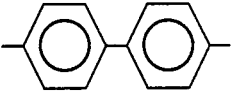 | 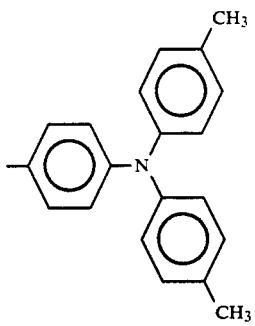 | 232.0~234.0 | 89.58 (89.79) | 6.67 (6.47) | 3.50 (3.74) |
| 1-6 | 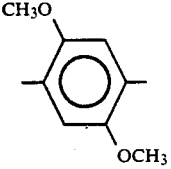 | 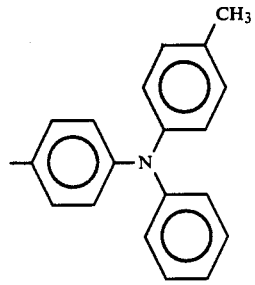 | 284.0~286.0 | 83.85 (83.98)* | 6.35 (6.42)* | 4.36 (4.48)* |

TABLE 1-continued

A—CH=CH—Ar—CH=CH—A

| Synthesis Examples No. | Ar | A | m.p. (°C.) | %C Found (Calculated) | %H | %N |
|---|---|---|---|---|---|---|
| 1-7 | 2,5-dimethoxyphenyl (CH$_3$O, OCH$_3$) | N,N-bis(4-methylphenyl)-4-aminophenyl | 285.5~290.0 | 85.10 (85.20) | 6.43 (6.61) | 3.79 (3.82) |
| 1-8 | 2,5-dimethoxyphenyl | N-(4-methoxyphenyl)-N-phenyl-4-aminophenyl | 160.0 | 81.28 (81.48) | 6.09 (6.03) | 3.92 (3.80) |
| 1-9 | 4-biphenylyl | 4-(N,N-diethylamino)phenyl | >320 | 85.72 (85.99) | 8.45 (8.44) | 5.49 (5.57) |

*Calculated as C$_{50}$H$_{44}$N$_2$O$_2$·½DMF

SYNTHESIS EXAMPLE 2-1

Synthesis of 1,4-bis[4-N,N-bis(4-methoxyphenyl)aminostyryl]benzene 70 ml of N,N-dimethylformamide was added to a mixture of 3.78 g (10.0 mmol) of p-xylene-α,α'-iyl tetraethyldiphosphonate and 6.67 g (20.0 mmol) of 4-N,N-bis(4-methoxyphenyl)aminobenzaldehyde. To this mixture, 3.37 g (30 mmol) of potassium tert-butoxide was added over a period of 1 hour, with stirring, with the temperature of the reaction mixture maintained at 21°~36° C. After the addition of the potassium tert-butoxide, the reaction mixture was stirred at room temperature for 5 hours and then diluted with 300 ml of water. The reaction mixture was neutralized, with stirring, with acetic acid. Crystals separated from the reaction mixture, which were filtered off, washed with water and methanol, whereby yellow crystals were obtained. The thus obtained yellow crystals were chromatographed over a column of silica gel-toluene and then recrystallized from a mixed solvent of ethanol and 2-butanone, whereby 4.00 g of 1,4-bis[4-N,N-bis(4-methoxyphenyl)aminostyryl]benzene, 1,4-divinylbenzene derivative No. 2-1 according to the present invention, was obtained as orange needle-like crystals in a 54.3% yield. The melting point of the product was at 177.5°~180.0° C.

The result of the elemental analysis of the thus obtained 1,4-bis[4-N,N-bis(4-methoxyphenyl)aminostyryl]benzene were as follows:

|  | % C | % H | % N |
|---|---|---|---|
| Found | 81.54 | 5.93 | 3.61 |
| Calculated | 81.49 | 6.02 | 3.80 |

The above calculation was based on the formula for 1,4-bis[4-N,N-bis(4-methoxyphenyl)aminostyryl]benzene of C$_{50}$H$_{44}$N$_2$O$_4$.

Figure 2:
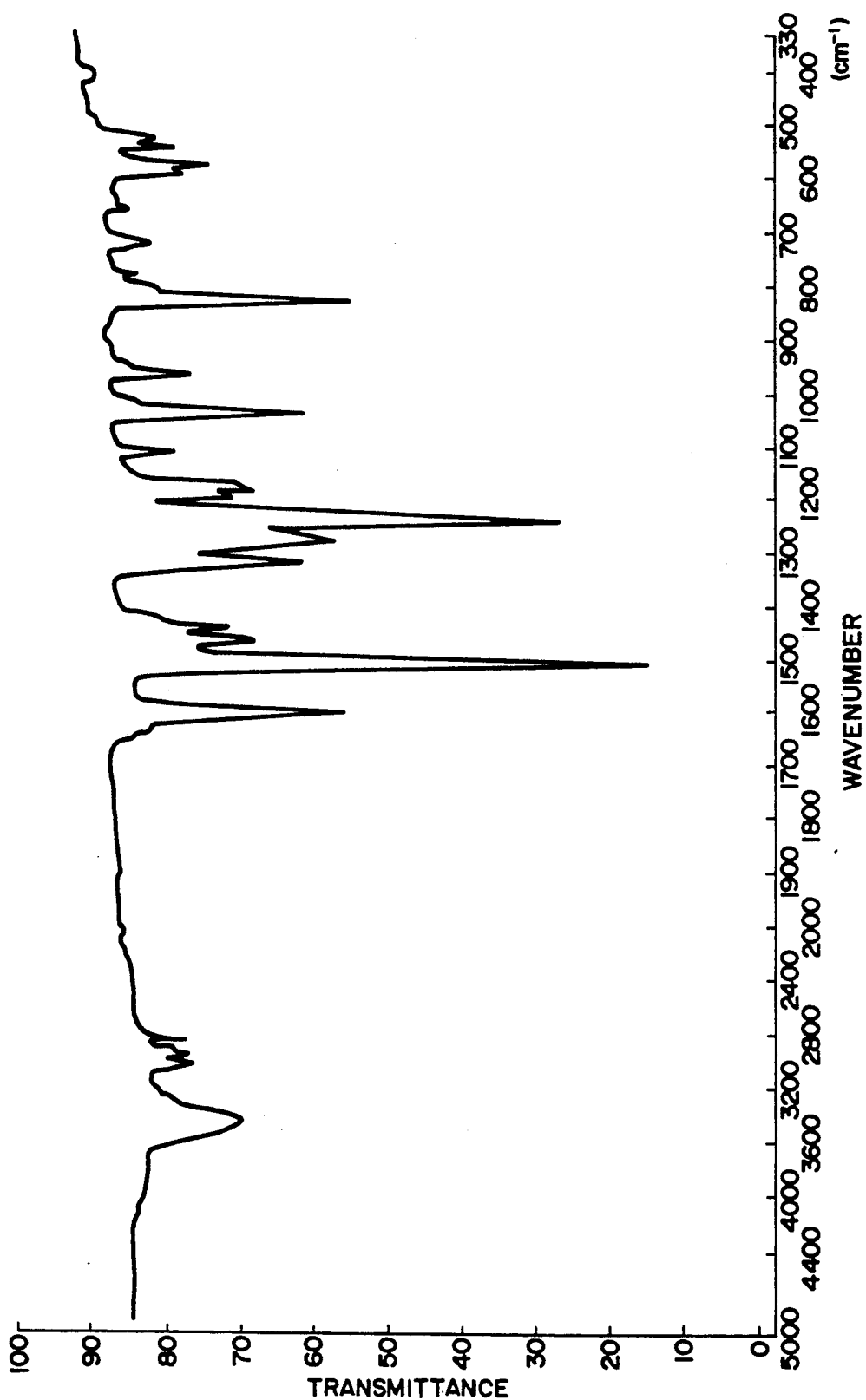
FIG. 2 is an infrared spectrum of 1,4-divinylbenzene derivative No. 2-1, 1,4-bis[4-N,N-bis(4-methoxyphenyl)aminostyryl]benzene, according to the present invention.
Figure 3:
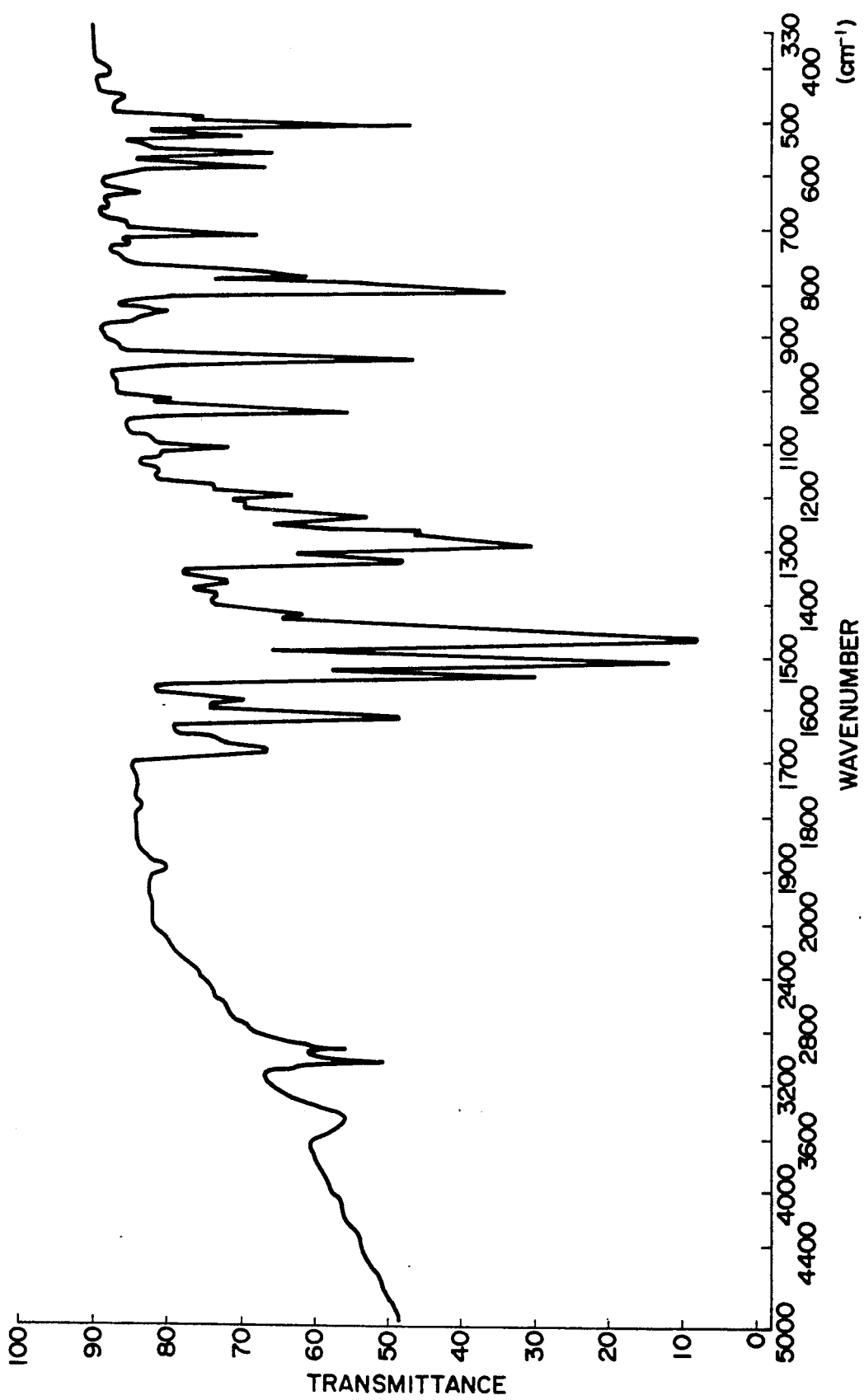
FIG. 3 is an infrared spectrum of 1,4-divinylbenzene derivative No. 2-13 in Table 2 according to the present invention.

An infrared spectrum of the above synthesized 1,4-bis[4-N,N-bis(4-methoxyphenyl)aminostyryl]benzene, taken by use of a KBr pellet, is shown in FIG. 2, indicating a peak at 963 cm$^{-1}$ which is characteristic of the C-H out-of-plane deformation vibrations of a trans olefine.

SYNTHESIS EXAMPLES 2-2 THROUGH 2-17

Synthesis Example 2-1 was repeated except that the 4-N,N-bis(4-methoxyphenyl)aminobenzaldehyde employed in Synthesis Example 2-1 was replaced, whereby 1,4-divinylbenzene derivatives No. 2-2 to No. 2-15 as shown in the following Table 2 were obtained.

TABLE 2
$$A-CH=CH-\phenyl-CH=CH-A$$
| Synthesis Examples No. | A | m.p. (°C.) | Elemental Analysis Found (Calculated) | | |
|---|---|---|---|---|---|
| | | | % C | % H | % N |
| 2-2 | 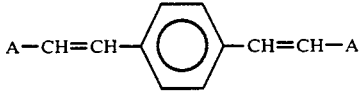 | >300 | 84.90 (84.74) | 7.63 (7.66) | 7.41 (7.60) |
| 2-3 | 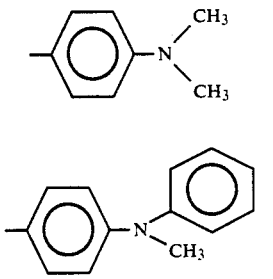 | 273.5~275.5 | 85.57 (87.76) | 6.56 (6.55) | 5.52 (5.69) |
| 2-4 | 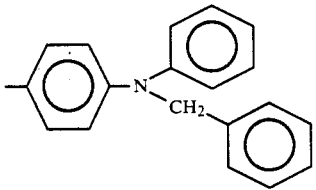 | 195.0~197.5 | 89.28 (89.40) | 6.20 (6.25) | 4.14 (4.35) |
| 2-5 | 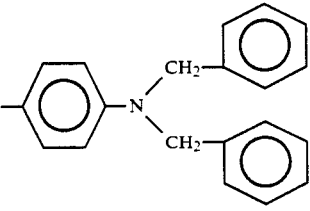 | 224.7~232.0 | 88.30 (88.19) (a) | 6.66 (6.67) | 4.48 (4.56) |
| 2-6 | 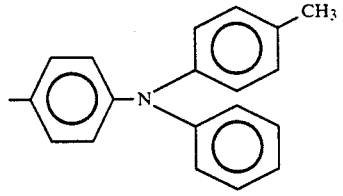 | 214.5~216.5 | 89.65 (89.40) | 6.14 (6.25) | 4.39 (4.35) |
| 2-7 | 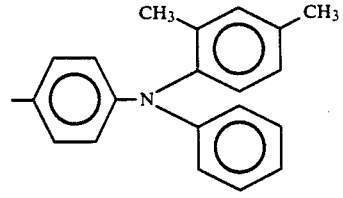 | 221.0~226.5 | 89.46 (89.25) | 6.69 (6.59) | 3.99 (4.16) |
| 2-8 | 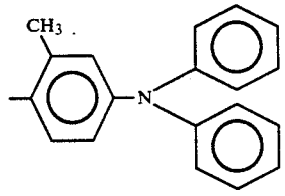 | 227.0~230.0 | 87.30 (87.25) (b) | 6.52 (6.44) | 4.79 (5.13) |

TABLE 2-continued $$A-CH=CH-\underset{}{\bigcirc}-CH=CH-A$$

| Synthesis Examples No. | A | m.p. (°C.) | Elemental Analysis Found (Calculated) | | |
|---|---|---|---|---|---|
| | | | % C | % H | % N |
| 2-9 | (p-tolyl)(phenyl)N–C₆H₄–OCH₃ | 172.0~175.3 | 85.02 (85.17) | 6.04 (5.96) | 4.01 (4.14) |
| 2-10 | (p-tolyl)(phenyl)N–C₆H₄–Cl | 227.0~229.0 | 80.70 (80.57) | 5.11 (5.01) | 4.00 (4.09) |
| 2-11 | (p-tolyl)(phenyl)N–C₆H₄–CN | 268.5~271.5 | 86.25 (86.45) | 5.08 (5.15) | 8.41 (8.40) |
| 2-12 | (naphthyl)(diphenyl)N | 262.0~264.5 | 90.11 (90.47) | 5.56 (5.62) | 3.91 (3.91) |
| 2-13 | thienyl–N(p-tolyl)₂ (CH₃) | 255.0~258.0 | 79.49 (79.57) (c) | 6.02 (6.03) | 4.69 (4.61) |
| 2-14 | N-ethylcarbazolyl | 270.0~273.0 | 88.30 (88.32) | 6.45 (6.25) | 5.50 (5.42) |

TABLE 2-continued

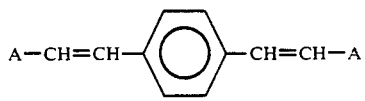

| Synthesis Examples No. | A | m.p. (°C.) | Elemental Analysis Found (Calculated) | | |
|---|---|---|---|---|---|
| | | | % C | % H | % N |
| 2-15 | 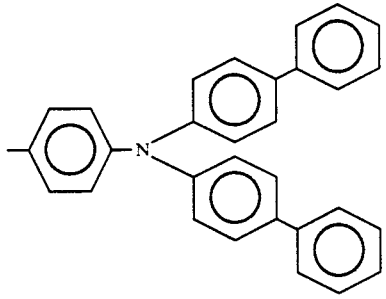 | >300 | 91.22 (91.27) | 5.72 (5.69) | 2.88 (3.04) |

(a) Calculated as $C_{50}H_{44}N_2 \cdot \frac{1}{4}DMF$
(b) Calculated as $C_{48}H_{40}N_2 \cdot \frac{1}{4}DMF$
(c) Calculated as $C_{46}H_{40}N_2S_2 \cdot \frac{1}{4}DMF$ As mentioned previously, the above aromatic diethyl compounds can be prepared by reducing the aromatic olefinic compound of the previously mentioned formula (I).

In the above reduction, catalysts such as metals, metal salts, metal hydrides and catalysts for hydrogenation in general use may be employed. Of these catalysts, catalysts for hydrogenation are most practical and convenient for use.

Examples of such catalysts for hydrogenation are platinum catalysts, paradium catalysts, rhodium catalysts, nickel catalysts, cobalt catalysts, and Ziegler catalysts. It is preferable that the amount of such a catalyst be in the range of 5~20 wt. % of the olefine compound to be reduced.

Preferable solvents for use in this reduction reaction are, for example, ethanol, methanol, dioxane, n-hexane, tetrahydrofuran, ethyl acetate, N,N-dimethylformamide, toluene, and benenzene. Of these solvents, dioxane, tetrahydrofuran, and N,N-dimethylformamide are most preferable for use in view of the solubility of the olefine compound in the solvents.

The reaction temperature and the pressure of hydrogen may be chosen from a wide range, depending upon the reducing power of the employed catalyst and other conditions for reduction. However, it is preferable that the reduction be performed at room temperature and at atmospheric pressure in view of the safety and suppression of side reactions during the reduction reaction.

SYNTHESIS EXAMPLE 3-1

Synthesis of 1,4-bis[2-(4-N,N-diphenylaminophenyl)ethyl]benzene 2.50 g of 1,4-bis(4-N,N-diphenylaminostyryl)benzene was dissolved in 50 ml of tetrahydrofuran. To this solution, 0.25 g of a 5% paradium-carbon was added and the 1,4-bis(4-N,N-diphenylaminostyryl)benzene was hydrogenated with a hydrogen pressure of 1 atm at 19° C. in a shaker hydrogenation apparatus. After the hydrogenation, the reaction mixture was filtered together with sellaite to obatin a filtrate. The filtrate was distilled under reduced pressure to remove tetrahydrofuran therefrom, so that white crystals were obtained. The white crystals were chromatographed over a column of silca gel-toluene, and then recrystallized from a mixed solvent of ethanol and ethyl acetate, whereby 2.18 g of 1,4-bis[2-(4-N,N-diphenylaminophenyl)ethyl]benzene, aromatic diethyl compound No. 3-1 according to the present invention, was obtained in the form of white needle-like crystals in a 86.5% yield. The melting point of the product was at 162.5°~163.5° C.

The result of the elemental analysis of the thus obtained 1,4-bis[2-(4-N,N-diphenylaminophenyl)ethyl]benzene were as follows:

| | % C | % H | % N |
|---|---|---|---|
| Found | 88.95 | 6.64 | 4.30 |
| Calculated | 88.99 | 6.50 | 4.51 |

The above calculation was based on the formula for 1,4-bis[2-(4-N,N-diphenylaminophenyl)ethyl]benzene of $C_{46}H_{40}N_2$.

Figure 4:
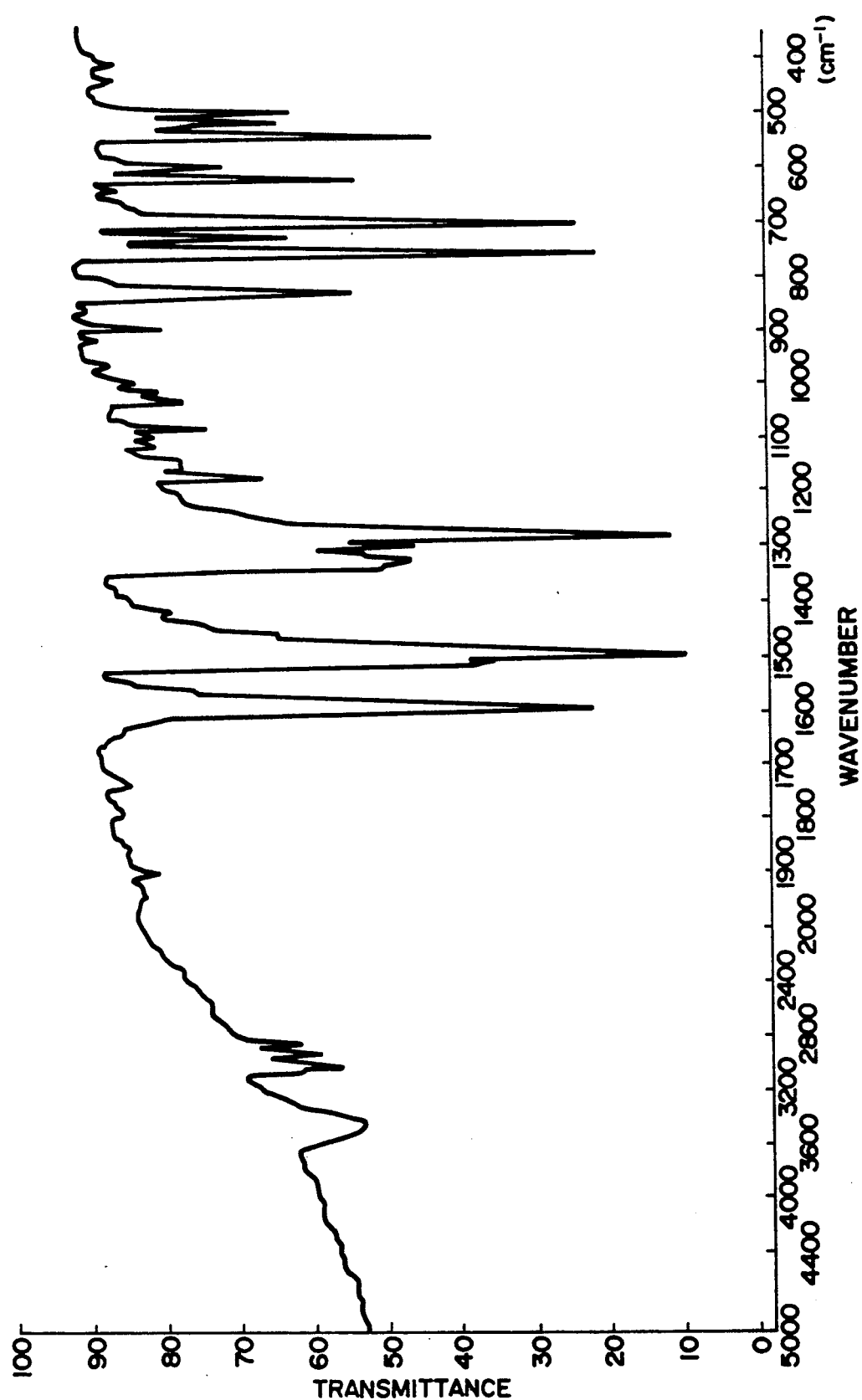
FIG. 4 is an infrared spectrum of aromatic diethyl compound No. 3-1, 1,4-bis[2-(4-N,N-diphenylaminophenyl) ethyl]benzene, according to the present invention.
Figure 5:
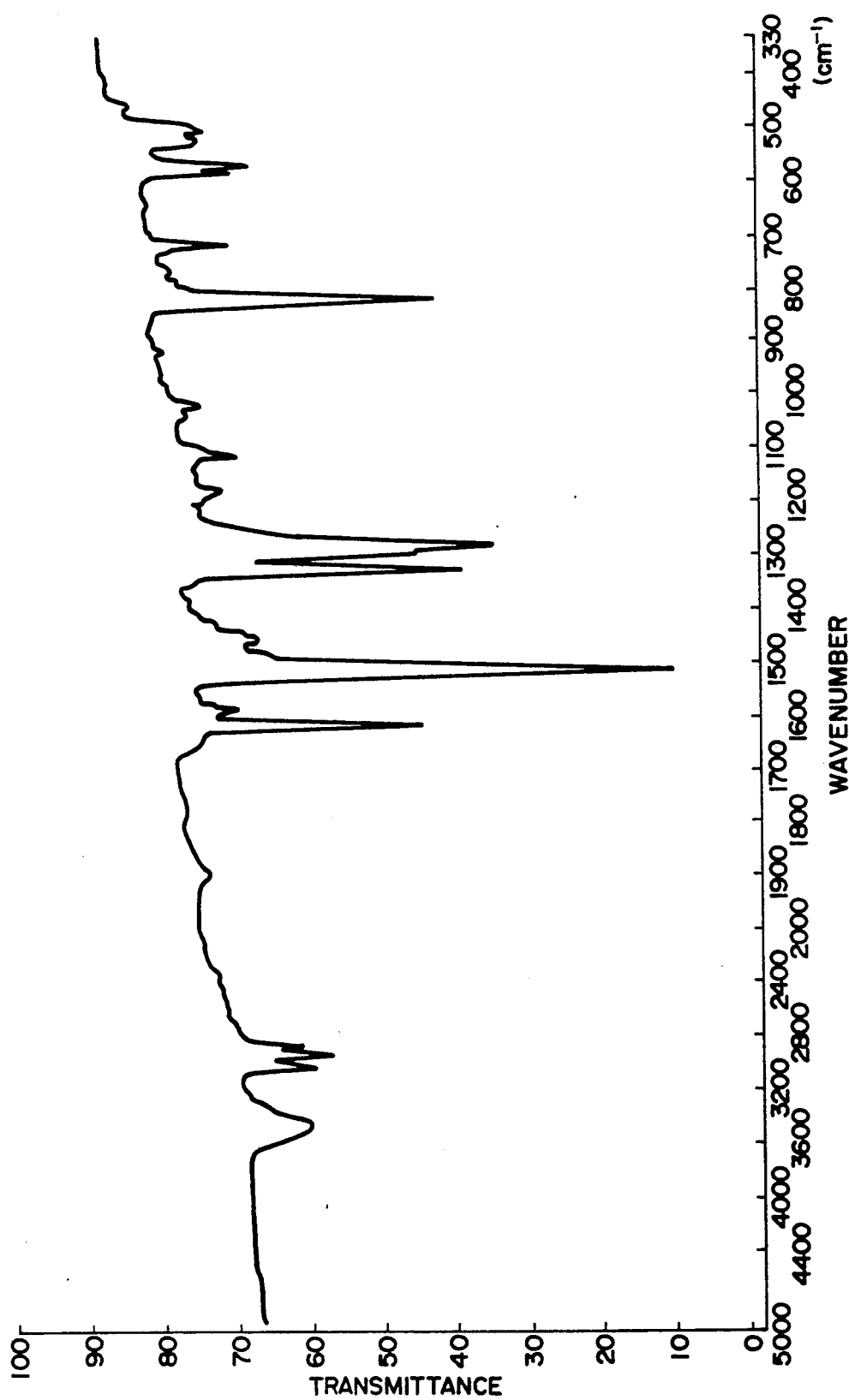
FIG. 5 is an infrared spectrum of aromatic diethyl compound No. 3-7 according to the present invention.
Figure 6:
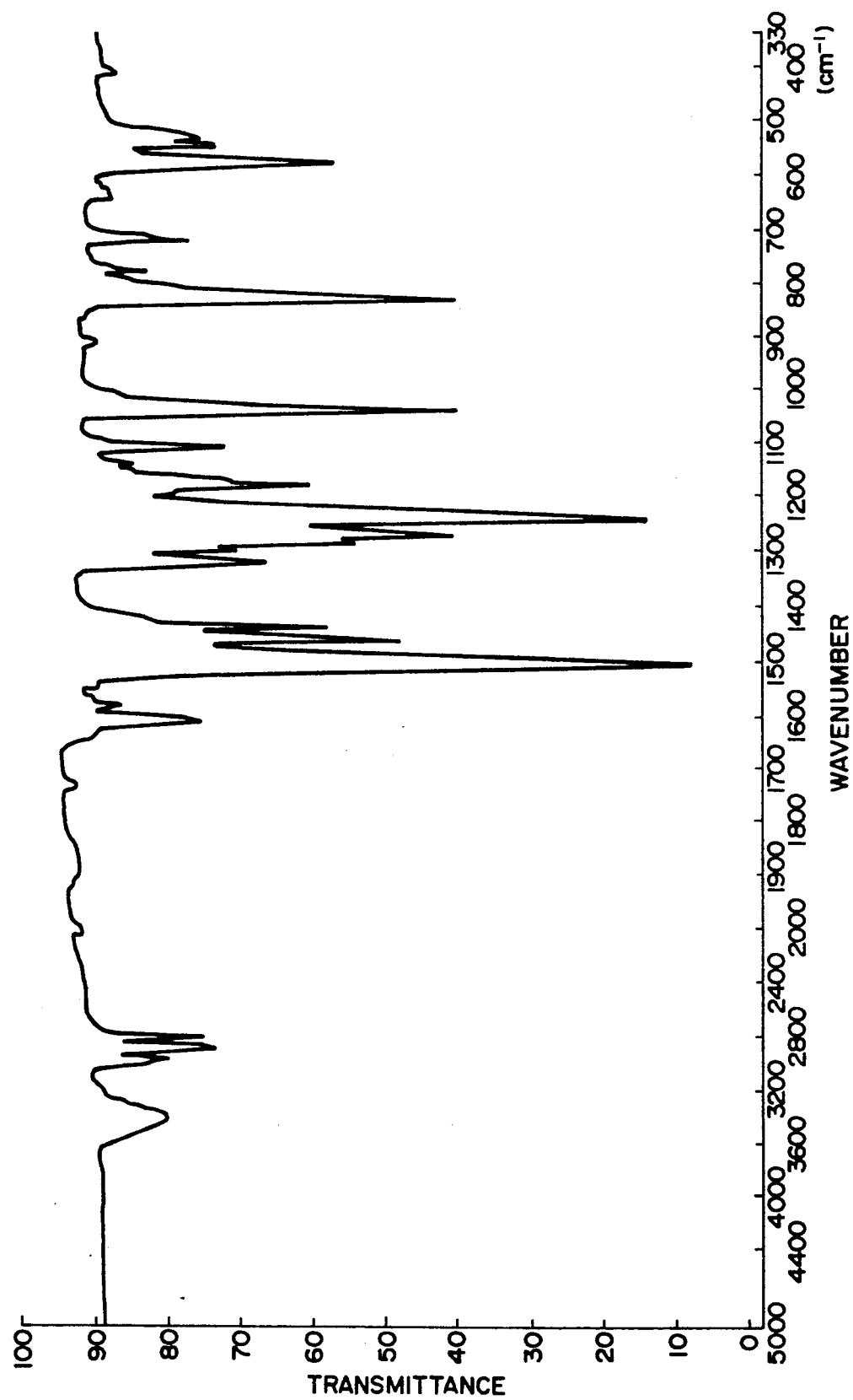
FIG. 6 is an infrared spectrum of aromatic diethyl compound No. 3-11 according to the present invention.
Figure 7:
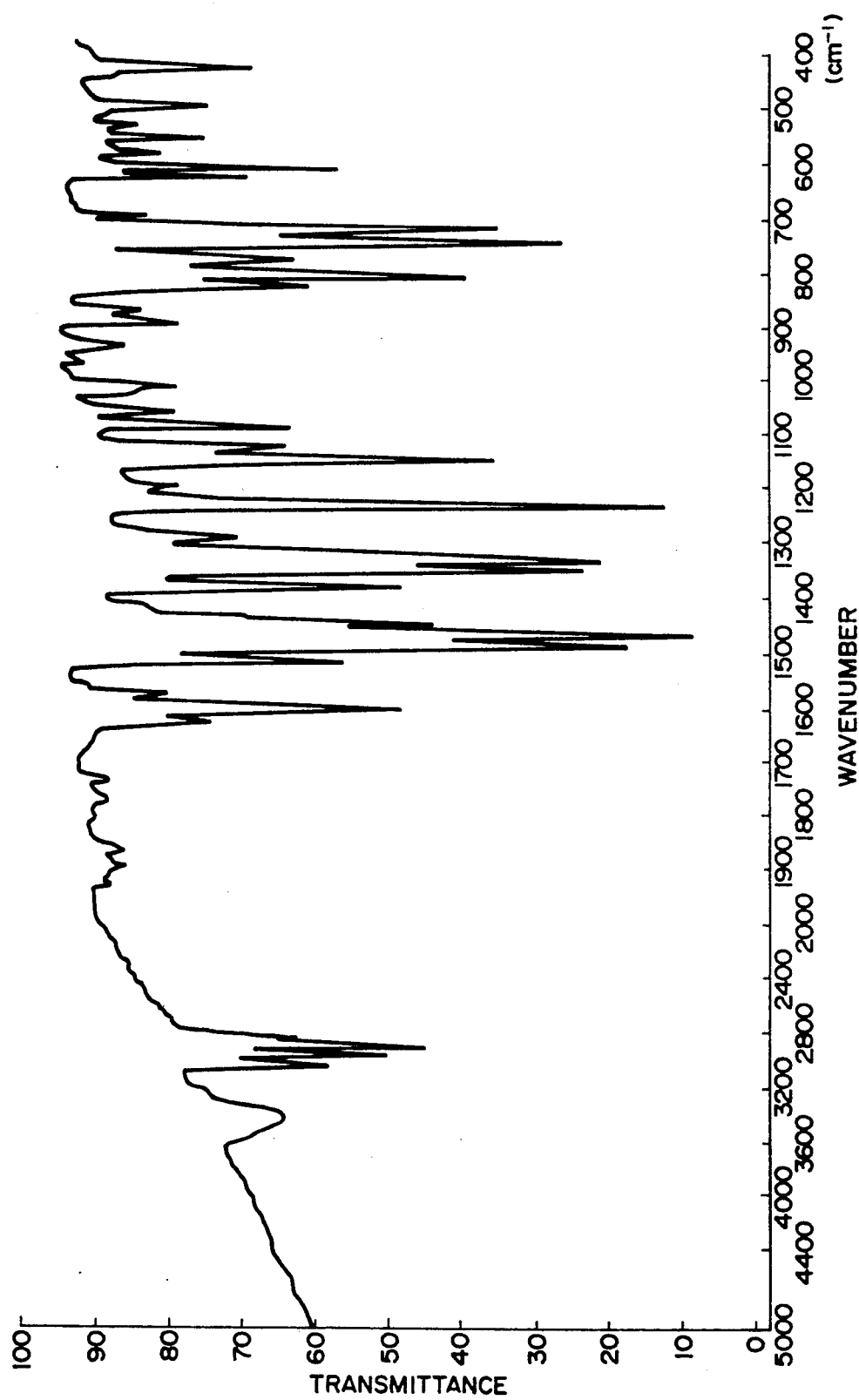
FIG. 7 is an infrared spectrum of aromatic diethyl compound No. 3-14 according to the present invention.
Figure 8:
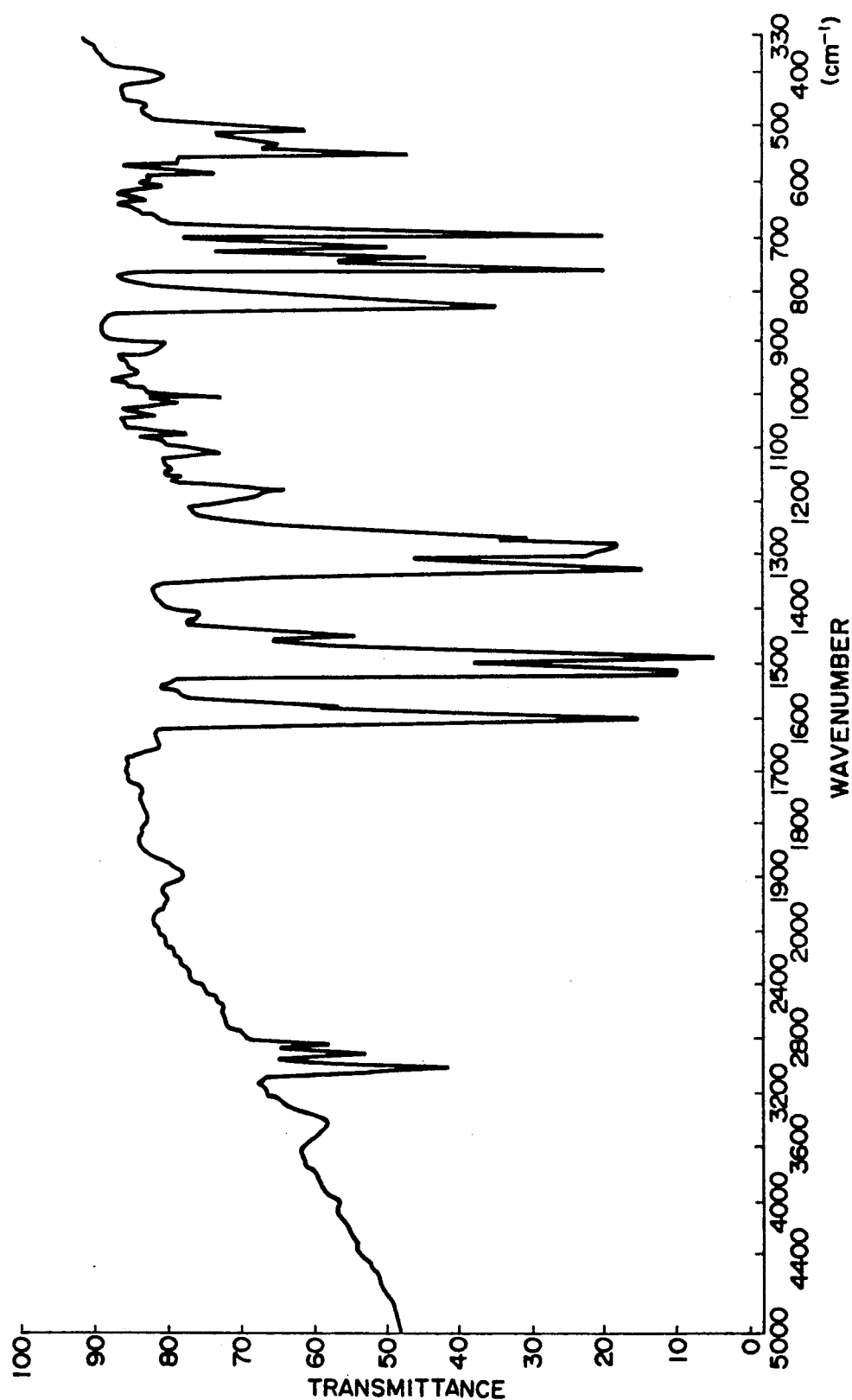
FIG. 8 is an infrared spectrum of aromatic diethyl compound No. 3-15 according to the present invention.

An infrared spectrum of the above synthesized 1,4-bis [2-(4-N,N-diphenylaminophenyl)ethyl]benzene, taken by use of a KBr pellet, is shown in FIG. 4, indicating the disappearance of a peak at 963 cm$^{-1}$ which is characteristic of the C—H out-of-plane deformation vibrations of the trans olefine in the starting material of the above synthesis.

SYNTHESIS EXAMPLES 3-2 TO 3-16

Aromatic diethyl compounds No. 3-2 to 3-16 as listed in the following Table 3 according to the present invention were prepared in the same manner as in Synthesis Example 3-1.

| Synthesis Examples No. | A | m.p. (°C.) | Elemental Analysis Found (Calculated) | | |
|---|---|---|---|---|---|
| | | | % C | % H | % N |
| 3-2 | (4-methylphenyl)-N(CH₃)₂ | 163.7~165.0 | 83.90 (83.82) | 8.71 (8.66) | 7.40 (7.52) |
| 3-3 | (4-methylphenyl)-N(CH₃)(phenyl) | 131.5~132.5 | 87.21 (87.05) | 7.28 (7.31) | 5.44 (5.64) |
| 3-4 | (4-methylphenyl)-N(CH₂-phenyl)₂ | 127.0~128.2 | 88.50 (88.71) | 7.10 (7.15) | 4.05 (4.14) |
| 3-5 | (4-methylphenyl)-N(CH₂-phenyl)(phenyl) | 125.5~127.0 | 88.90 (88.85) | 6.79 (6.83) | 4.16 (4.32) |
| 3-6 | (4-methylphenyl)-N(4-methylphenyl)(phenyl) | 92.5~95.0 | 88.80 (88.84) | 6.85 (6.84) | 4.09 (4.32) |
| 3-7 | (4-methylphenyl)-N(4-methylphenyl)₂ | 118.5~119.0 | 88.88 (88.70) | 7.12 (7.16) | 4.10 (4.14) |
| 3-8 | (4-methylphenyl)-N(2,4-dimethylphenyl)(phenyl) | 121.3~122.5 | 88.98 (88.71) | 6.97 (7.15) | 4.08 (4.14) |
| 3-9 | (3-methyl-4-yl)-N(phenyl)₂ | 162.0~162.5 | 88.67 (88.85) | 6.93 (6.83) | 4.15 (4.32) |
| 3-10 | (4-methylphenyl)-N(4-methoxyphenyl)(phenyl) | 125.0~126.0 | 84.92 (84.67) | 6.68 (6.51) | 4.13 (4.12) |

-continued

| Synthesis Examples No. | A | m.p. (°C.) | Elemental Analysis Found (Calculated) | | |
|---|---|---|---|---|---|
| | | | % C | % H | % N |
| 3-11 | (structure: -C6H4-N(-C6H4-OCH3)2) | 136.8–138.0 | 81.18 (81.05) | 6.69 (6.53) | 3.62 (3.78) |
| 3-12 | (structure: -C6H4-N(-C6H4-Cl)(-C6H5)) | Oily Material | 80.21 (80.00) | 5.48 (5.56) | 3.98 (4.06) |
| 3-13 | (structure: naphthyl-N(-C6H5)2) | 177.5–180.5 | 89.74 (89.96) | 6.30 (6.15) | 3.80 (3.89) |
| 3-14 | (structure: N-ethylcarbazolyl) | 192.0–193.0 | 87.52 (87.64) | 6.91 (6.98) | 5.41 (5.38) |
| 3-15 | (structure: -C6H4-N(-C6H4-C6H5)2) | 181.5–182.5 | 90.67 (90.87) | 6.00 (6.10) | 2.89 (3.03) |
| 3-16 | (structure: -C6H4-N(-C6H4-CN)(-C6H5)) | 223.0–225.0 | 86.10 (85.93) | 5.60 (5.72) | 8.12 (8.35) |

SYNTHESIS EXAMPLE 3-17

Synthesis of 1,3-bis[2-(4-N,N-diphenylaminophenyl)ethyl]benzene 3.00 g of 1,3-bis(4-N,N-diphenylaminostyryl)benzene was dissolved in 60 ml of tetrahydrofuran. To this solution, 0.60 g of a 5% paradium-carbon was added and the 1,3-bis(4-N,N-diphenylaminostyryl)benzene was hydrogenated with a hydrogen pressure of 1 atm at 26° C. in a shaker hydrogenation apparatus. After the hydrogenation, the reaction mixture was filtered together with sellaite to obtain a filtrate. The filtrate was then distilled under reduced pressure to remove tetrahydrofuran therefrom, so that light yellow crystals were obtained. The white crystals were chromatographed over a column of silca gel-toluene/n-hexane (volume ratio 1/2), and then recrystallized from a mixed solvent of ethanol and ethyl acetate, whereby 2.57 g of 1,3-bis[2-(4-N,N-diphenylaminophenyl)ethyl]benzene, diethyl aromatic compound No. 3-17 according to the present invention, was obtained in the form of white needle-like crystals in a 85.7% yield. The melting point of the product was at 119.0°~120.0° C.

The result of the elemental analysis of the thus obtained 1,3-bis[2-(4-N,N-diphenylaminophenyl)ethyl]benzene were as follows:

| | % C | % H | % N |
|---|---|---|---|
| Found | 89.13 | 6.46 | 4.50 |
| Calculated | 88.99 | 6.50 | 4.51 |

The above calculation was based on the formula for 1,3-bis[2-(4-N,N-diphenylaminophenyl)ethyl]benzene of $C_{46}H_{40}N_2$.

Figure 9:
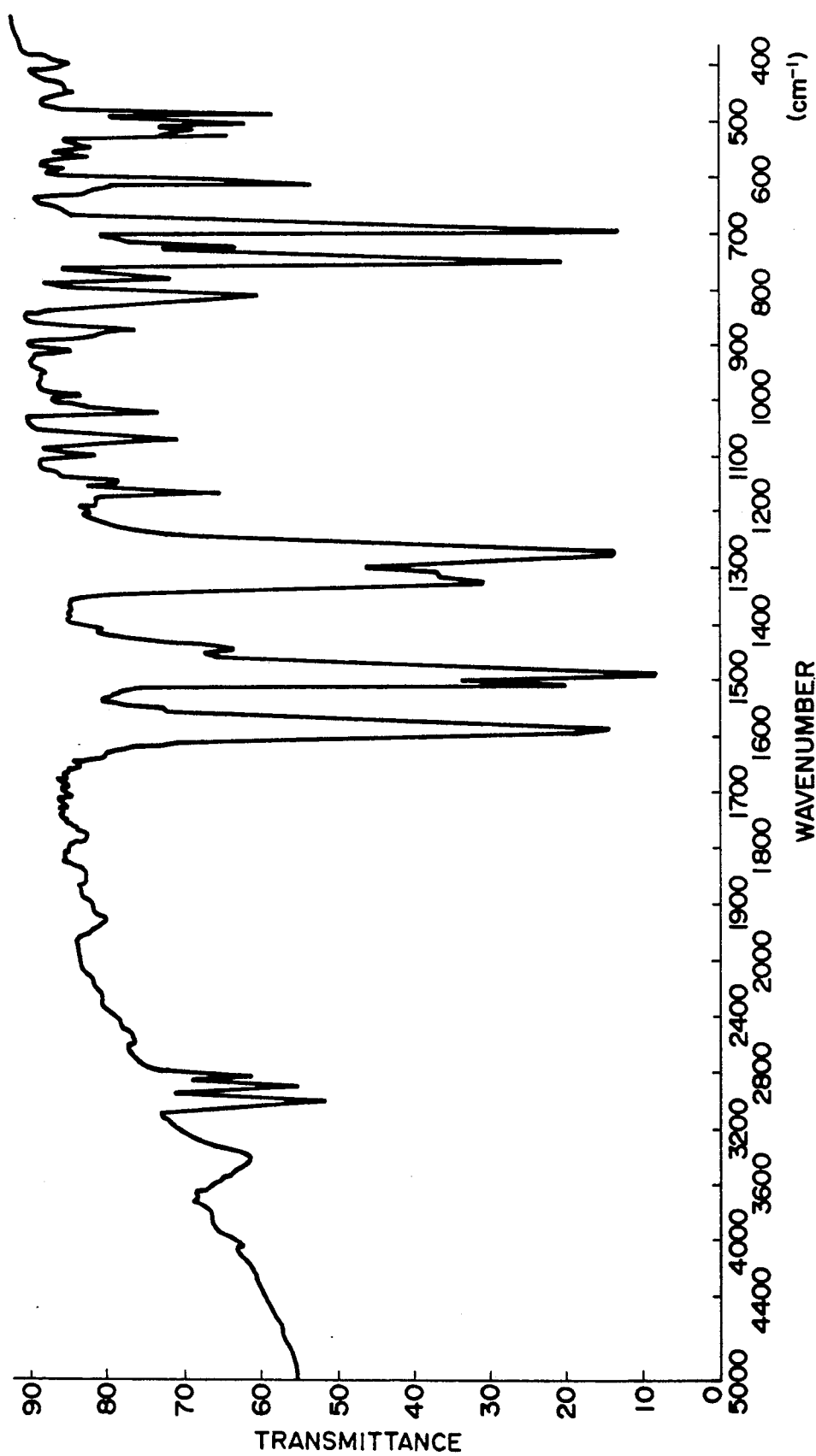
FIG. 9 is an infrared spectrum of aromatic diethyl compound No. 3-17 according to the present invention.
Figure 10:
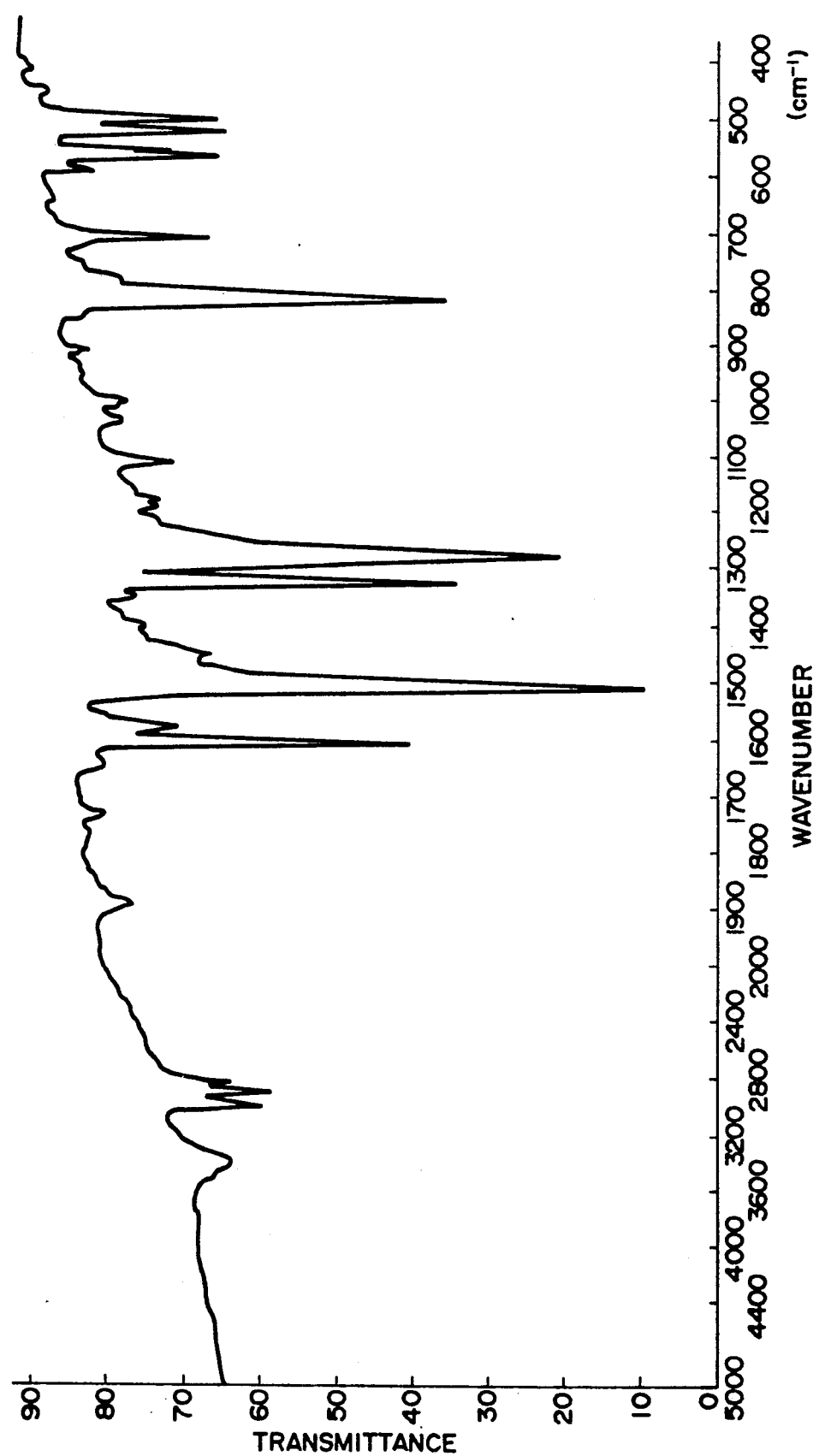
FIG. 10 is an infrared spectrum of aromatic diethyl compound No. 3-21 according to the present invention.
Figure 11:
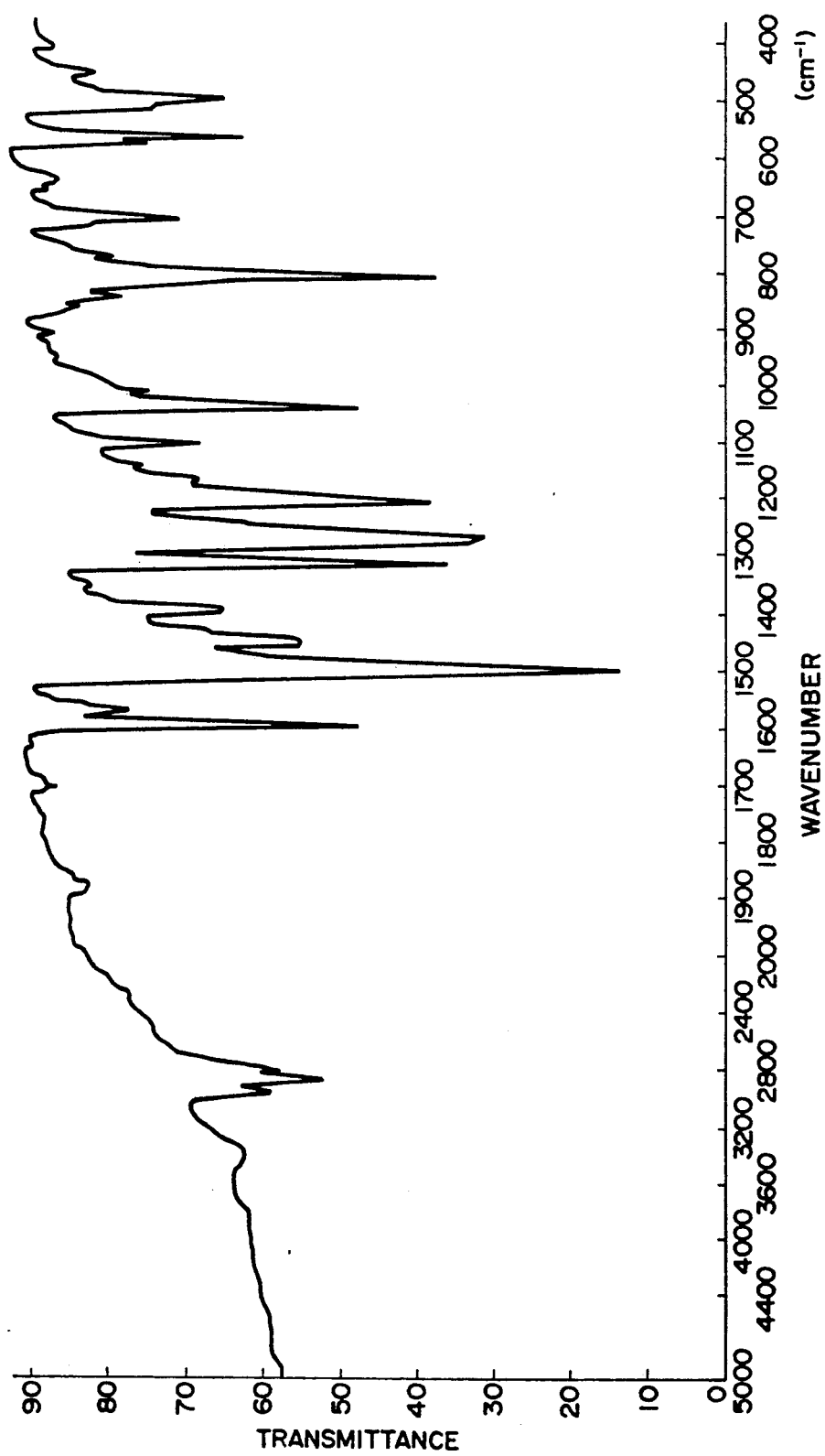
FIG. 11 is an infrared spectrum of aromatic diethyl compound No. 3-23 according to the present invention.

An infrared spectrum of the above synthesized 1,4-bis[2-(4-N,N-diphenylaminophenyl)ethyl]benzene, taken by use of a KBr pellet, is shown in FIG. 9, indicating the disappearance of a peak at 960 cm$^{-1}$ which is characteristic of the C—H out-of-plane deformation vibrations of the trans olefine in the starting material of the above synthesis.

An ultraviolet spectrum of the above product was $\lambda_{max}^{CH_3CN}$ 299 nm ($\epsilon$0.48000)

SYNTHESIS EXAMPLES 3-18 TO 3-24

Aromatic diethyl compounds No. 3-18 to 3-24 as listed in the following Table 4 according to the present invention were prepared in the same manner as in Synthesis Example 3-1.

TABLE 4

A—CH$_2$CH$_2$—Ar—CH$_2$CH$_2$—A

| Synthesis Examples No. | Ar | A | m.p. (°C.) | Elemental Analysis Found (Calculated) | | |
|---|---|---|---|---|---|---|
| | | | | % C | % H | % N |
| 3-18 |  | 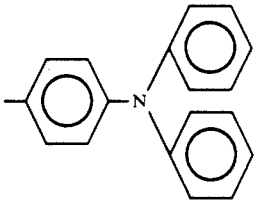 | 132.0~133.5 | 88.97 (88.99) | 6.72 (6.50) | 4.29 (4.51) |
| 3-19 | 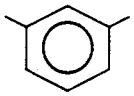 | 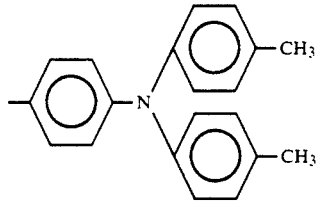 | Oily Material | 88.73 (88.71) | 7.15 (7.15) | 4.20 (4.14) |
| 3-20 | 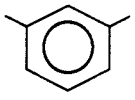 | 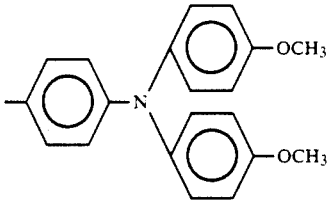 | Oily Material | 81.10 (81.05) | 6.55 (6.53) | 3.60 (3.78) |
| 3-21 | 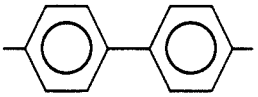 | 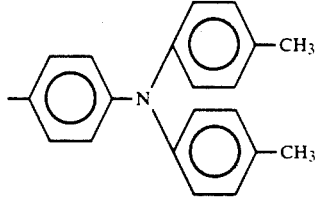 | 187.0~188.0 | 89.39 (89.31) | 7.06 (6.97) | 3.67 (3.72) |
| 3-22 | 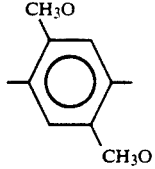 | 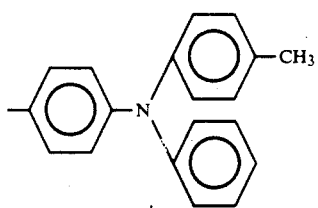 | 167.0~168.0 | 84.84 (84.70) | 6.67 (6.84) | 3.84 (3.95) |
| 3-23 | 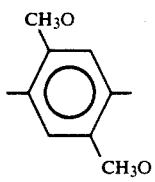 | 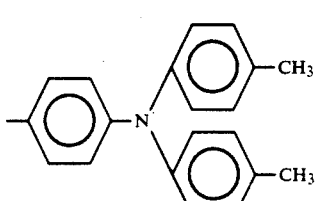 | 200.5~201.5 | 84.47 (84.73) | 6.94 (7.13) | 3.81 (3.80) |

TABLE 4-continued

A—CH$_2$CH$_2$—Ar—CH$_2$CH$_2$—A

| Synthesis Examples No. | Ar | A | m.p. (°C.) | Elemental Analysis Found (Calculated) | | |
|---|---|---|---|---|---|---|
| | | | | % C | % H | % N |
| 3-24 | (2,5-dimethoxyphenyl with CH$_3$O groups) | (N-tolyl-N-(methoxyphenyl)-phenyl) | 160.0 | 81.02 (81.04) | 6.45 (6.54) | 3.64 (3.78) |

Specific examples of aromatic diethyl compounds according to the present invention are listed in the following Table 5, which can be employed as photoconductive materials for use in the electrophotographic photoconductors according to the present invention.

TABLE 5

$$A-CH_2CH_2-\underset{}{\underset{}{\bigcirc}}-CH_2CH_2-A \quad (III)$$

| Aromatic Diethyl Compound No. | A |
|---|---|
| 1 | carbazol-9-yl with N—CH₃ |
| 2 | carbazol-9-yl with N—C₂H₅ |
| 3 | carbazol-9-yl with N—C₃H₇ |
| 4 | carbazol-9-yl with N—C₄H₉ |
| 5 | carbazol-9-yl with N—C₆H₅ |

-continued
6 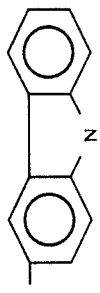
7 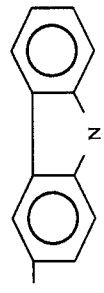
$$A-CH_2CH_2 \underset{}{\underset{}{\bigcirc}} CH_2CH_2-A \quad (III)$$
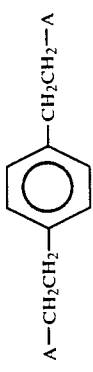
(wherein $-A = -Ar^2-N\begin{pmatrix}R^1\\R^2\end{pmatrix}$)
| Aromatic Diethyl Compound No. | $Ar^2$ | $R^1$ | $R^2$ |
|---|---|---|---|
| 8 | 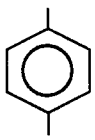 | —CH$_3$ | —CH$_3$ |
| 9 | 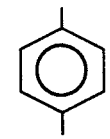 | —CH$_3$ | 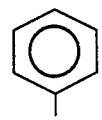 |

-continued
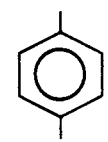 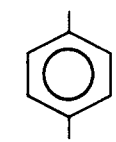 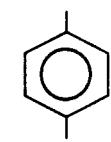 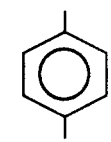 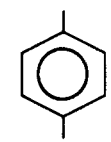 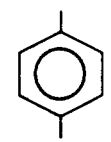 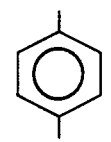 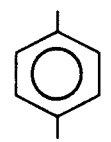 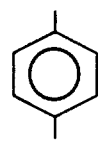

-continued
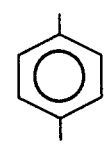 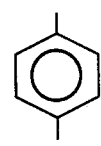 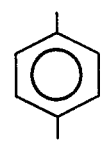 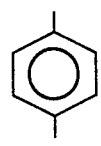 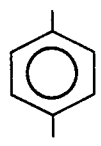 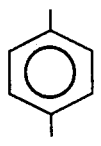 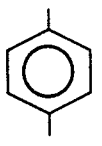 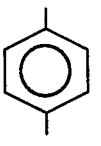 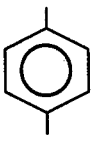
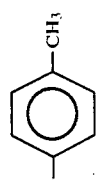 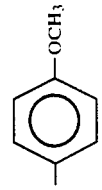 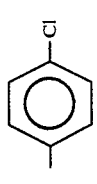 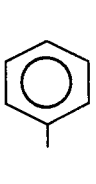 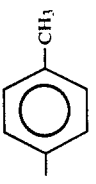 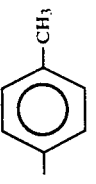 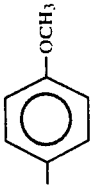 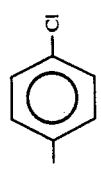
19　20　21　22　23　24　25　26　27

-continued
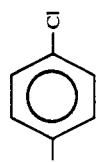 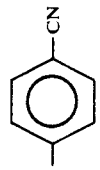 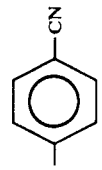 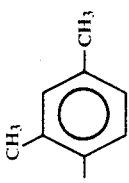 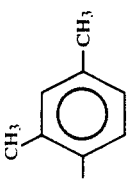 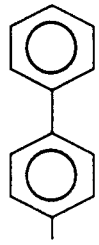 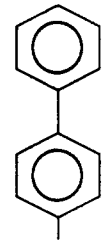 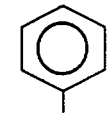
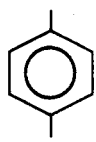 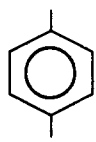 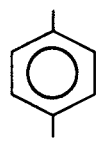 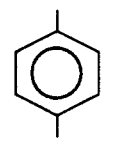 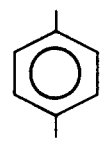 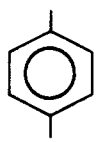 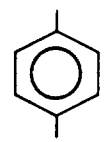 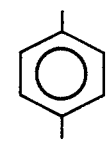
28  29  30  31  32  33  34  35

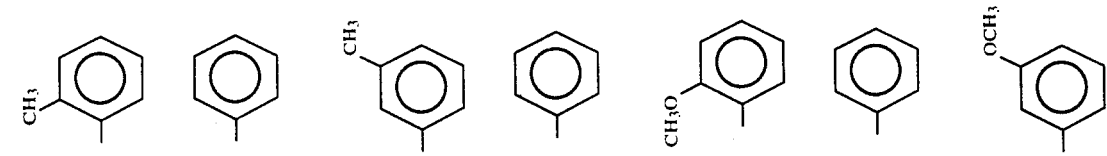
-continued
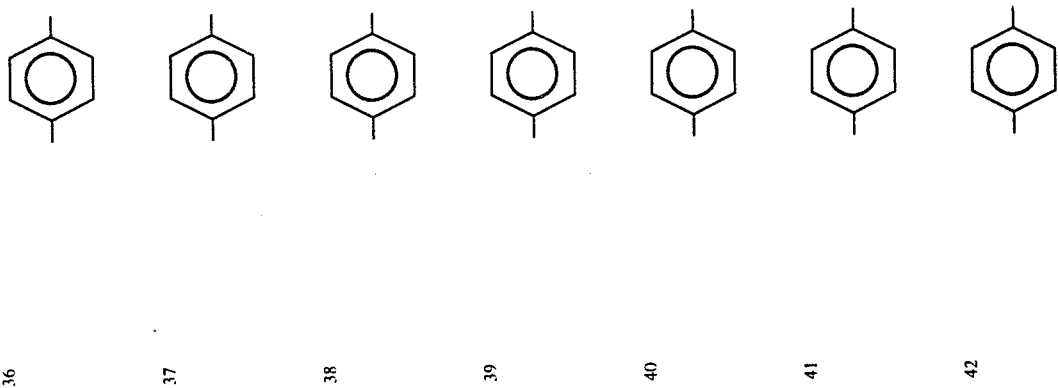

-continued
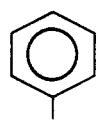 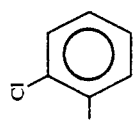 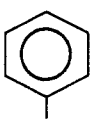 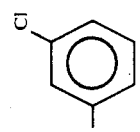 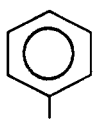 —CH₃ 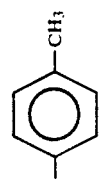
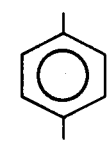 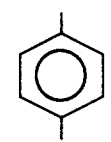 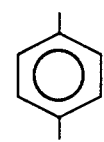 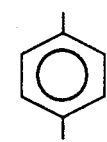 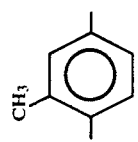 —CH₃ 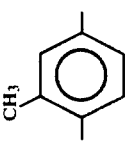
43  44  45  46  47  48  49

-continued
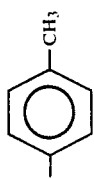 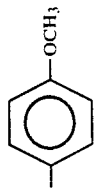 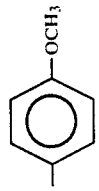 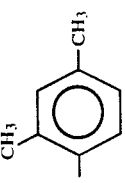 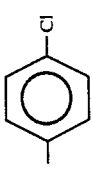 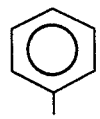 
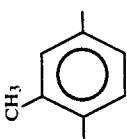 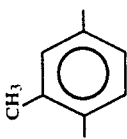 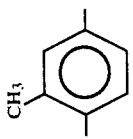 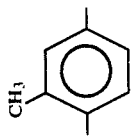 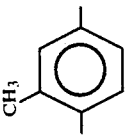 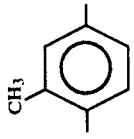
50  51  52  53  54  55  56

-continued
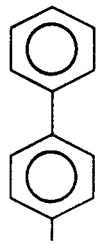  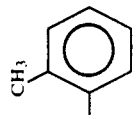  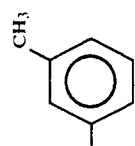 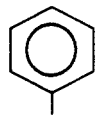 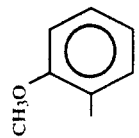
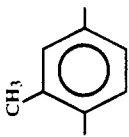 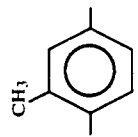 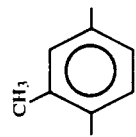 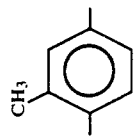 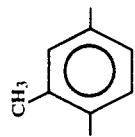 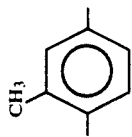 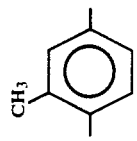
57　58　59　60　61　62　63

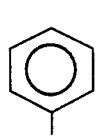 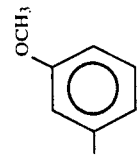 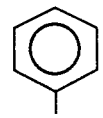 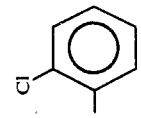 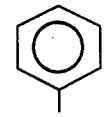 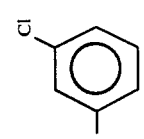 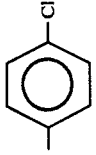
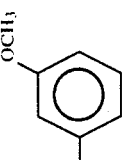 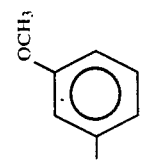 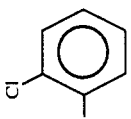 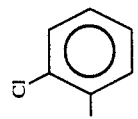 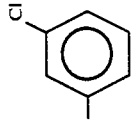 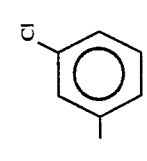 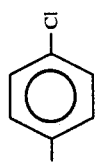
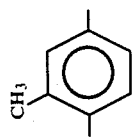 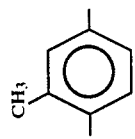 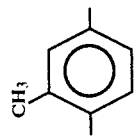 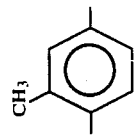 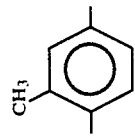 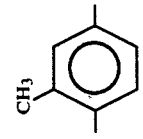
64  65  66  67  68  69  70

-continued
| —CH₃ | 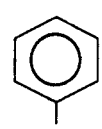 | 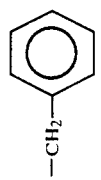 | 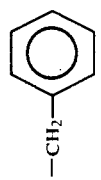 | 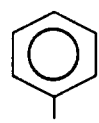 |
| —CH₃ | —CH₃ | | | |
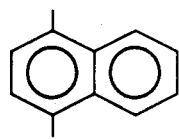 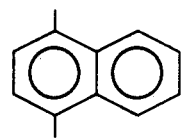 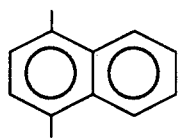 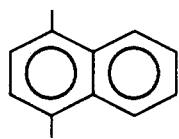 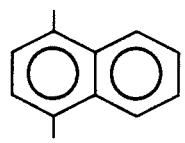
71  72  73  74  75

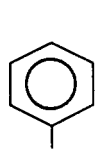 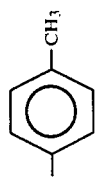 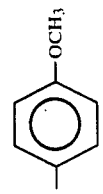 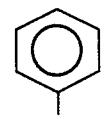 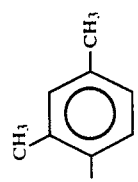
-continued
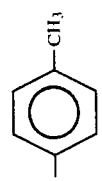 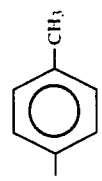 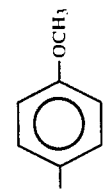 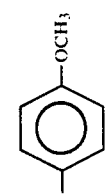 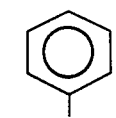
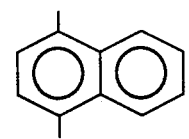 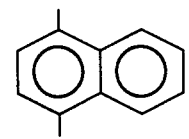 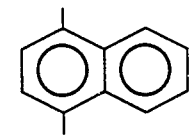 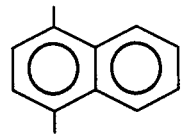 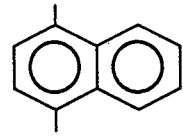
76  77  78  79  80

-continued
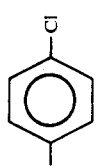 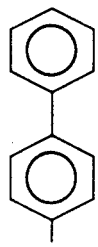 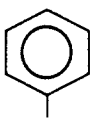 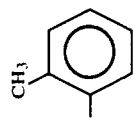 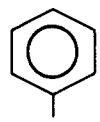
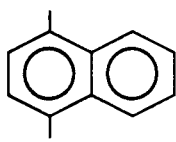 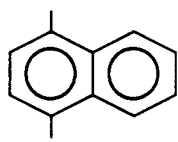 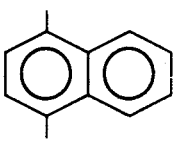 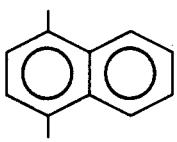 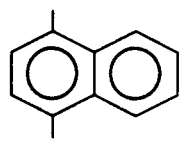
81     82     83     84     85

-continued
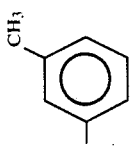 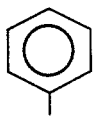 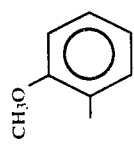 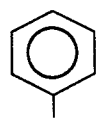 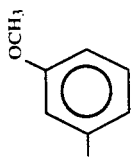
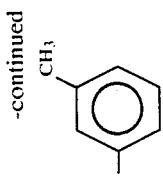 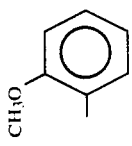 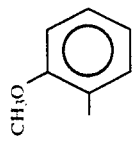 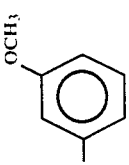 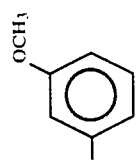
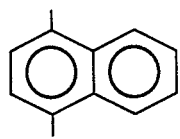 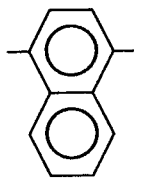 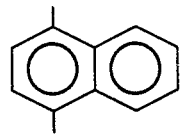 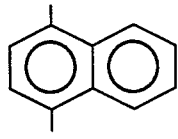 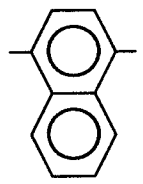
| 86 | 87 | 88 | 89 | 90 |

-continued
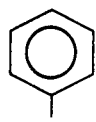 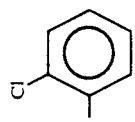 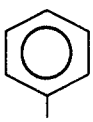 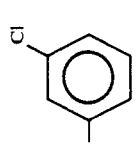 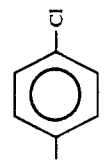
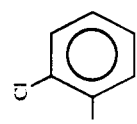 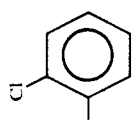 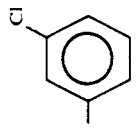 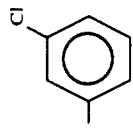 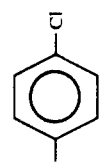
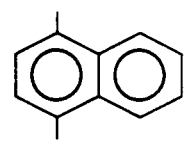 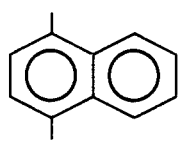 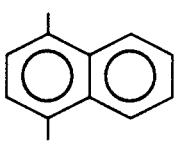 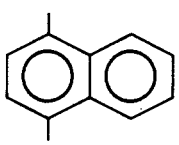 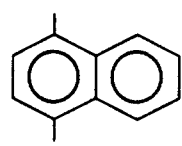
91     92     93     94     95

-continued
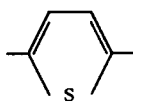 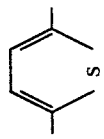 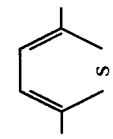 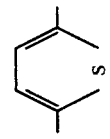 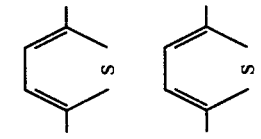

-continued
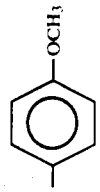 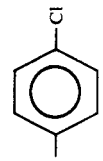 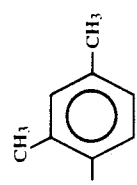 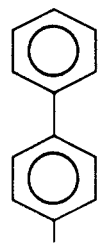  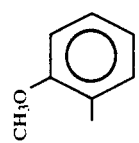 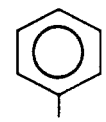 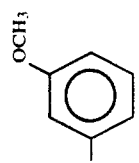
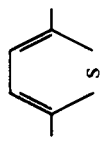 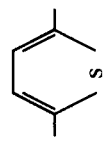 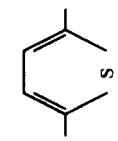 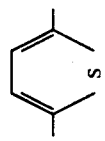 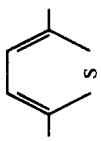 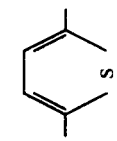 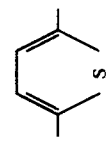 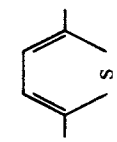
| 104 | 105 | 106 | 107 | 108 | 109 | 110 | 111 |

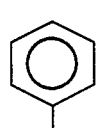 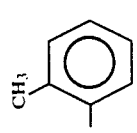 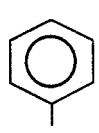 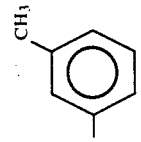 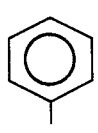 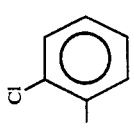 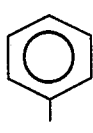
-continued
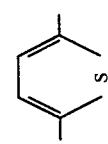 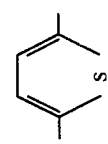 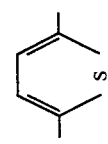 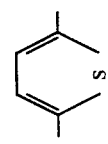 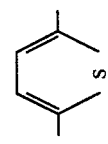 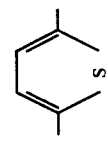 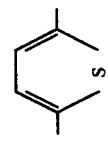
112  113  114  115  116  117  118

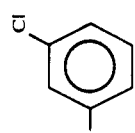 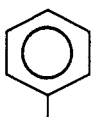 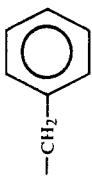 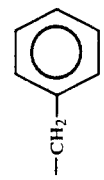
-continued
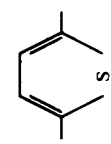 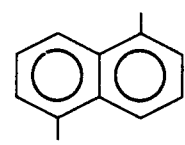 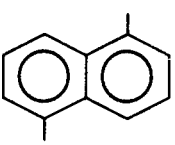 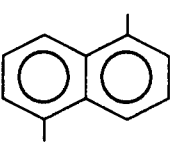 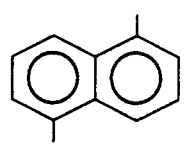
119     120     121     122     123

-continued
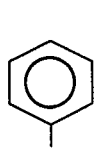 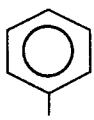 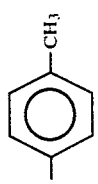 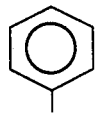 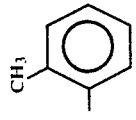
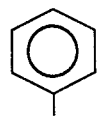 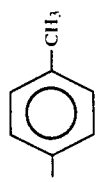 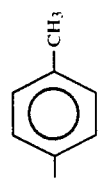 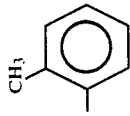 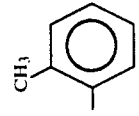
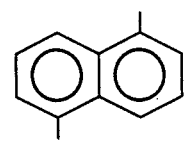 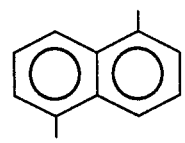 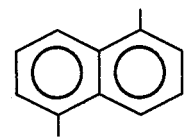 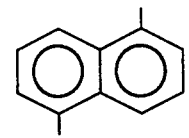 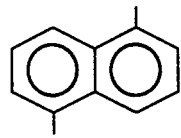
124     125     126     127     128

-continued
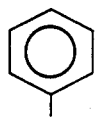 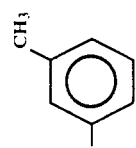 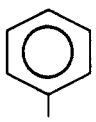 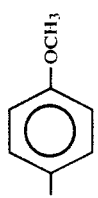 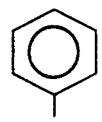
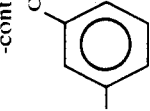 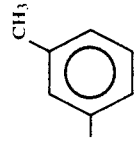 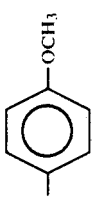 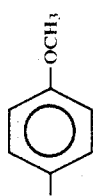 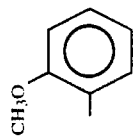
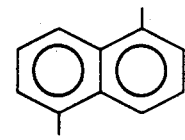 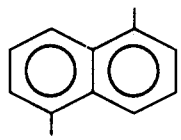 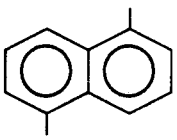 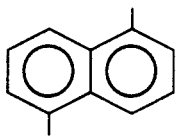 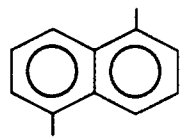
129     130     131     132     133

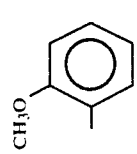 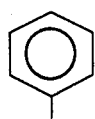 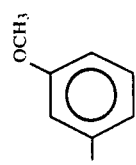 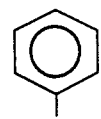 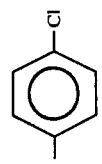
-continued
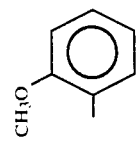 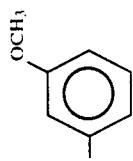 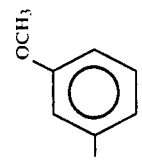 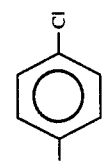 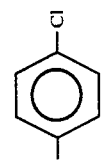
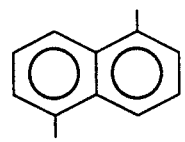 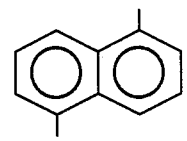 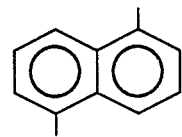 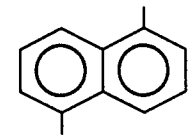 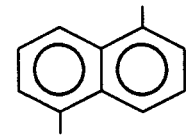
134　　　135　　　136　　　137　　　138

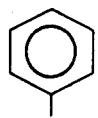 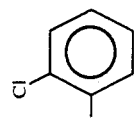 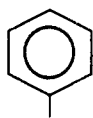 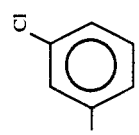 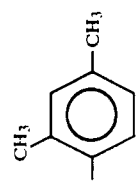
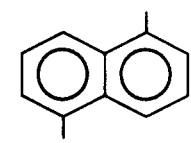 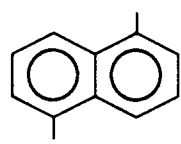 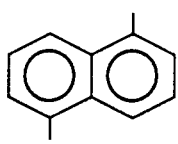 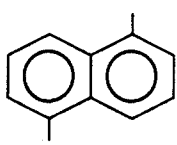 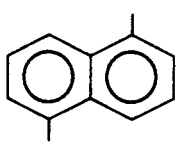
139   140   141   142   143

-continued
| 144 | 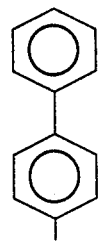 | 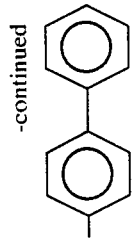 | 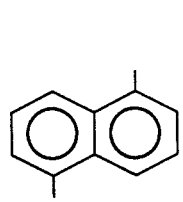 |
| --- | --- | --- | --- |
| 145 | 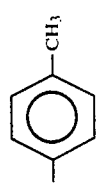 | 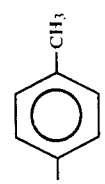 | 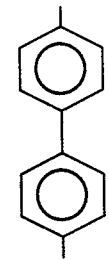 |
| 146 | 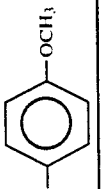 | 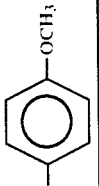 | 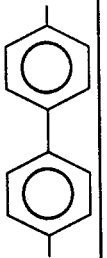 |

A—CH₂CH₂—Ar—CH₂CH₂—A (III)
| Aromatic Diethyl Compound No. | Ar | A |
|---|---|---|
| 147 | 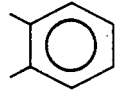 | 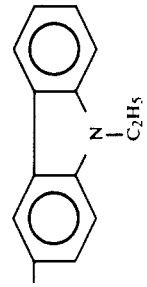 |
| 148 | 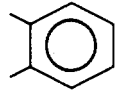 | 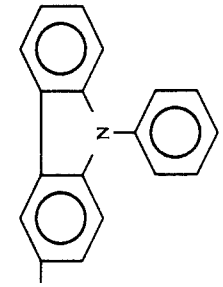 |
| 149 | 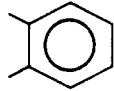 | 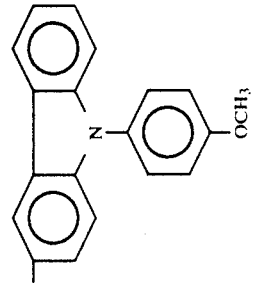 |
| 150 |  | 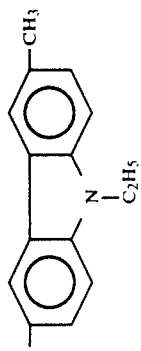 |

-continued
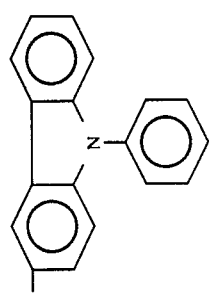 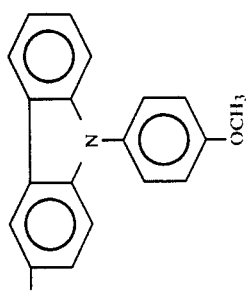 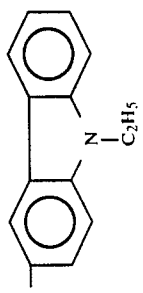 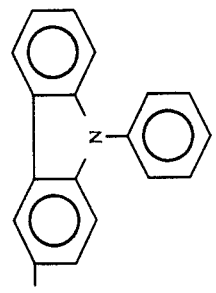
  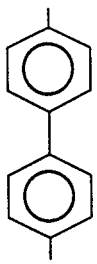 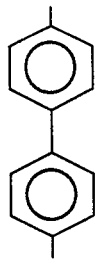
151    152    153    154

-continued
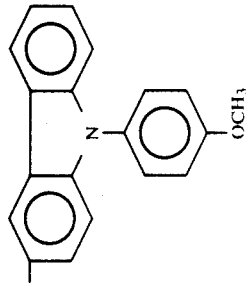 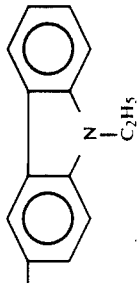 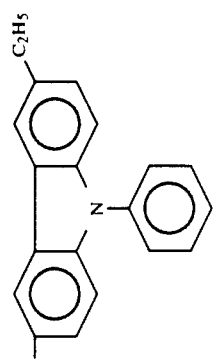 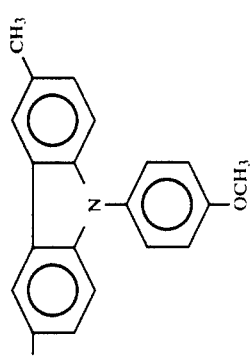
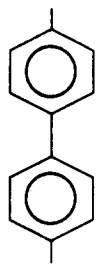 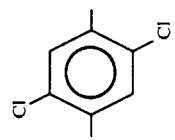 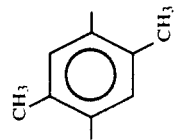 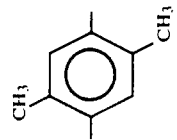
155     156     157     158

-continued
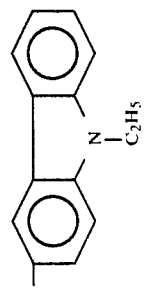 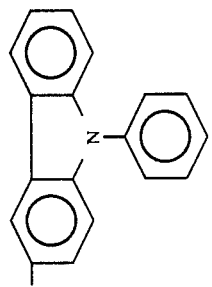 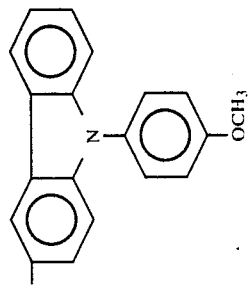 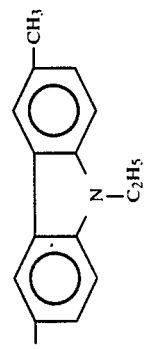 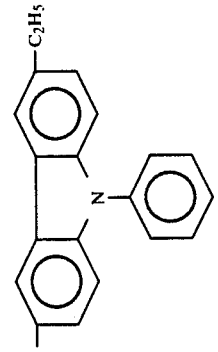
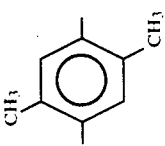 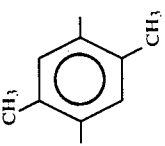
159   160   161   162   163

-continued
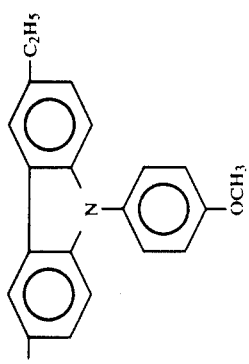 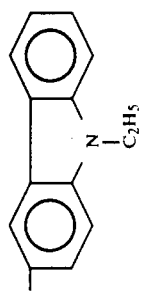 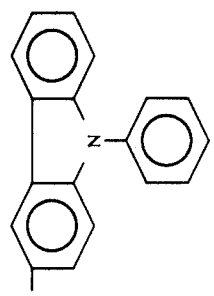 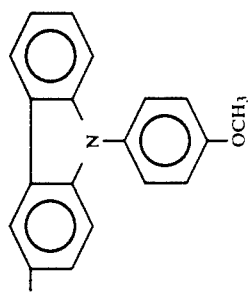
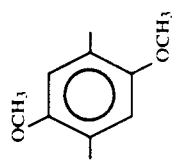 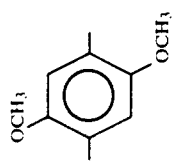 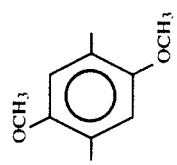 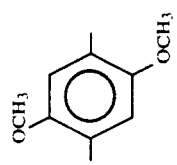
164     165     166     167

-continued
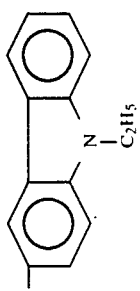 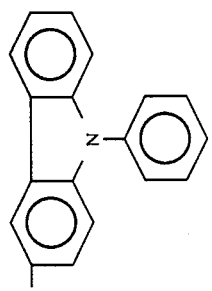 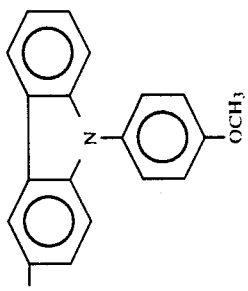 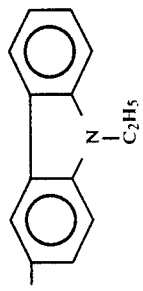
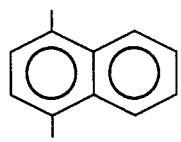 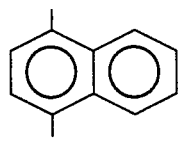 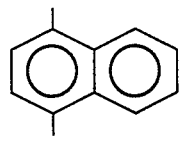 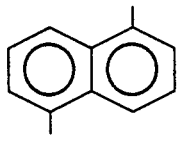
168 169 170 171

-continued
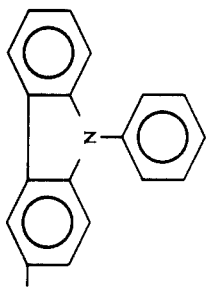 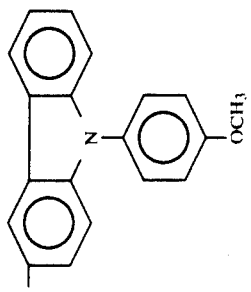 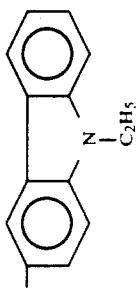 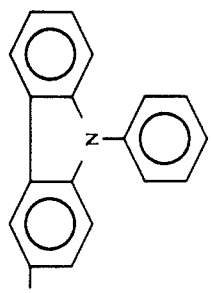
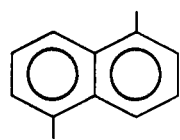 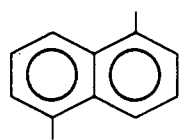 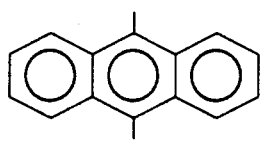 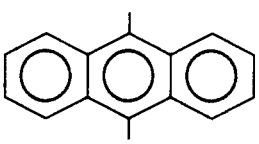
172     173     174     175

-continued
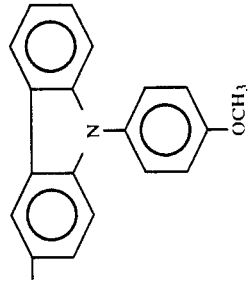 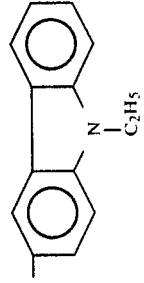 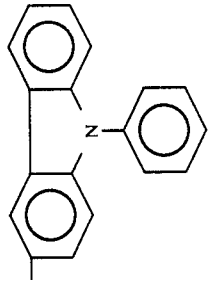 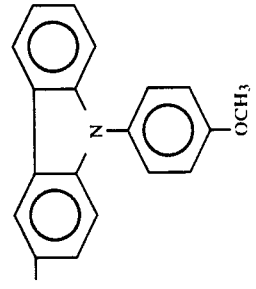 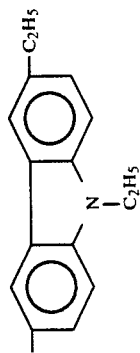
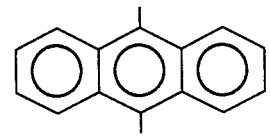 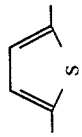 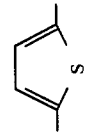 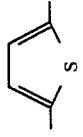 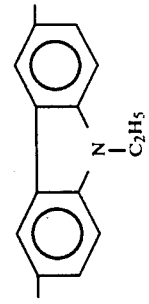
176  177  178  179  180

-continued
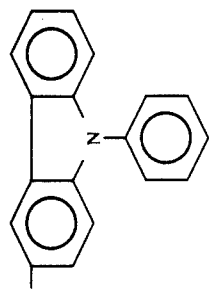
181
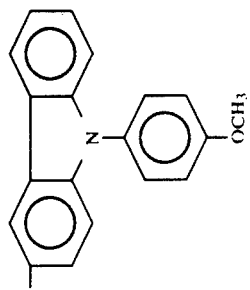
182
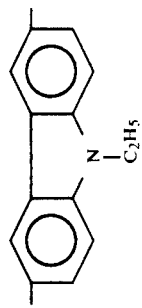
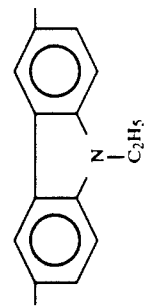

A—CH$_2$CH$_2$—Ar—CH$_2$CH$_2$—A
$$-A = -Ar^2-N\begin{pmatrix}R^1\\R^2\end{pmatrix}$$
(wherein
| Aromatic Diethyl Compound No. | Ar | Ar$^2$ | R$^1$ | R$^2$ |
|---|---|---|---|---|
| 183 | 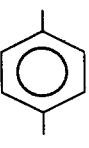 | 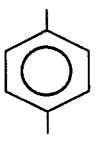 | —CH$_3$ | —CH$_3$ |
| 184 | 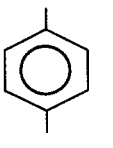 | 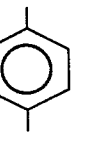 | —CH$_3$ | 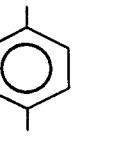 |
| 185 | 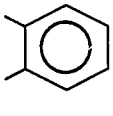 | 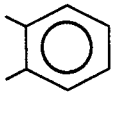 | —CH$_3$ | 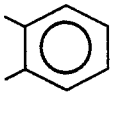 |
| 186 |  |  | —CH$_2$—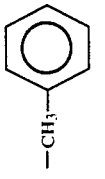 | —CH$_2$—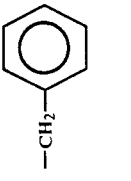 |
| 187 | 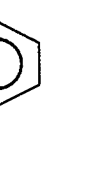 | 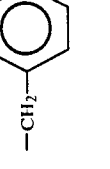 | —CH$_2$— | —CH$_2$— |
| 188 |  | 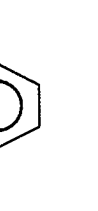 | —CH$_2$——OCH$_3$ | —CH$_2$——OCH$_3$ |

-continued
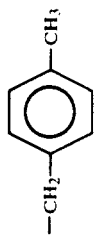 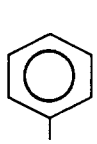 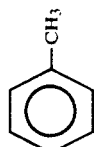 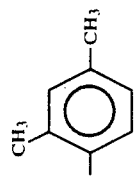 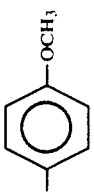 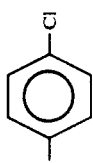 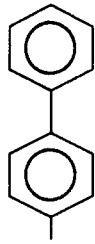
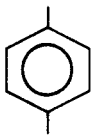 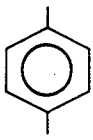 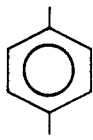 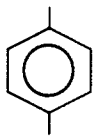 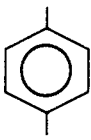 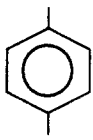 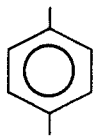
 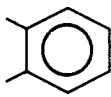 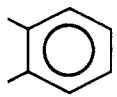 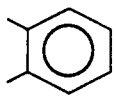   
189  190  191  192  193  194  195

-continued

| | 196 | 197 | 198 | 199 | 200 | 201 | 202 |

-continued
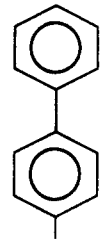 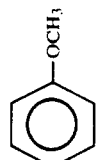 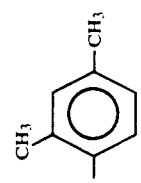 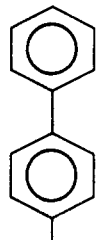 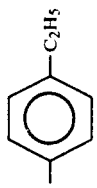 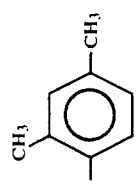 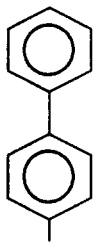
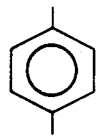 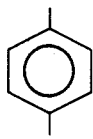 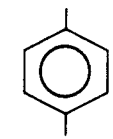 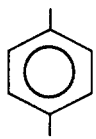 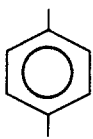 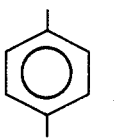 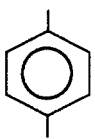
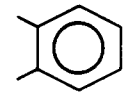 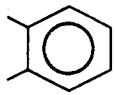 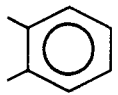 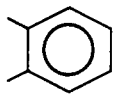 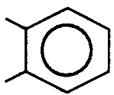 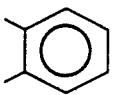 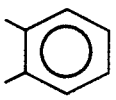
203 204 205 206 207 208 209

-continued
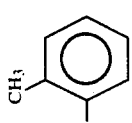 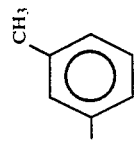 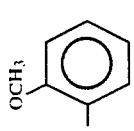 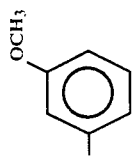 —CH₃ —CH₃ —CH₃
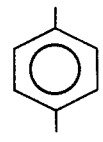 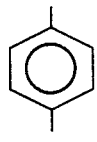 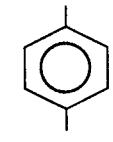 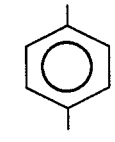 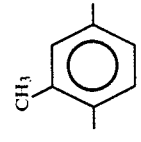 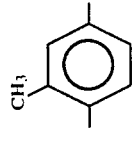 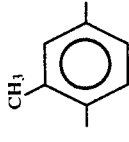
210 211 212 213 214 215 216

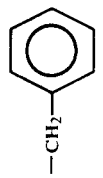 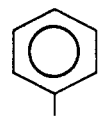 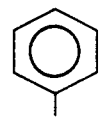 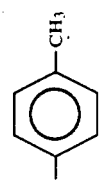 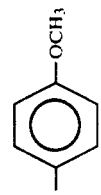 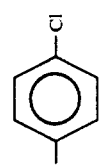 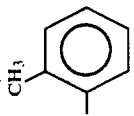
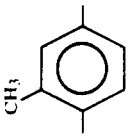 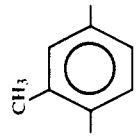 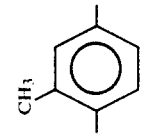 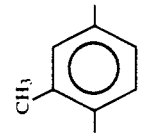 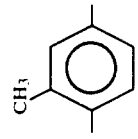 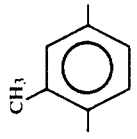 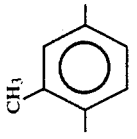
| 217 | 218 | 219 | 220 | 221 | 222 | 223 |

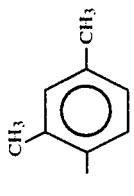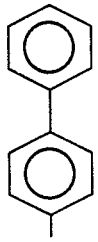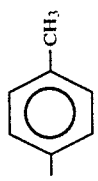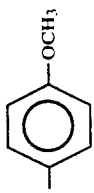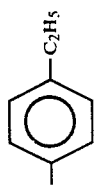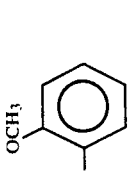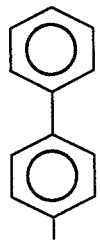
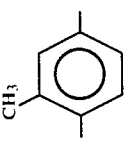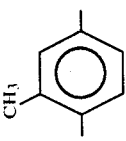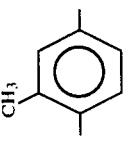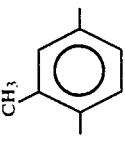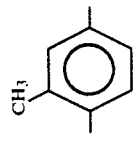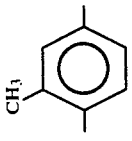
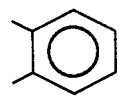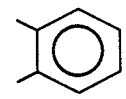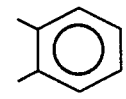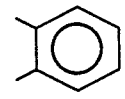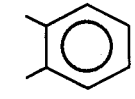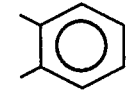
224 225 226 227 228 229 230

-continued
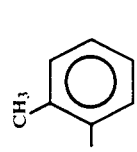 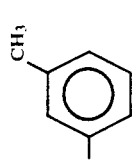 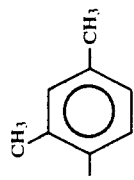 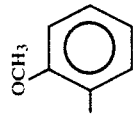 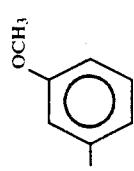 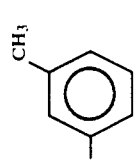 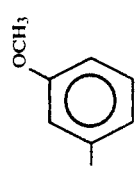
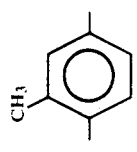 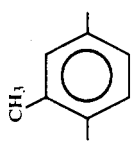 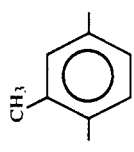 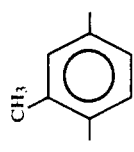 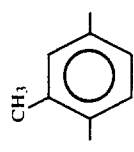 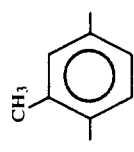 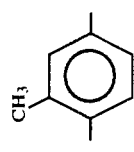
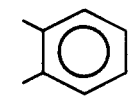 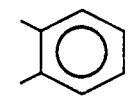 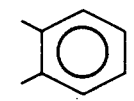 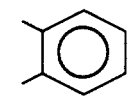 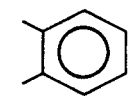 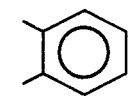 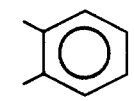
231  232  233  234  235  236  237

-continued
| 238 | 239 | 240 | 241 | 242 |
|---|---|---|---|---|
| —CH₃ | 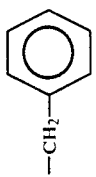 | 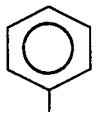 | 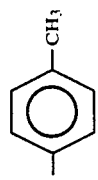 | 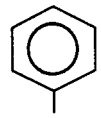 |
| —CH₃ | 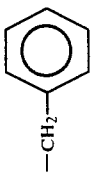 | 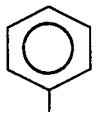 | 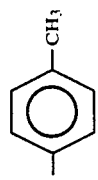 | 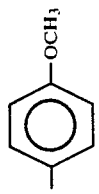 |
| 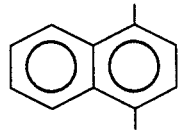 | 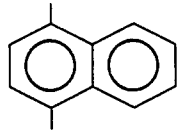 | 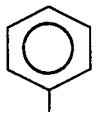 | 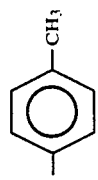 | 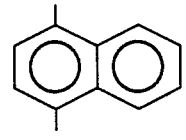 |
| 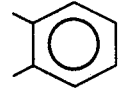 | 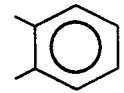 | 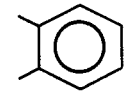 | 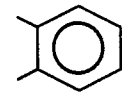 | |

-continued
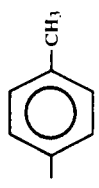 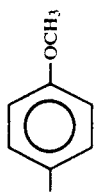 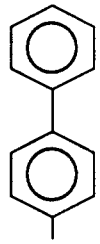 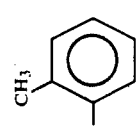 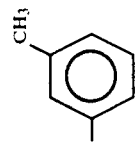
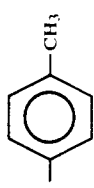 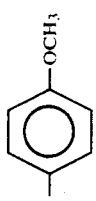 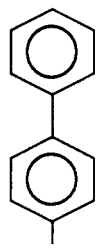 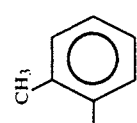 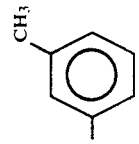
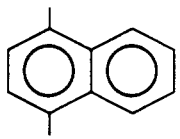 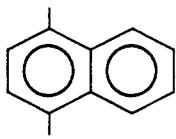 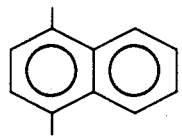 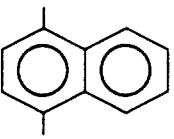 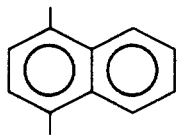
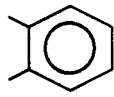 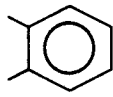 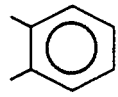 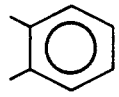 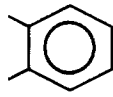
243     244     245     246     247

-continued
| 248 | 249 | 250 | 251 | 252 | 253 | 254 |
|---|---|---|---|---|---|---|
| 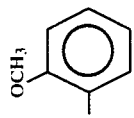 | 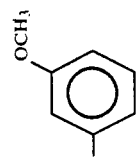 | —CH₃ | 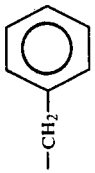 | 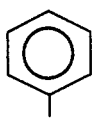 | 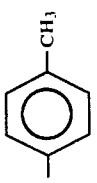 | 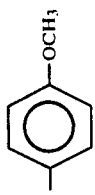 |
| 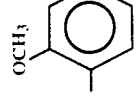 | 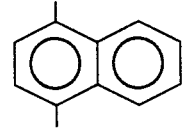 | —CH₃ | 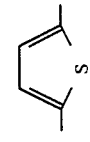 | 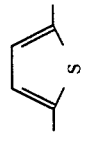 | 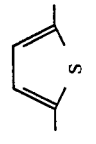 |  |
| 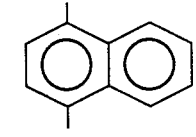 | 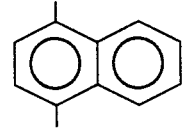 | 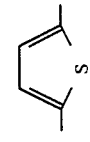 | 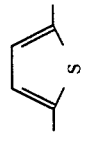 | 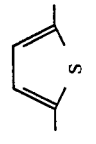 |  | 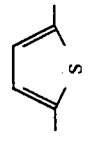 |
| 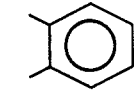 | 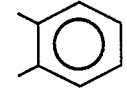 | 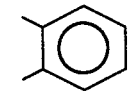 | 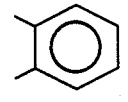 | 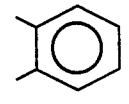 | | 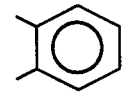 |

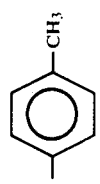 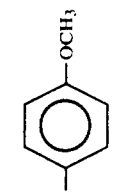 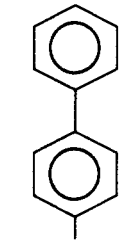 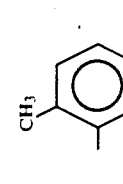 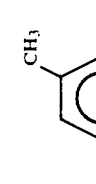 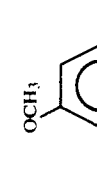 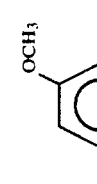
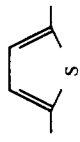 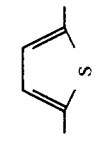 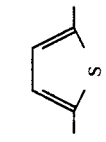 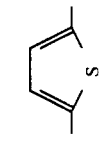 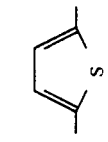 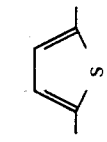 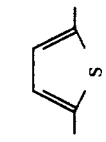
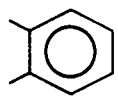 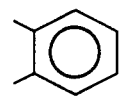 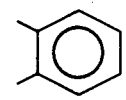 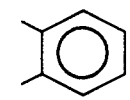 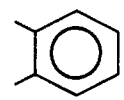 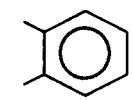 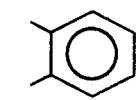
255 256 257 258 259 260 261

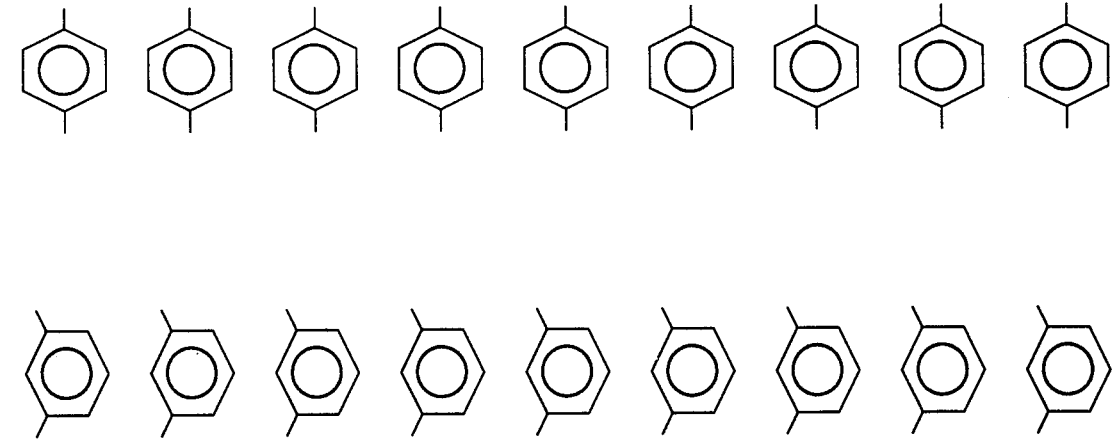

-continued
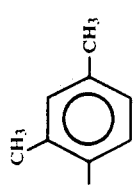 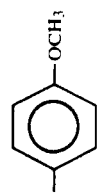 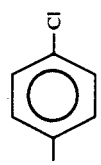 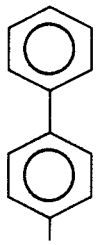 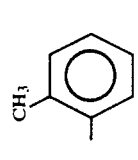 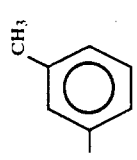 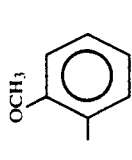 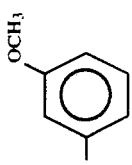
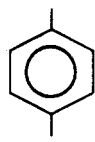 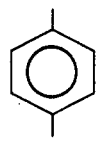 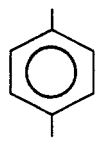 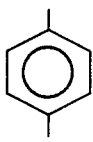 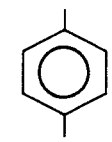 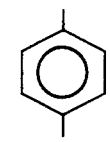 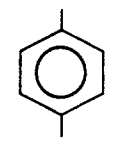 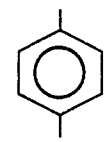
    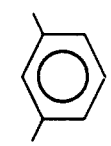 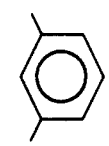 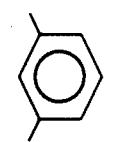 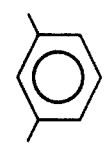
271 272 273 274 275 276 277 278

-continued
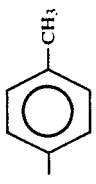 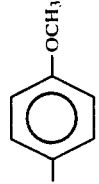 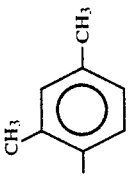 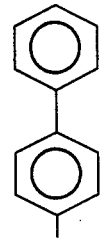 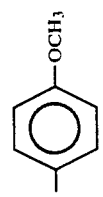 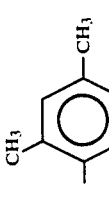 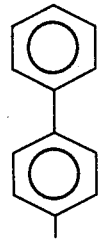 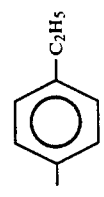
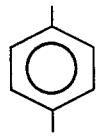 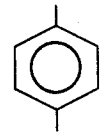 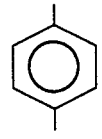 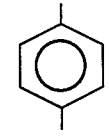 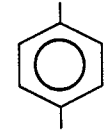 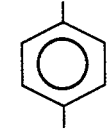 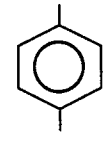 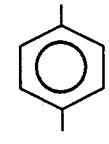
 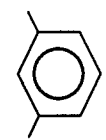      
279 280 281 282 283 284 285 286

-continued
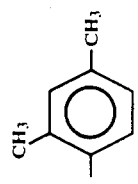 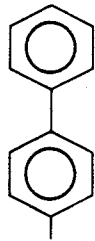 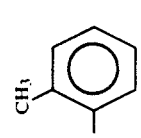 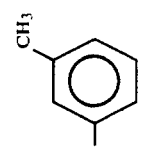 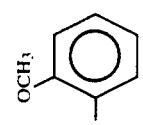 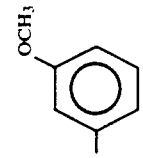 —CH₃
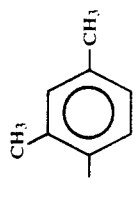 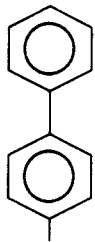 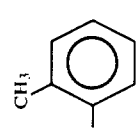 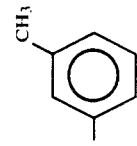 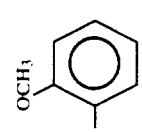 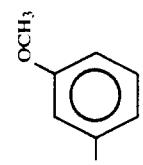 —CH₃
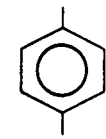 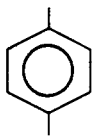 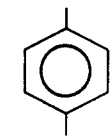 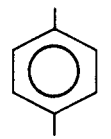 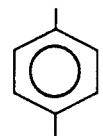 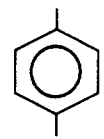 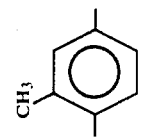
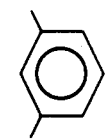  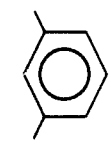 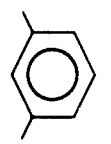   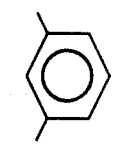
287    288    289    290    291    292    293

-continued
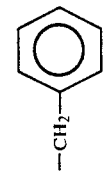 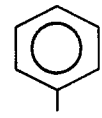  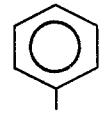 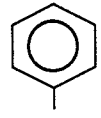 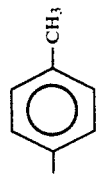 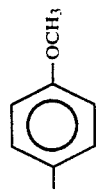
—CH₃  —CH₃
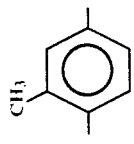 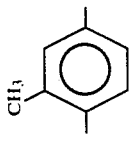 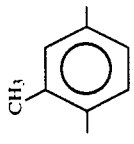 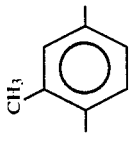 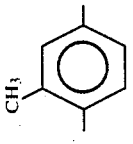 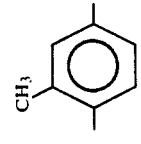
294  295  296  297  298  299  300

-continued
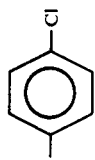 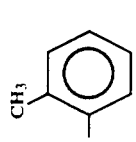 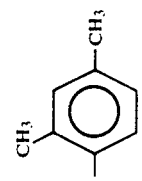 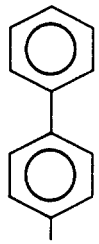
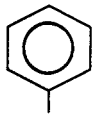 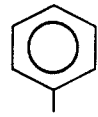 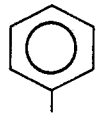 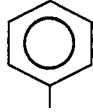
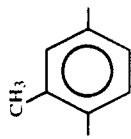 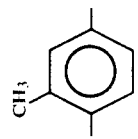 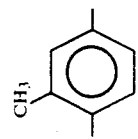 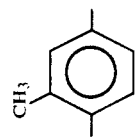
   
301  302  303  304

-continued
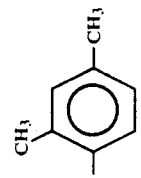 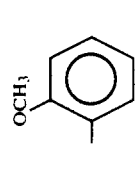 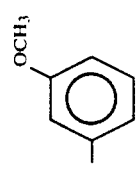 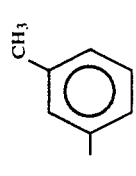 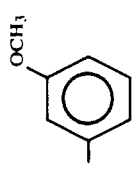
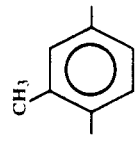 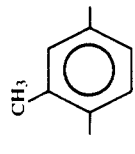 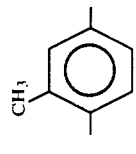 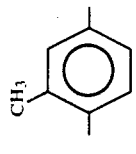 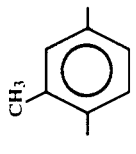 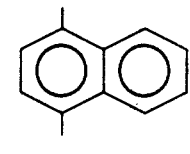
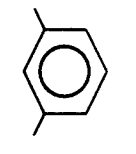 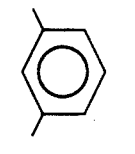 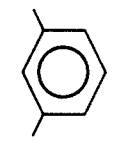 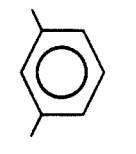 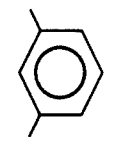 
| 312 | 313 | 314 | 315 | 316 | 317 |

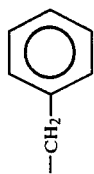 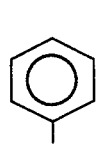 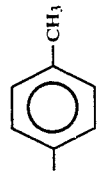 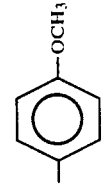 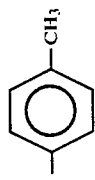
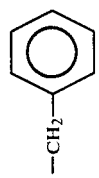 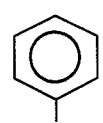 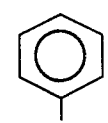 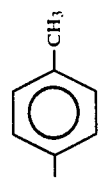
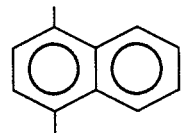 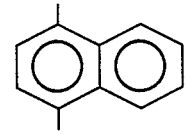 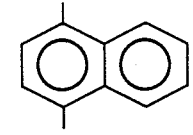 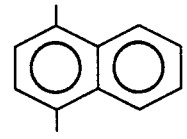
 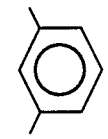  
| 318 | 319 | 320 | 321 | 322 |

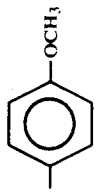 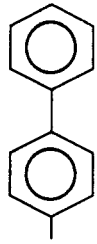 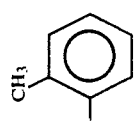 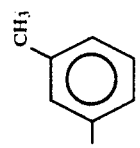 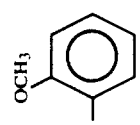
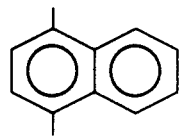 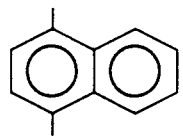 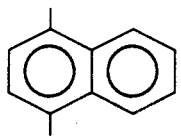 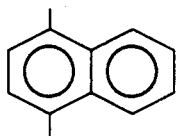 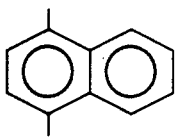
    
323   324   325   326   327

-continued
| 328 | 329 | 330 | 331 | 332 | 333 | 334 | 335 |
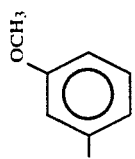 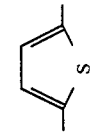 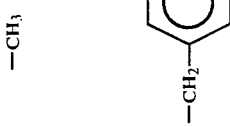 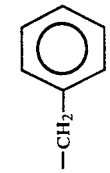 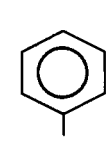 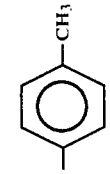 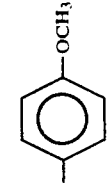 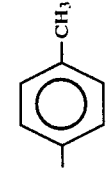 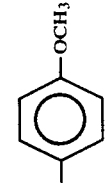
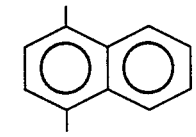 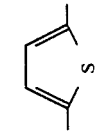 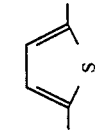 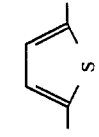 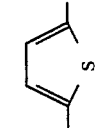 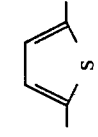 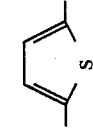

-continued
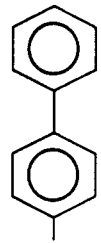 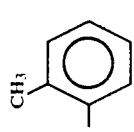 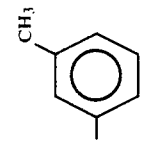 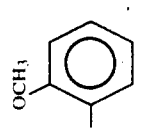 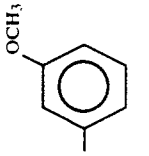 —CH₃  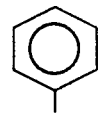
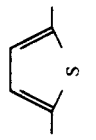 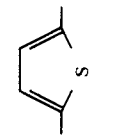 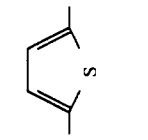 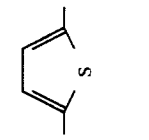 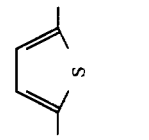 —CH₃ —CH₃ —CH₃
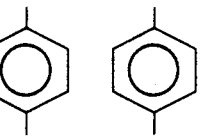 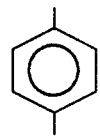
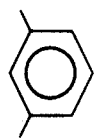 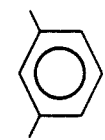 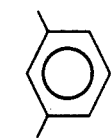 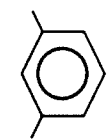 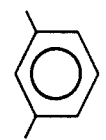 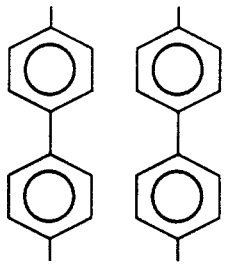 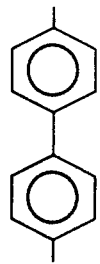
336　337　338　339　340　341　342　343

-continued
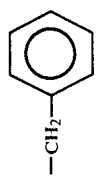  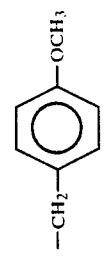 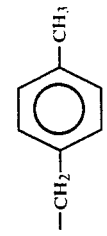 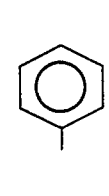 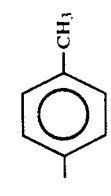 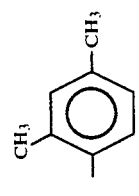 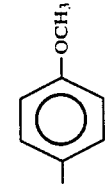 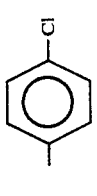
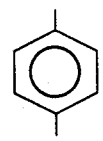 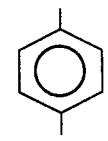 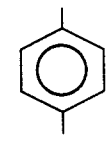 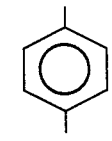 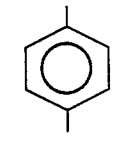 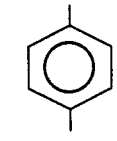 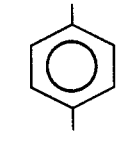 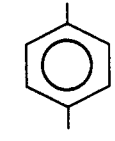 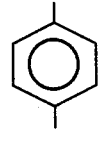
344  345  346  347  348  349  350  351  352

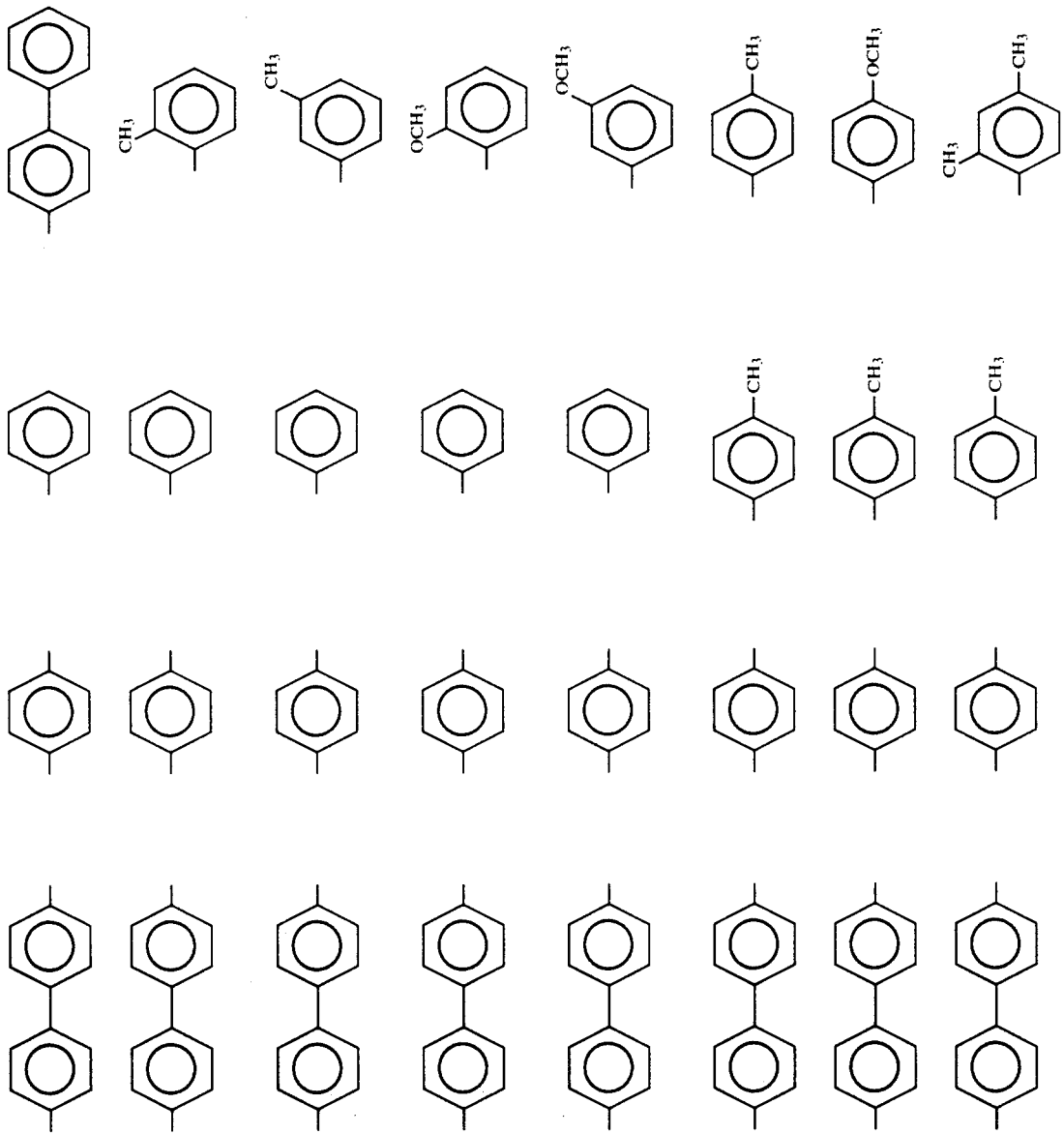

-continued
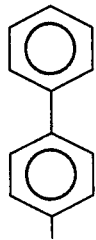 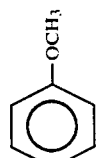 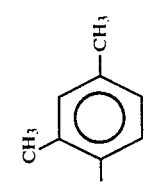 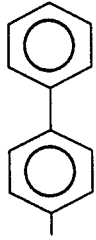 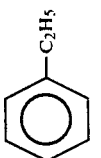 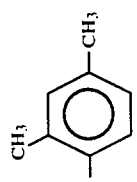 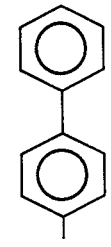 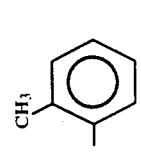
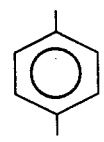 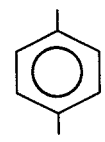 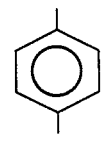 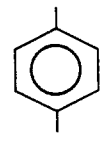 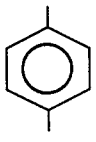 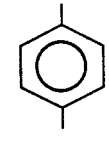 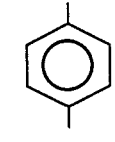
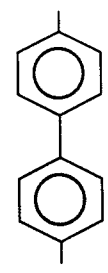 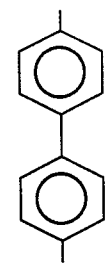 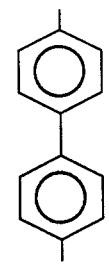 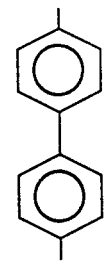 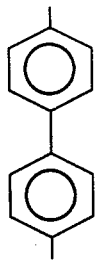 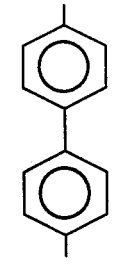 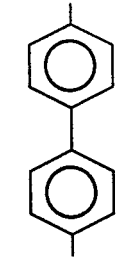
361  362  363  364  365  366  367  368

-continued
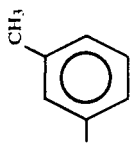 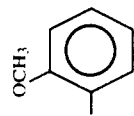 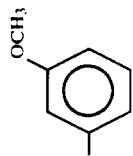  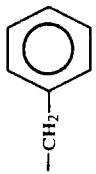  
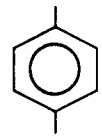 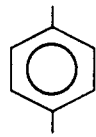 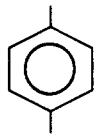 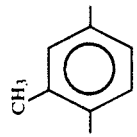 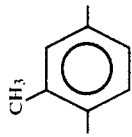 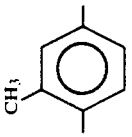 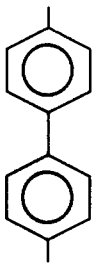
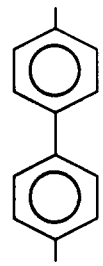 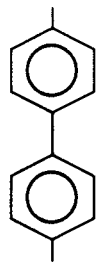 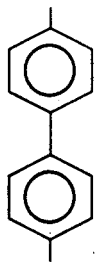 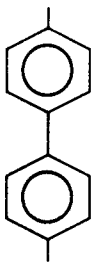 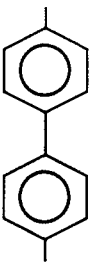
369  370  371  372  373  374  375

-continued
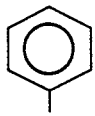 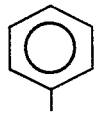 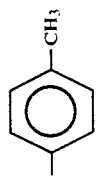 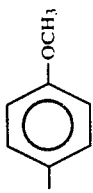 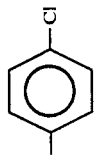 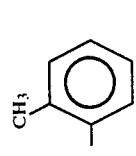 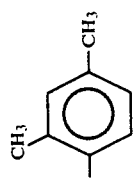
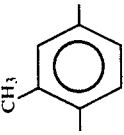 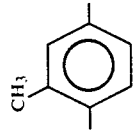 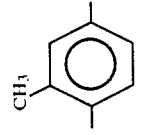 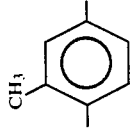 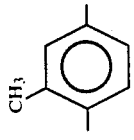 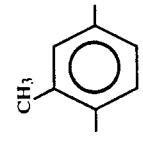
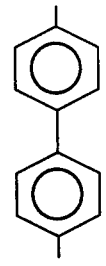 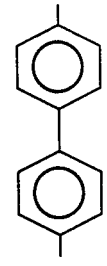 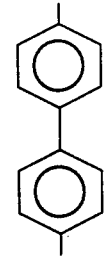 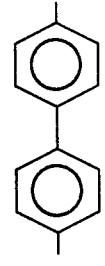 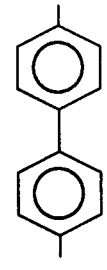 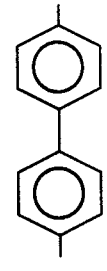 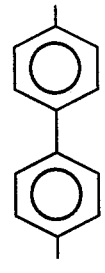
376  377  378  379  380  381  382

-continued
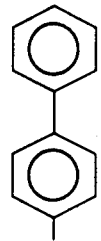 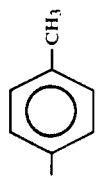 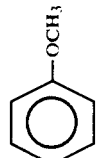 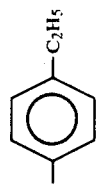 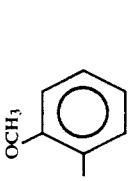 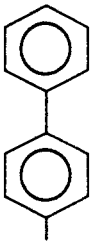 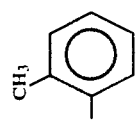
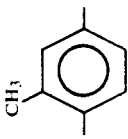 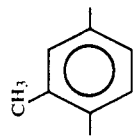 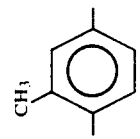 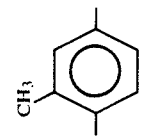 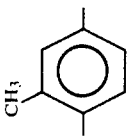 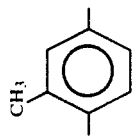 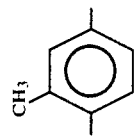
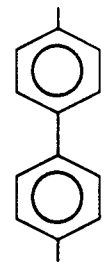 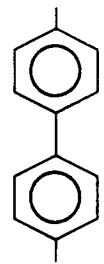 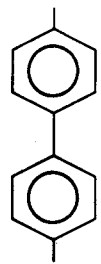 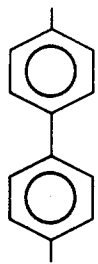 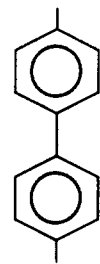 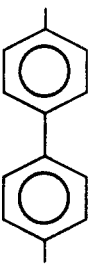 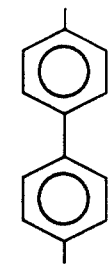
383    384    385    386    387    388    389

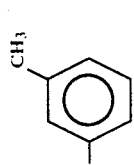 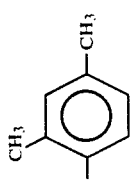 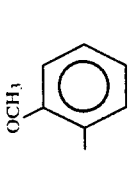 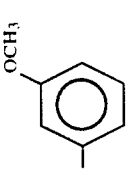 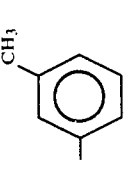 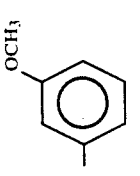
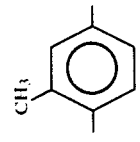 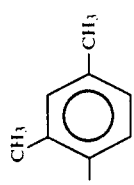 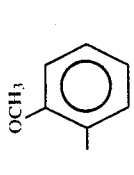 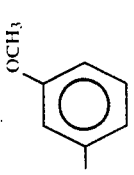 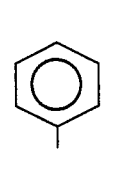 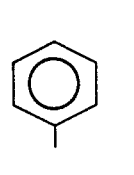 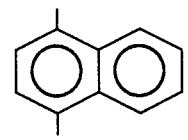
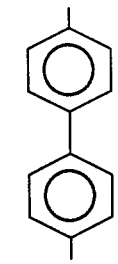 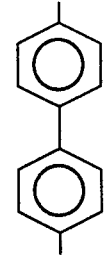

-continued
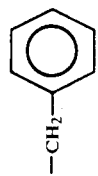 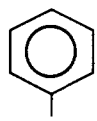 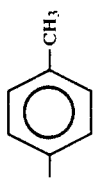 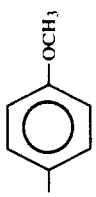 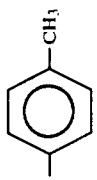
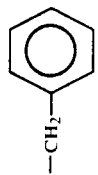 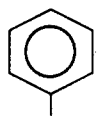 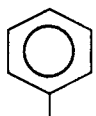 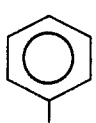 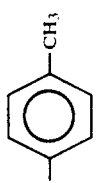
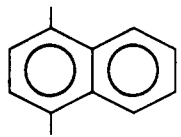 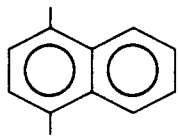 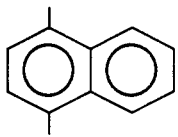 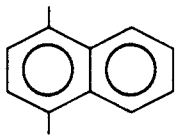 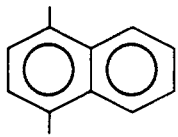
397 398 399 400 401

-continued
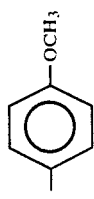 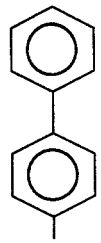 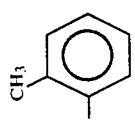 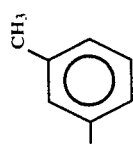 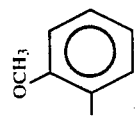
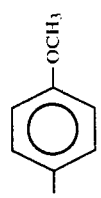 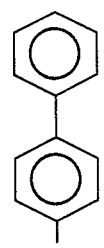 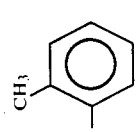 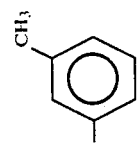
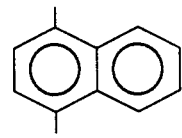 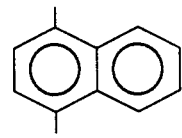 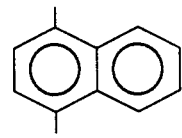 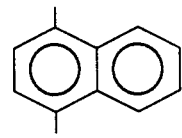 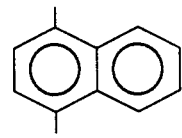
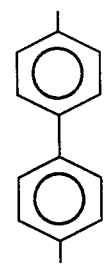 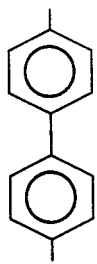 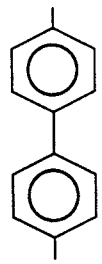 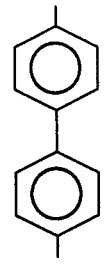 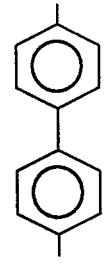
402 403 404 405 406

-continued
| 407 | 408 | 409 | 410 | 411 | 412 | 413 | 414 |
|---|---|---|---|---|---|---|---|
| 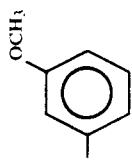 | —CH$_3$ | 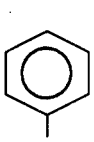 | 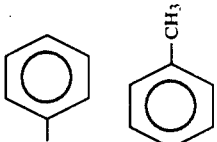 | 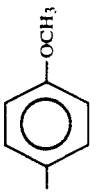 | 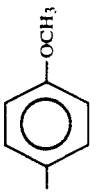 | 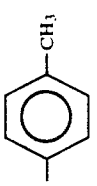 | 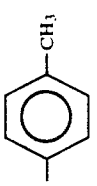 |
| 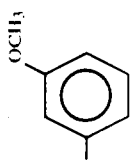 | —CH$_3$ | 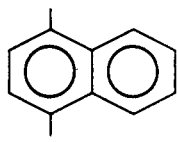 | 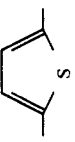 | 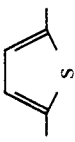 | 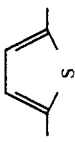 |  | 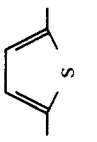 |
| 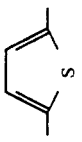 | 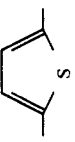 | 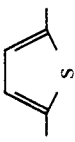 | 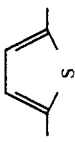 |  | 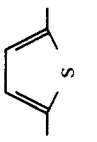 | 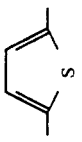 | 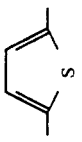 |
| 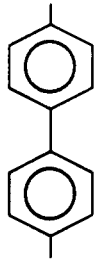 | 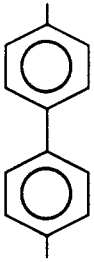 | 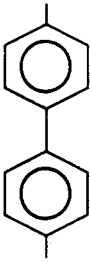 | 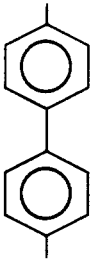 | 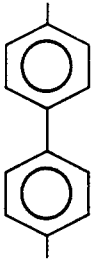 | 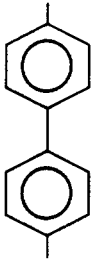 | 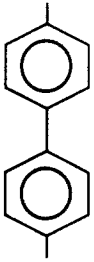 | 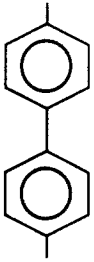 |

| | | | | | | |
|---|---|---|---|---|---|---|
| 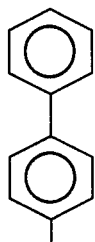 | 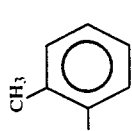 | 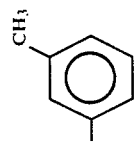 | 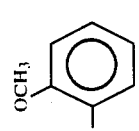 | 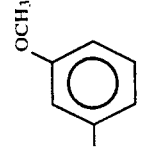 | —CH₃ | 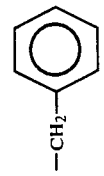 |
| 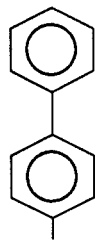 | 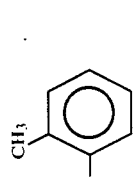 | 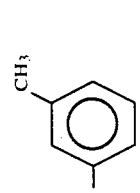 | 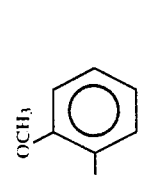 | 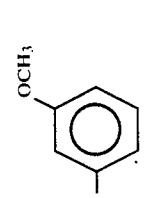 | —CH₃ | —CH₃ |
| 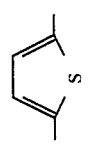 | 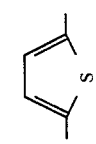 | 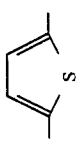 | 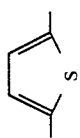 | 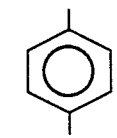 | 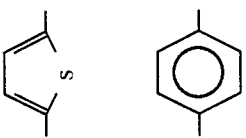 | |
| 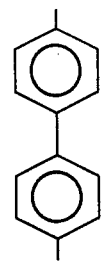 | 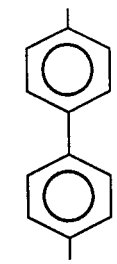 | 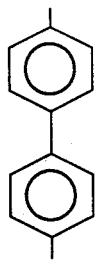 | 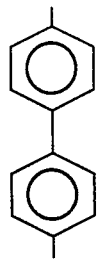 | 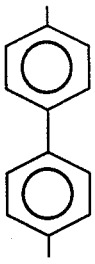 | 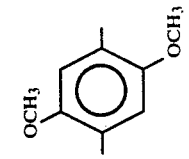 | 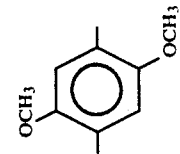 |
| 415 | 416 | 417 | 418 | 419 | 420 | 421 |

-continued —CH₃
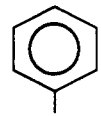  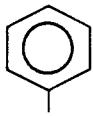 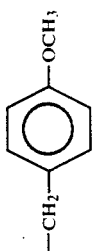 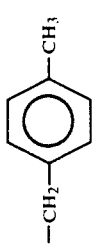 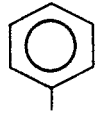
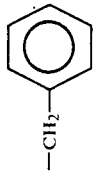
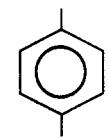 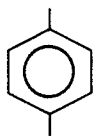 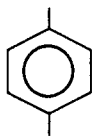 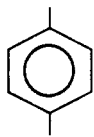 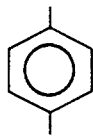 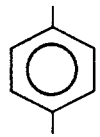
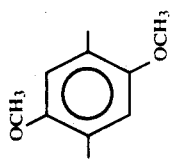 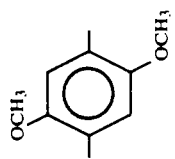 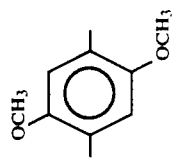 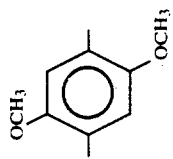 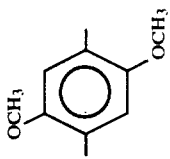 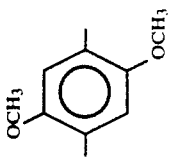
422    423    424    425    426    427

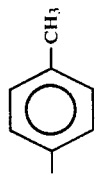 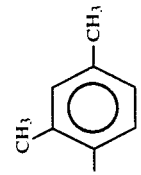 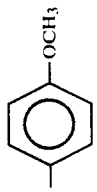 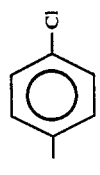 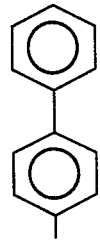
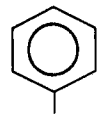 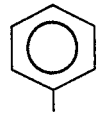 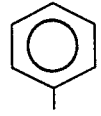 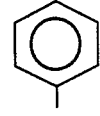 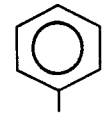
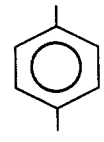 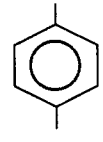 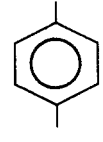 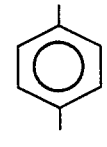 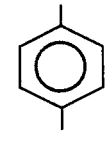
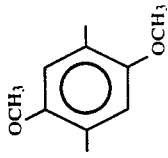 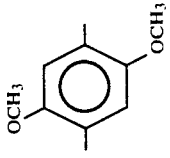 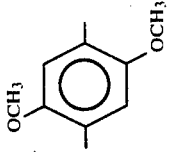 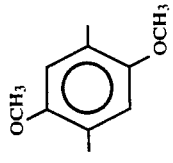 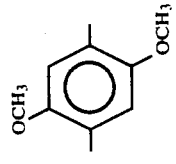
428　　　429　　　430　　　431　　　432

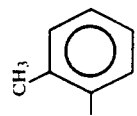 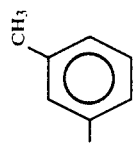 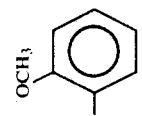 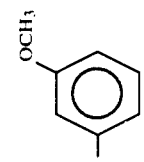 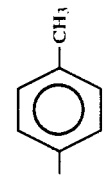 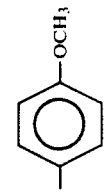
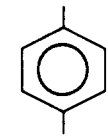 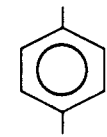 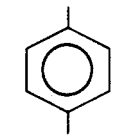 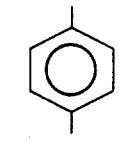 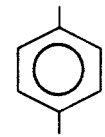 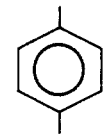
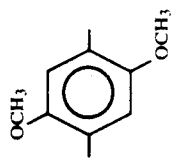 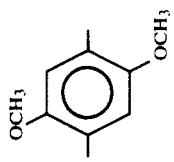 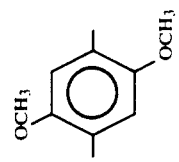 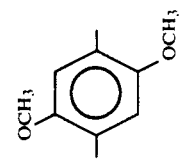 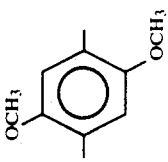 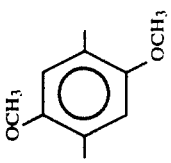
433     434     435     436     437     438

-continued
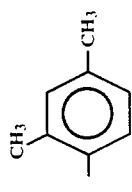 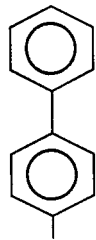 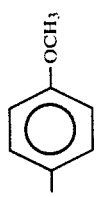 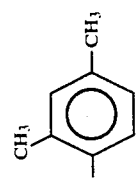 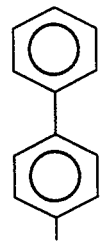
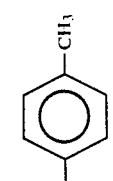 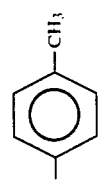 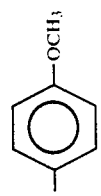 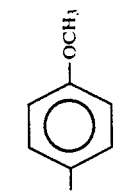 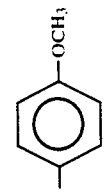
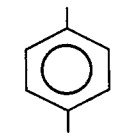 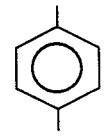 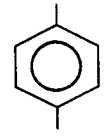 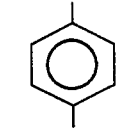 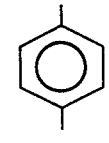
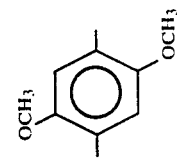 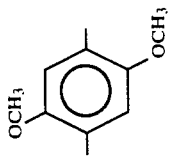 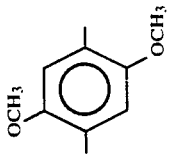 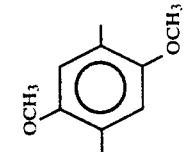 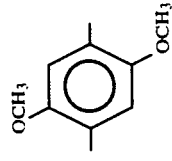
439　　440　　441　　442　　443

-continued
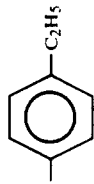 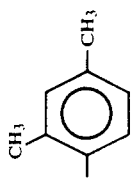 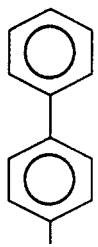
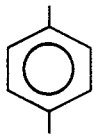 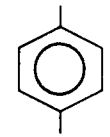 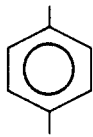
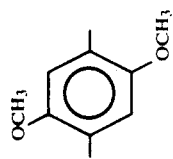 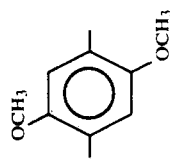 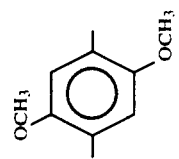
444     445     446

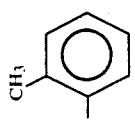 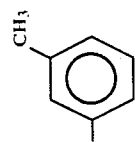 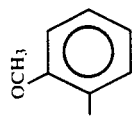 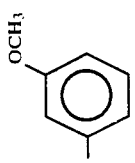 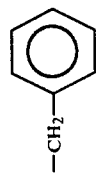 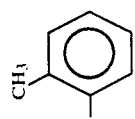
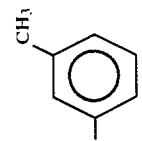 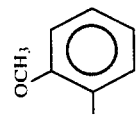 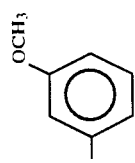 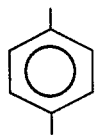 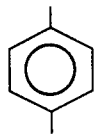 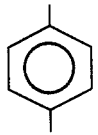
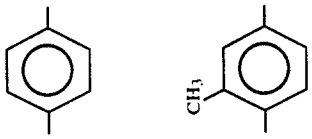 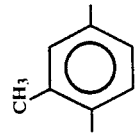 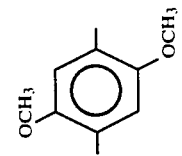 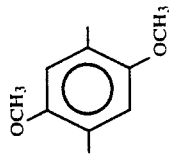 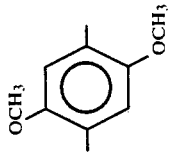 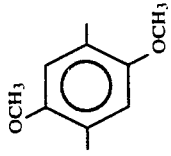 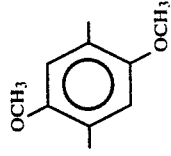 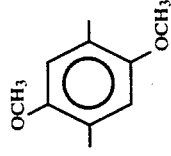
447     448     449     450     451     452

-continued
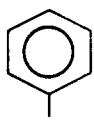 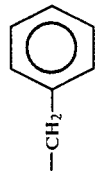 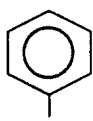 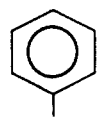 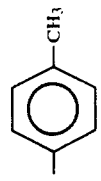
—CH₃ 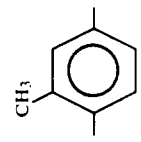 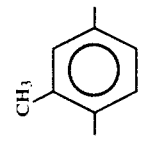 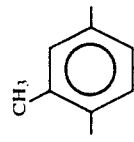 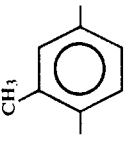
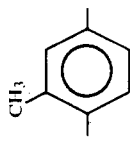 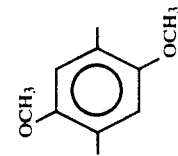 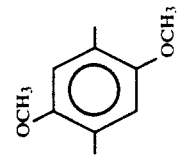 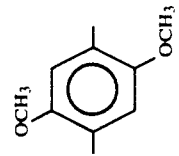 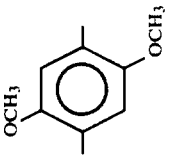
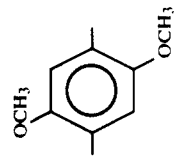 
453     454     455     456     457

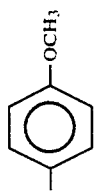 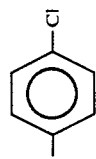 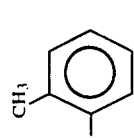 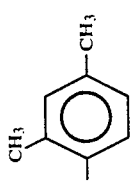 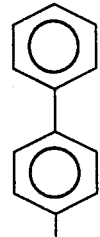 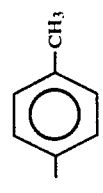
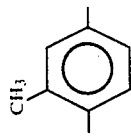 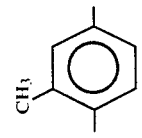 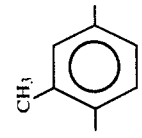 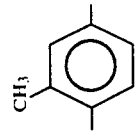 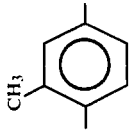 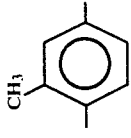
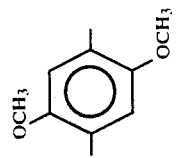 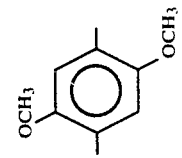 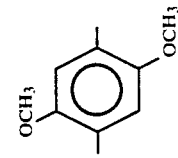 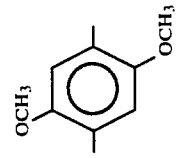 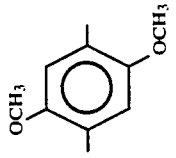 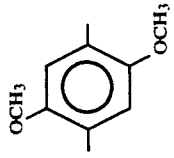
458 459 460 461 462 463

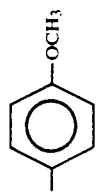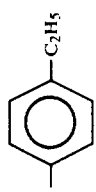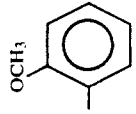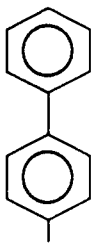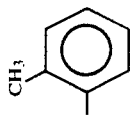
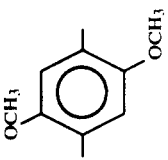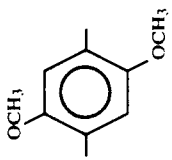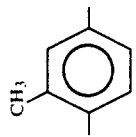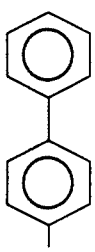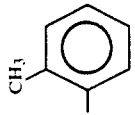
| 464 | 465 | 466 | 467 | 468 |

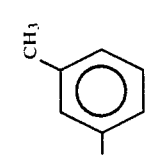 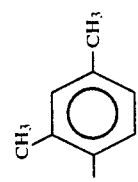 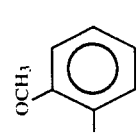 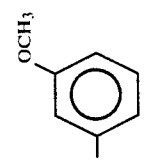 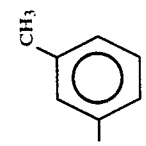 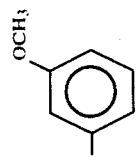
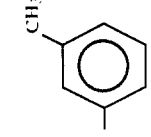 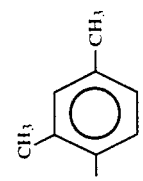 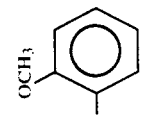 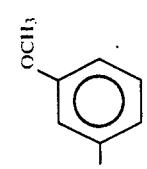 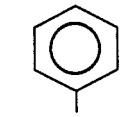 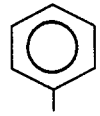
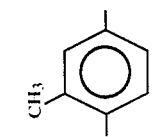 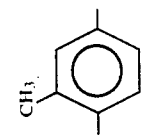 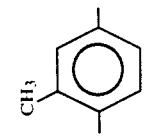 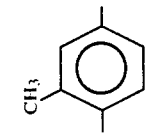 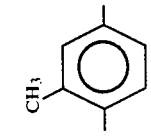 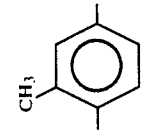
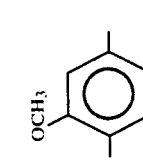 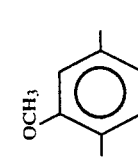 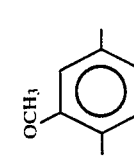 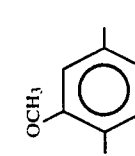 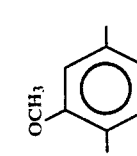 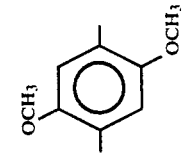
469     470     471     472     473     474

-continued
| | | | | |
|---|---|---|---|---|
| —CH$_3$ | 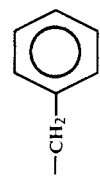 | 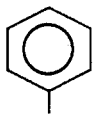 | 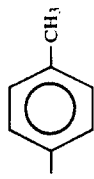 | 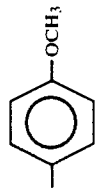 |
| —CH$_3$ | 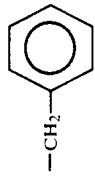 | 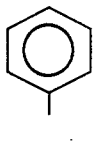 | 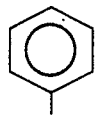 | 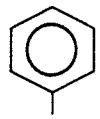 |
| 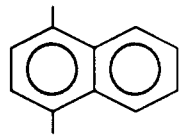 | 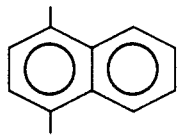 | 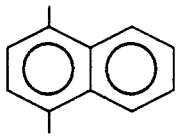 | 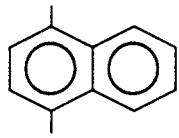 | 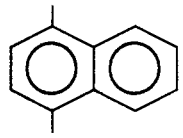 |
| 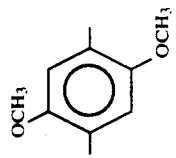 | 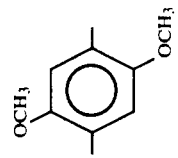 | 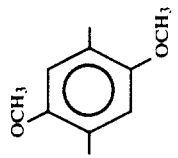 | 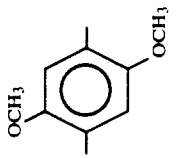 | 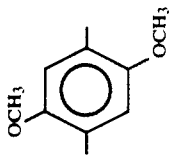 |
| 475 | 476 | 477 | 478 | 479 |

-continued
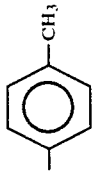 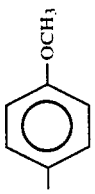 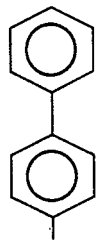 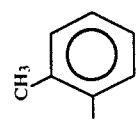 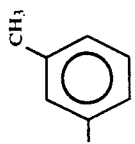
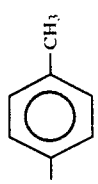 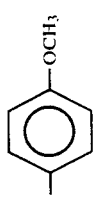 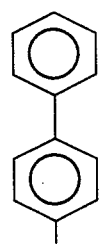 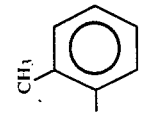 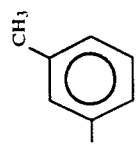
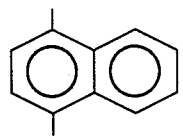 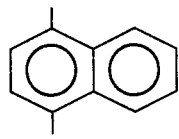 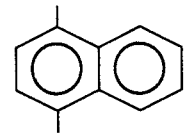 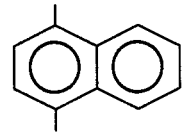 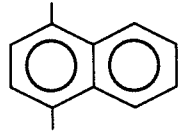
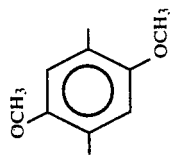 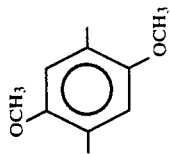 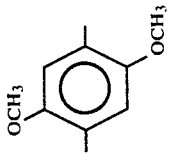 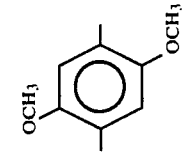 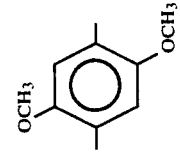
| 480 | 481 | 482 | 483 | 484 |

-continued
| | | | | |
|---|---|---|---|---|
| 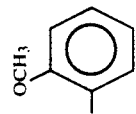 | 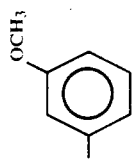 |  —CH₃ | 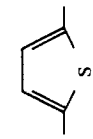 | 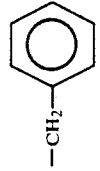 |
| 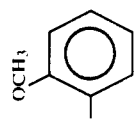 | 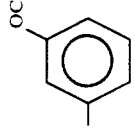 |  —CH₃ | 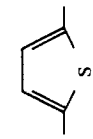 | 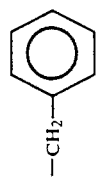 |
| | | | | |
| 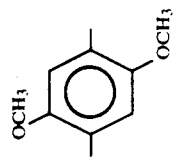 | 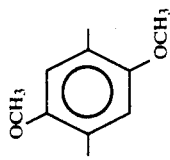 | 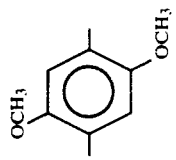 | 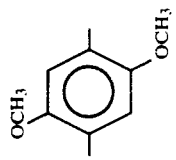 | 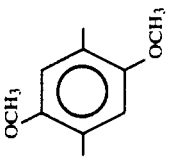 |
| 485 | 486 | 487 | 488 | 489 |

-continued
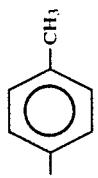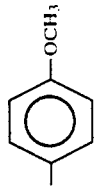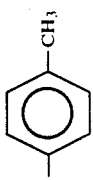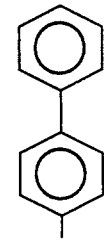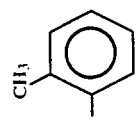
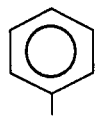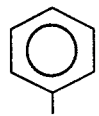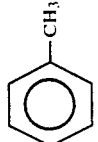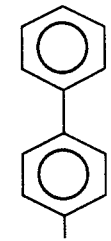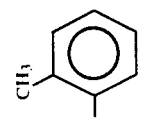
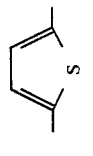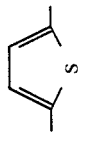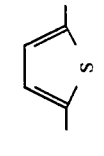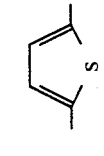
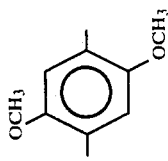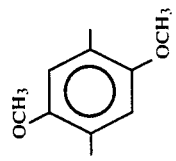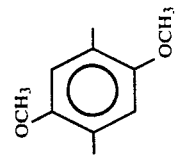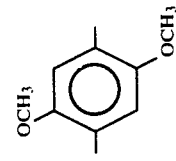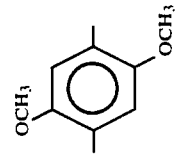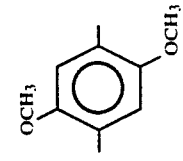
490    491    492    493    494    495

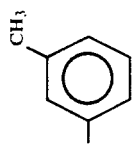 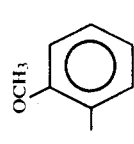 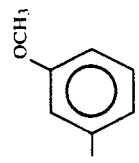  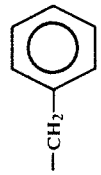
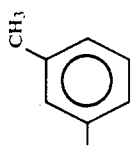 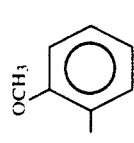 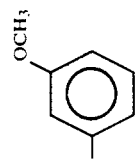 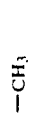 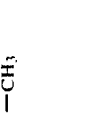
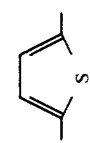 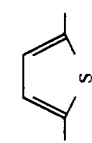 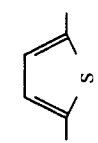 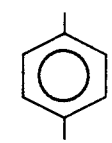 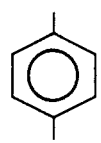
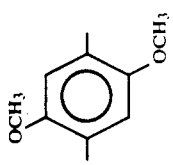 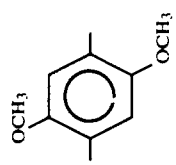 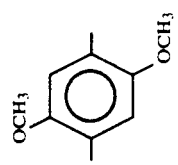 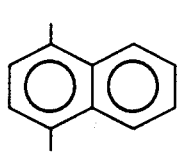 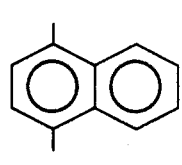
496    497    498    499    500

-continued
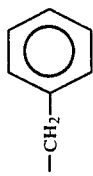 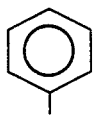 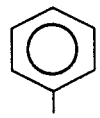 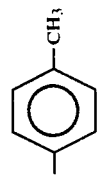 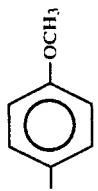
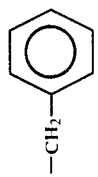 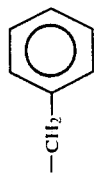 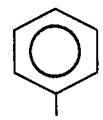 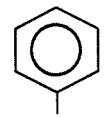 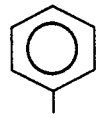
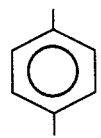 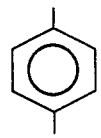 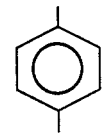 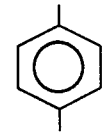 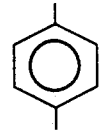
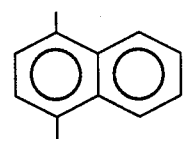 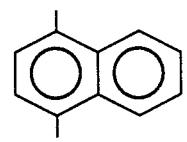 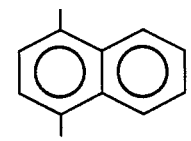 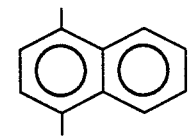 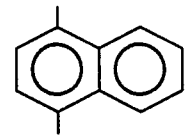
501　　　　502　　　　503　　　　504　　　　505

-continued
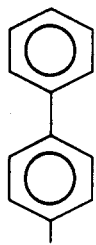 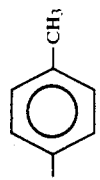 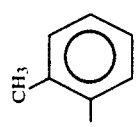 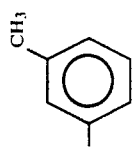 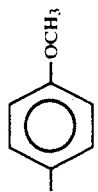
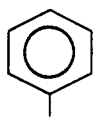 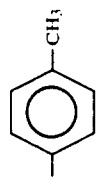 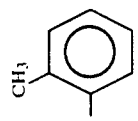 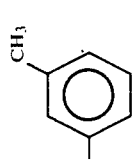 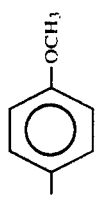
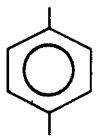 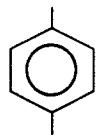 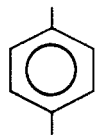 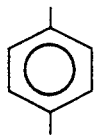 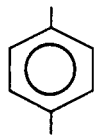
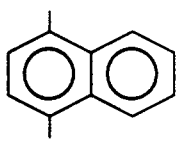 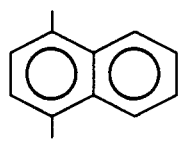 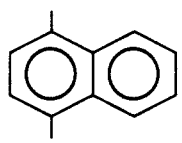 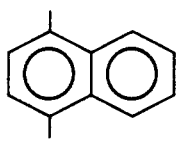 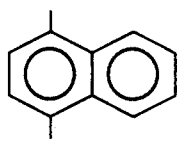
506    507    508    509    510

-continued
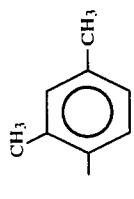 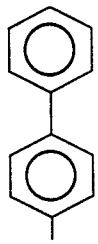 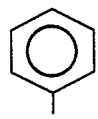 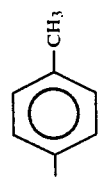 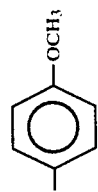
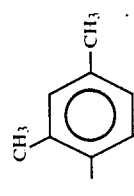 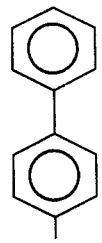 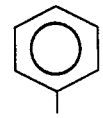 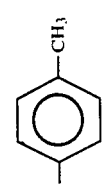 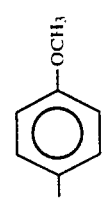
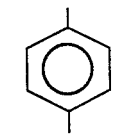 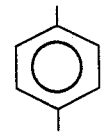 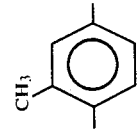 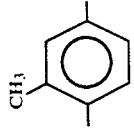 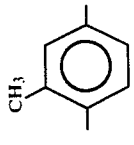
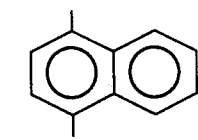 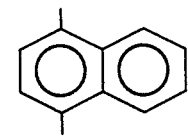 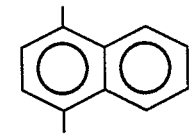 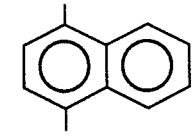 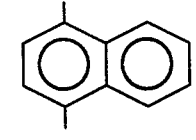
511    512    513    514    515

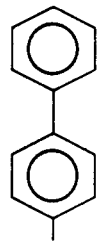 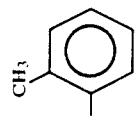 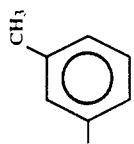 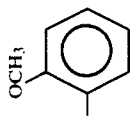 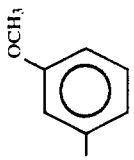
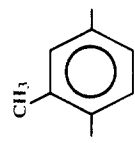 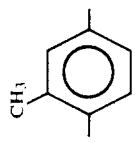 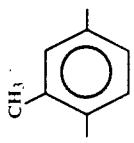 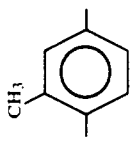 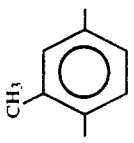
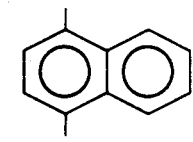 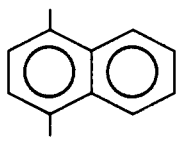 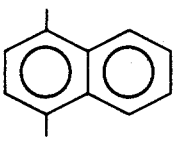 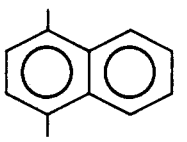 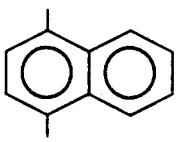
516     517     518     519     520

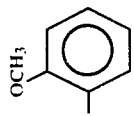 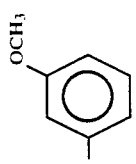 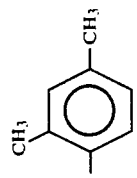 —CH$_3$
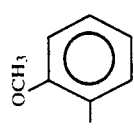 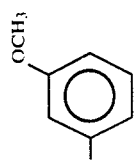 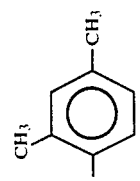 —CH$_3$
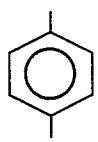 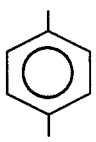 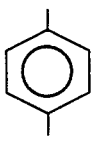 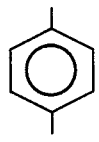
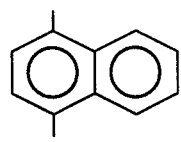 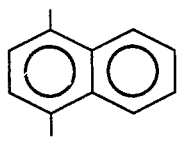 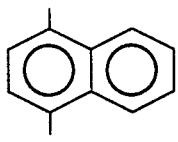 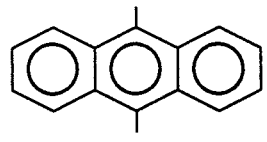
521     522     523     524

-continued
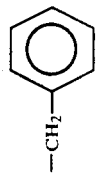
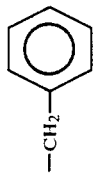
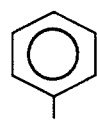
—CH₃
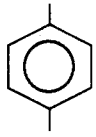
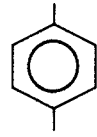
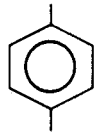
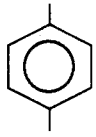
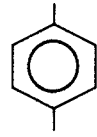
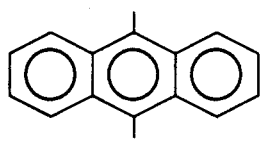
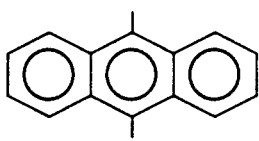
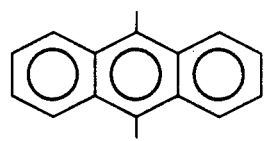
525
526
527

-continued
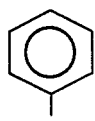 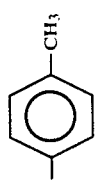 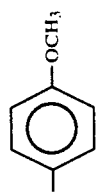
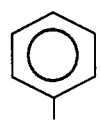 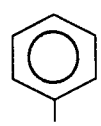 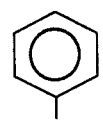
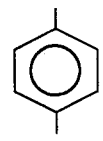 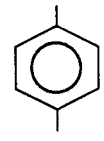 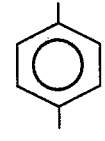
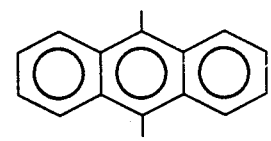 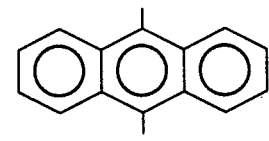 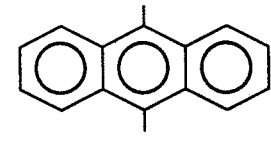
528     529     530

-continued
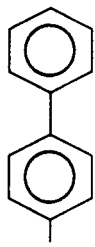 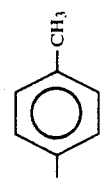 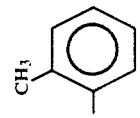
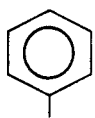 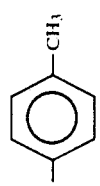 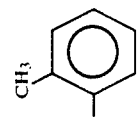
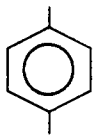 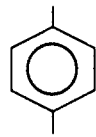 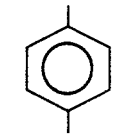
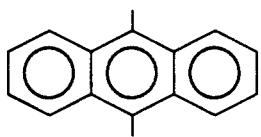 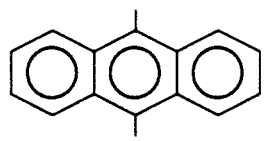 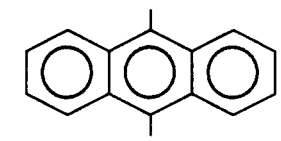
531 532 533

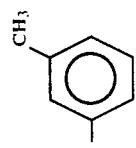 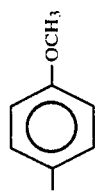 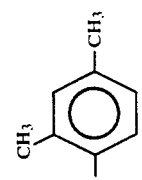
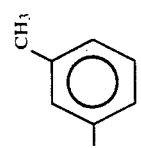 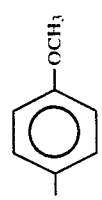 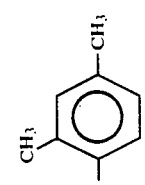
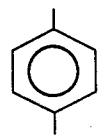 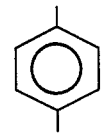 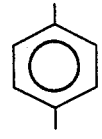
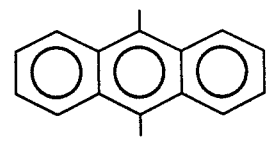 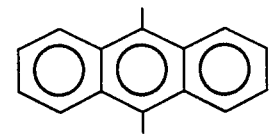 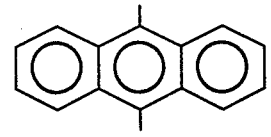
534         535         536

-continued
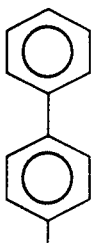 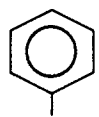 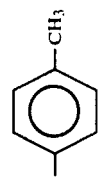
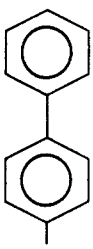 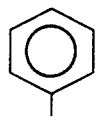 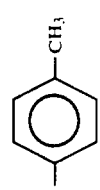
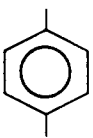 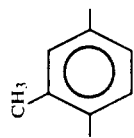 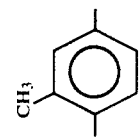
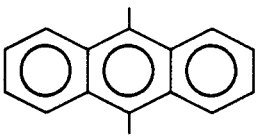 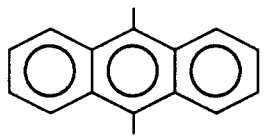 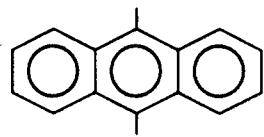
537      538      539

-continued
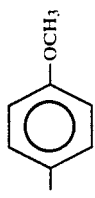 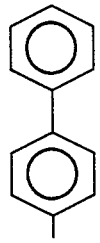 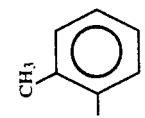
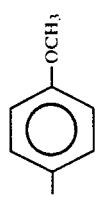 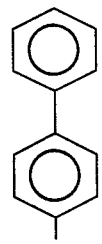 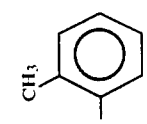
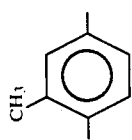 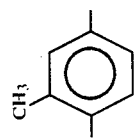 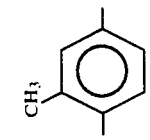
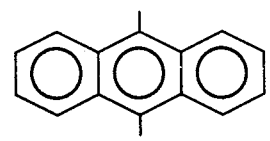 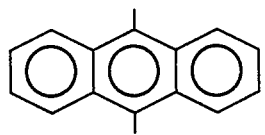 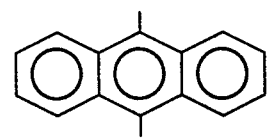
540 541 542

-continued
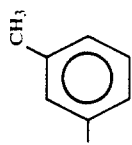 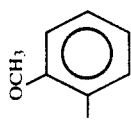 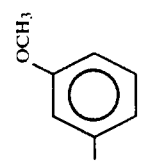
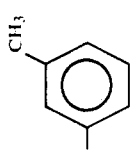 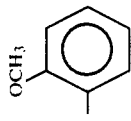 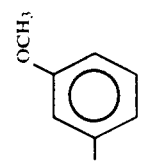
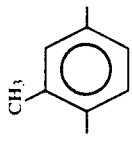 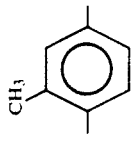 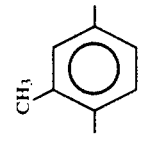
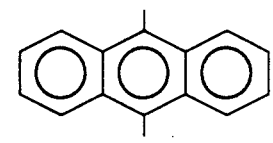 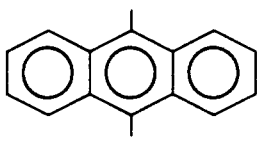 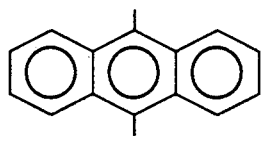
543 544 545

-continued
| | | | |
|---|---|---|---|
| 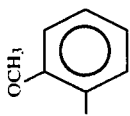 | 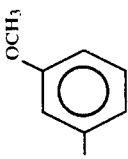 | 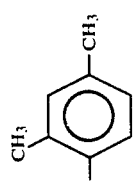 | —CH$_3$ |
| 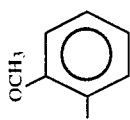 | 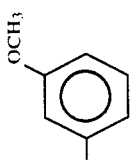 | 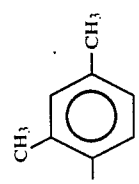 | —CH$_3$ |
| 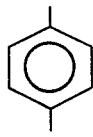 | 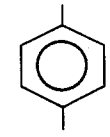 | 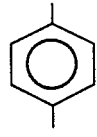 | 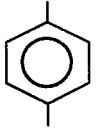 |
| 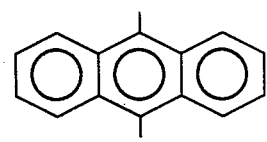 | 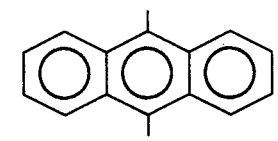 | 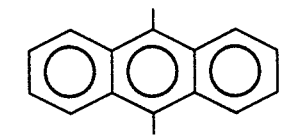 | 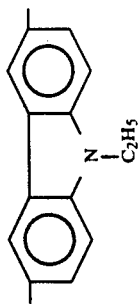 |
| 546 | 547 | 548 | 549 |

-continued
—CH₃
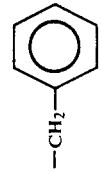 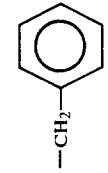 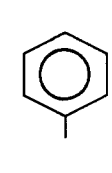 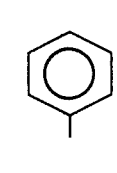 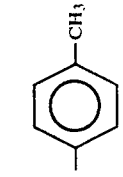 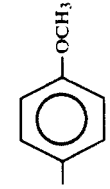
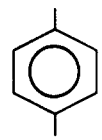 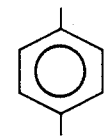 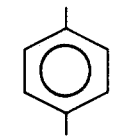 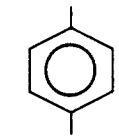 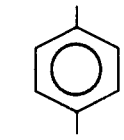 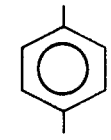
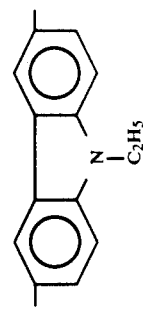 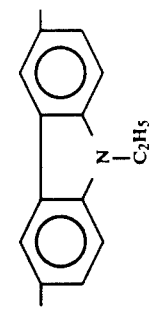 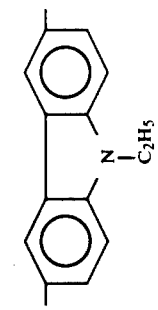 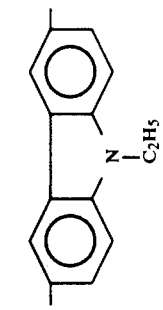 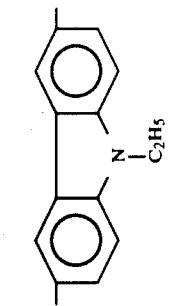 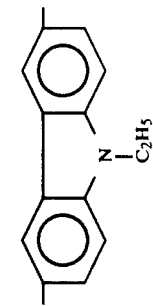
550    551    552    553    554    555

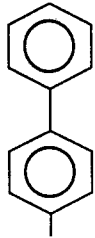 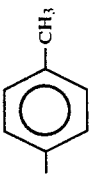 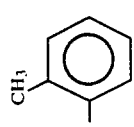 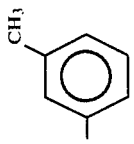 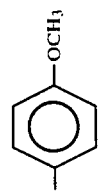 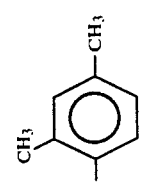
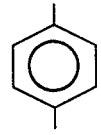 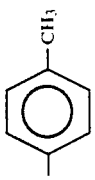 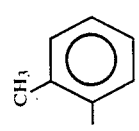 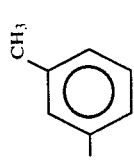 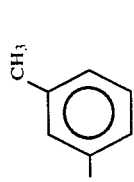 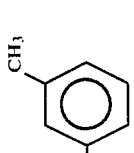 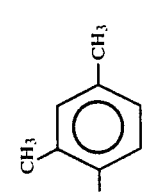
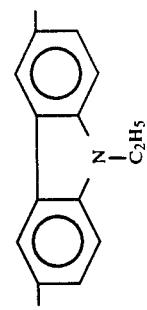 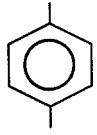 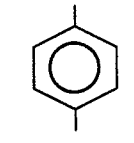
556  557  558  559  560  561

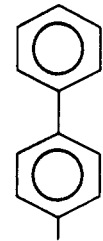 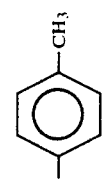 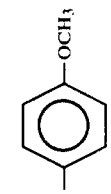 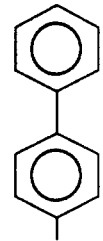 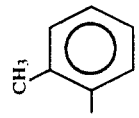
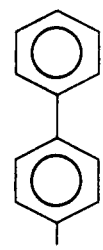 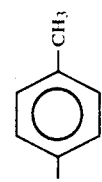 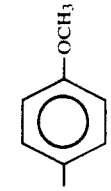 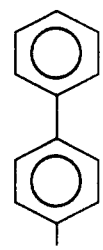
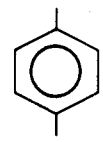 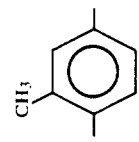 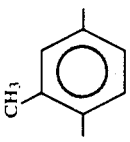 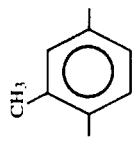 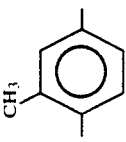
562   563   564   565   566   567

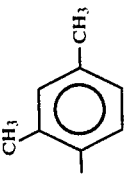 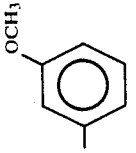 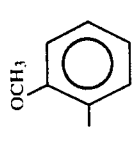 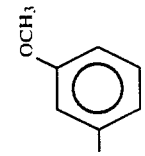 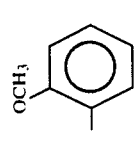 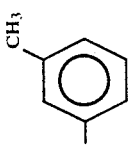
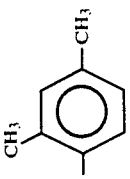 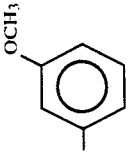 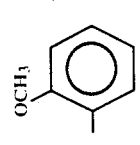 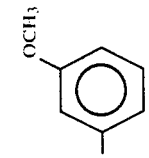 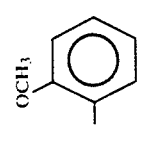 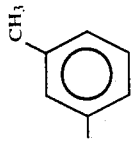
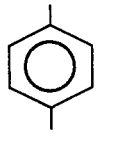 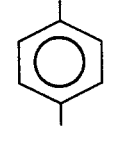 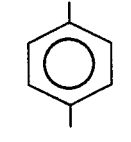 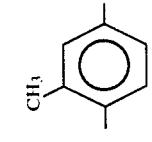 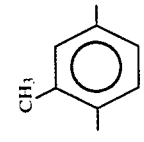 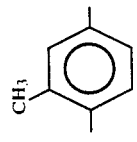
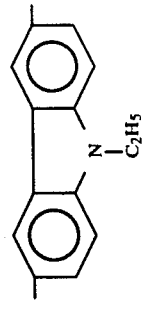 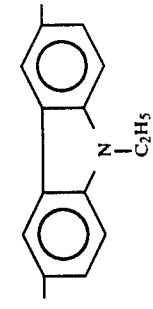 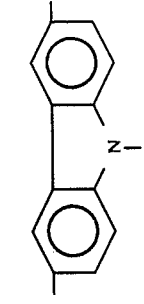 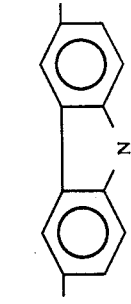 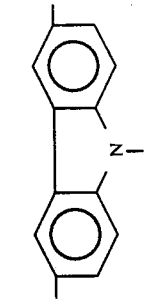 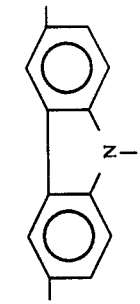
573  572  571  570  569  568

| | | | | |
|---|---|---|---|---|
| 574 | 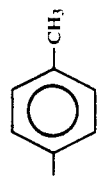 | 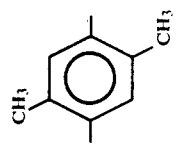 | | |
| 575 | 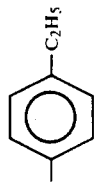 | 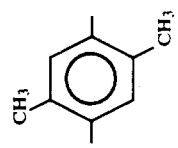 | | |
| 576 | 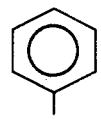 | 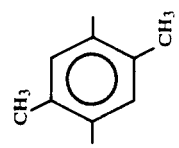 | | |
| 577 | 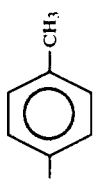 | 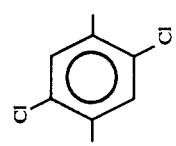 | | |
| 578 | 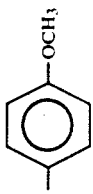 | 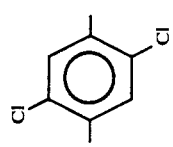 | | |

In the photoconductors according to the present invention, at least one aromatic diethyl compound of the formula (III) is contained in the photoconductive layers 2a, 2b, 2c, 2d and 2e. The aromatic diethyl compounds can be employed in different ways, for example, as shown in FIG. 12, FIG. 13, FIG. 14, FIG. 15 and FIG. 16.

Figure 12:
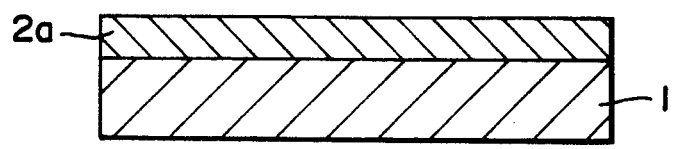
FIGS. 12 to 16 are enlarged schematic illustrations of embodiments of an electrophotographic photoconductor according to the present invention.

In the photoconductor as shown in FIG. 12, a photoconductive layer 2a is formed on an electroconductive support 1, which photoconductive layer 2a comprises a aromatic diethyl compound, a sensitizer dye and a binder agent. In this photoconductor, the aromatic diethyl compound works as a photoconductive material, through which charge carriers which are necessary for the light decay of the photoconductor are generated and transported. However, the aromatic diethyl compound itself scarcely absorbs light in the visible light range and, therefore, it is necessary to add a sensitizer dye which absorbs light in the visible light range in order to form latent electrostatic images by use of visible light.

Figure 13:
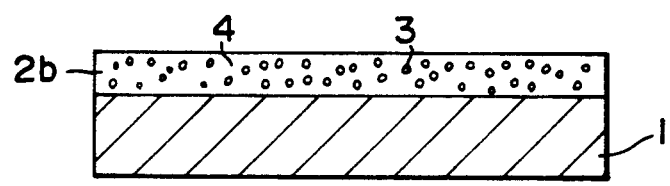

Referring to FIG. 13, there is shown an enlarged cross-sectional view of another embodiment of an electrophotographic photoconductor according to the present invention In the figure, reference numeral 1 indicates an electroconductive support. On the electroconductive support 1, there is formed a photoconductive layer 2b comprising a charge generating material 3 dispersed in a charge transporting medium 4 comprising an aromatic diethyl compound and a binder agent. In this embodiment, the aromatic diethyl compound works as a charge transporting material; and the aromatic diethyl compound and the binder agent in combination constitute the charge transporting medium 4. The charge generating material 3, which is, for example, an inorganic or organic pigment, generates charge carriers. The charge transporting medium 4 accepts the charge carriers generated by the charge generating material 3 and transports those charge carriers.

In this electrophotographic photoconductor, it is basically necessary that the light-absorption wavelength regions of the charge generating material 3 and the aromatic diethyl compound not overlap in the visible light range. This is because, in order that the charge generating material 3 produce charge carriers efficiently, it is necessary that light pass through the charge transporting medium 4 and reach the surface of the charge generating material 3. Since the aromatic diethyl compound of the above described general formula do not substantially absorb light in the visible range, they can work effectively as charge transporting materials in combination with the charge generating material 3 which absorbs the light in the visible region and generates charge carriers.

Figure 14:
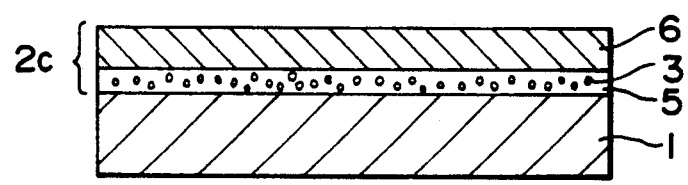

Referring to FIG. 14, there is shown an enlarged cross-sectional view of a further embodiment of an electrophotographic photoconductor according to the present invention. In the figure, there is formed on the electroconductive support 1 a two-layered photoconductive layer 2c comprising a charge generating layer 5 consisting essentially of the charge generating material 3, and a charge transporting layer 6 containing an aromatic diethyl compound of the previously described formula (III).

In this photoconductor, light which has passed through the charge transporting layer 6 reaches the charge generating layer 5, and charge carriers are generated within the charge generating layer 5. The charge carriers which are necessary for the light decay for latent electrostatic image formation are generated by the charge generating material 3, accepted and transported by the charge transporting layer 6. In the charge transporting layer 6, the aromatic diethyl compound mainly works for transporting charge carriers. The generation and transportation of the charge carriers are performed by the same mechanism as that in the photoconductor shown in FIG. 13.

Figure 15:
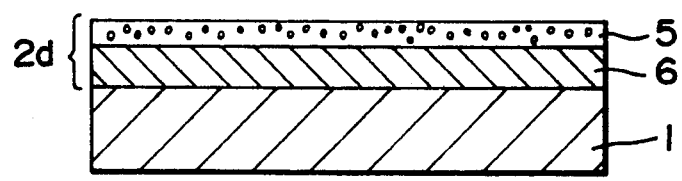

The electrophotographic photoconductor shown in FIG. 15, the charge generating layer 5 is formed on the charge transporting layer 5 containing the aromatic diethyl compound in the photoconductive layer 2d, thus the overlaying order of the charge generating layer 5 and the charge transporting layer 6 is reversed as compared with the electrophotographic photoconductor as shown in FIG. 14. The mechanism of the generation and transportation of charge carriers is substantially the same as that of the photoconductor shown in FIG. 14.

Figure 16:
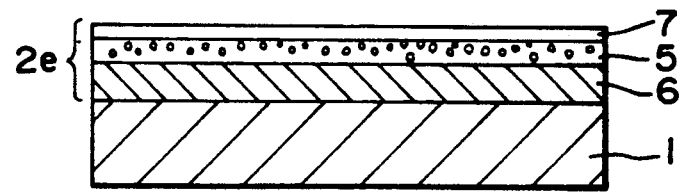

In the above photoconductor, a protective layer 7 may be formed on the charge generating layer 5 as shown in FIG. 16 for protecting the charge generating layer 5.

When an electrophotographic photoconductor according to the present invention as shown in FIG. 12 is prepared, at least one aromatic diethyl compound of the previously described formula (III) is dispersed in a binder resin solution, and a sensitizer dye is then added to the mixture, so that a photoconductive layer coating liquid is prepared. The thus prepared photoconductive layer coating liquid is coated on an electroconductive support 1 and dried, so that a photoconductive layer 2a is formed on the electroconductive support 1.

It is preferable that the thickness of the photosensitive layer 2a be in the range of 3 μm to 50 μm, more preferably in the range of 5 μm to 20 μm. It is preferable that the amount of the aromatic diethyl compound contained in the photoconductive layer 2a be in the range of 30 wt. % to 70 wt. % of the total weight of the photoconductive layer 2a, more preferably about 50 wt. % of the total weight of the photoconductive layer 2a. Further, it is preferable that the amount of the sensitizer dye contained in the photoconductive layer 2a be in the range of 0.1 wt. % to 5 wt. % of the total weight of the photoconductive layer 2a, more preferably in the range of 0.5 wt. % to 3 wt. %, of the total weight of the photoconductive layer 2a.

As the sensitizer dye, the following can be employed in the present invention: Triarylmethane dyes, such as Brilliant Green, Victoria Blue B, Methyl Violet, Crystal Violet, and Acid Violet 6B; xanthene dyes, such as Rhodamine B, Rhodamine 6G, Rhodamine G Extra, Eosin S, Erythrosin, Rose Bengale, and Fluorescein; thiazine dyes, such as Methylene Blue; cyanin dyes, such as cyanin; and pyrylium dyes, such as 2,6-diphenyl-4-(N,N-dimethylaminophenyl) thiapyrylium perchlorate and benzopyrylium salt (Japanese Patent Publication 48-25658). These sensitizer dyes can be used alone or in combination.

An electrophotographic photoconductor according to the present invention as shown in FIG. 13 can be prepared, for example, as follows. A charge generating material in the form of small particles is dispersed in a solution of one or more aromatic diethyl compound and a binder agent. The thus prepared dispersion is coated on the electroconductive support 1 and then dried, whereby a photoconductive layer 2b is formed on the electroconductive support 1.

It is preferable that the thickness of the photoconductive layer 2b be in the range of 3 μm to 50 μm, more preferably in the range of 5 μm to 20 μm. It is preferable that the amount of the aromatic diethyl compound contained in the photoconductive layer 2b be in the range of 10 wt. % to 95 wt. % of the total weight of the photoconductive layer 2b. Further, it is preferable that the amount of the charge generating material 3 contained in the photoconductive layer 2b be in the range of 0.1 wt. % to 50 wt. %, more preferably in the range of 1 wt. % to 20 wt. %, of the total weight of the photoconductive layer 2b.

As the charge generating material 3, the following can be employed in the present invention: Inorganic pigments, such as selenium, a selenium-tellurium alloy, cadmium sulfide, a cadmium sulfide-selenium alloy, and α-silicon; and organic pigments, for example, C.I. Pigment Blue 25 (C.I. 21180), C.I. Pigment Red 41 (C.I. 21200), C.I. Acid Red 52 (C.I. 45100), and C.I. Basic Red 3 (C.I. 45210); azo pigments having a carbazole skeleton (Japanese Laid-Open Patent Application 53-95033), azo pigments having a distyrylbenzene skeleton (Japanese Laid-Open Patent Application 53-133445), azo pigments having a triphenylamine skeleton (Japanese Laid-Open Patent Application 53-132347), azo pigments having a dibenzothiophene skeleton (Japanese Laid-Open Patent Application 54-21728), azo pigments having an oxazole skeleton (Japanese Laid-Open Patent Application 54-12742), azo pigments having a fluorenone skeleton (Japanese Laid-Open Patent Application 54-22834), azo pigments having a bisstilbene skeleton (Japanese Laid-Open Patent Application 54-17733), azo pigments having a distyryl oxadiazole skeleton (Japanese Laid-Open Patent Application 54-2129), azo pigments having a distyryl carbazole skeleton (Japanese Laid-Open Patent Application 54-14967); phthalocyanine-type pigments such as C.I. Pigment Blue 16 (C.I. 74100); Indigo-type pigments such as C.I. Vat Brown 5 (C.I. 73410) and C.I. Vat Dye (C.I. 73030); and perylene-type pigments, such as Algo Scarlet B (made by Bayer Co., Ltd.) and Indanthrene Scarlet R (made by Bayer Co., Ltd). These charge generating materials can be used alone or in combination.

An electrophotographic photoconductor according to the present invention as shown in FIG. 14 can be prepared, for example, as follows. A charge generating material 3 is vacuum-evaporated on the electroconductive support 1, whereby a charge generating layer 5 is formed. Alternatively, a charge generating material 3 in the form of fine particles is dispersed in a solution of a binder agent, and this dispersion is applied to the electroconductive support material 1 and then dried, and, if necessary, the applied layer is subjected to buffing to make the surface smooth or to adjust the thickness of the layer to a predetermined thickness, whereby a charge generating layer 5 is formed. A charge transporting layer 6 is then formed on the charge generating layer 5 by applying a solution of one or more aromatic diethyl compounds and a binder agent to the charge generating layer 5 and then drying the applied solution. In this photoconductor, the charge generating material employed is the same as that employed in the photoconductor shown in FIG. 13.

It is preferable that the thickness of the charge generating layer 5 be 5 μm or less, more preferably 2 μm or less. It is preferable that the thickness of the charge transporting layer 6 be in the range of 3 μm to 50 μm, more preferably in the range of 5 μm to 20 μm. In the case where the charge generating layer 5 comprises a charge generating material in the form of fine particles, dispersed in a binder agent, it is preferable that the amount of the charge generating material in the charge generating layer 5 be in the range of 10 wt. % to 95 wt. % of the entire weight of the charge generating layer 5, more preferably in the range of about 50 wt. % to 90 wt. %. Further, it is preferable that the amount of the aromatic diethyl compound contained in the charge transporting layer 6 be in the range of 10 wt. % to 95 wt. %, more preferably in the range of 30 wt. % to 90 wt. % of the total weight of the charge transporting layer 6.

The electrophotographic photoconductor as shown in FIG. 15 can be prepared, for example, by coating a solution of a aromatic diethyl compound and a binder agent on the electroconductive support 1 and drying the same to form a charge transporting layer 4, and then coating on the charge transporting layer 4 a dispersion of finely-divided charge generating material, with addition thereto of a binder agent when necessary, and drying the coated dispersion to form a charge generating layer 5 on the charge transporting layer 4. The thickness of each of the two layers 4 and 5 and the compositions thereof may be the same as those of the photoconductive layer 2c in the photoconductor shown in FIG. 14.

When a protective layer 6 is formed on the charge generating layer 5 of the photoconductive layer by coating an appropriate resin solution, for instance, by performing spray coating, the photoconductor as shown in FIG. 16 can be prepared.

As the electroconductive support 1 for use in the present invention, a metal plate or metal foil, for example, made of aluminum, a plastic film on which a metal, for example, aluminum, is evaporated, or paper which has been treated so as to be electroconductive, can be employed.

As the binder agent for use in the present invention, condensation resins, such as polyamide, polyurethane polyester, epoxy resin, polyketone and polycarbonate; and vinyl polymers such as polyvinylketone, polystyrene, poly-N-vinylcarbazole and polyacrylamide, can be used. These resins can also be employed as a resin component in the above mentioned protective layer 7.

Other conventional electrically insulating and adhesive resins can also be used as the binder agent in the present invention. When necessary, there can be added to the binder resins a plasticizer, for example, halogenated paraffin, polybiphenyl chloride, dimethylnaphthalene and dibutyl phthalate.

In the above described photoconductors according to the present invention, if necessary, an adhesive or barrier layer can be interposed between the electroconductive support and the photoconductive layer. The adhesive layer or the barrier layer can be made of, for example, polyamide, nitrocellulose, or aluminum oxide. It is preferable that the thickness of the adhesive layer or barrier layer be 1 μm or less.

When copying is performed by use of the photoconductors according to the present invention, the surface of the photoconductor is charged uniformly in the dark to a predetermined polarity. The uniformly charged photoconductor is exposed to a light image so that a latent electrostatic image is formed on the photoconductor. The thus formed latent electrostatic image is developed by a developer to a visible image, and, when necessary, the developed image can be transferred to a sheet of paper. The photoconductors according to the present invention have high photosensitivity and excellent flexibility.

Preparation of embodiments of an electrophotographic photoconductor according to the present invention will now be explained in detail by referring to the following examples.

EXAMPLE P-1

The following components were ground and dispersed in a ball mill to prepare a charge generating layer coating liquid:

| | Parts by Weight |
|---|---|
| Diane Blue (C.I. Pigment Blue 25, C.I. 21180) (a charge generating pigment of the following formula (CG-1)) | 76 |

(CG-1 structural formula: diazo compound with HNOC, OH, H₃CO, OCH₃, HO, CONH substituents and N=N linkages)

| | |
|---|---|
| 2% tetrahydrofuran solution of a polyester resin (Vylon 200 made by Toyobo Co., Ltd.) | 1,260 |
| Tetrahydrofuran | 3,700 |

This charge generating layer coating liquid was coated by a doctor blade on the aluminum-evaporated surface of an aluminum-evaporated polyester base film, which served as an electroconductive support, so that a charge generating layer was formed on the electroconductive support with a thickness of about 1 μm when dried at room temperature.

Then the following components were mixed and dissolved, so that a charge transporting layer coating liquid was prepared:

| | Parts by Weight |
|---|---|
| Aromatic diethyl compound No. 24 in Table 5 | 2 |
| Polycarbonate resin (Panlite K 1300 made by Teijin Limited.) | 2 |
| Tetrahydrofuran | 16 |

The thus prepared charge transporting layer coating liquid was coated on the aforementioned charge generating layer by a doctor blade and dried at 80° C. for 2 minutes and then at 105° C. for 5 minutes, so that a charge transporting layer with a thickness of about 20 μm was formed on the charge generating layer; thus, an electrophotographic photoconductor No. 1 according to the present invention was prepared.

The electrophotographic photoconductor No. 1 was charged negatively in the dark under application of −6 kV of corona charge for 20 seconds and then allowed to stand in the dark for 20 seconds without applying any charge thereto. At this moment, the surface potential $V_{po}$ (V) of the photoconductor was measured by a Paper Analyzer (Kawaguchi Electro Works, Model SP-428). The photoconductor was then illuminated by a tungsten lamp in such a manner that the illuminance on the illuminated surface of the photoconductor was 20 lux, and the exposure $E_{\frac{1}{2}}$ (lux.seconds) required to reduce the initial surface potential $V_{po}$ (V) to ½ the initial surface potential $V_{po}$ (V) was measured. The results showed that $V_{po}$ (V) = −1010 V and $E_{\frac{1}{2}}$ = 2.50·lux seconds.

EXAMPLES P-2 THROUGH P-27

Example P-1 was repeated except that the charge generating material and the aromatic diethyl compound working as the charge transporting material employed in Example P-1 were respectively replaced by the charge generating materials and the aromatic diethyl compounds as listed in Table 6, whereby electrophotographic photoconductors No. 2 through No. 27 according to the present invention were prepared.

TABLE 6
| Photo-Conductor | Charge Generating Material | Charge Transporting Material (Aromatic diethyl compound in Table 5) |
|---|---|---|
| No. 2 | CG-2  | No. 24 |
| No. 3 | CG-3 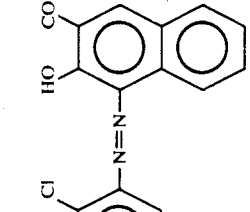 | No. 24 |
| No. 4 | CG-4 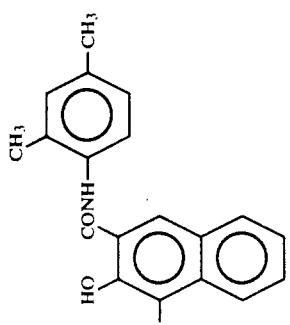 | No. 24 |

TABLE 6-continued
| Photo-Conductor | Charge Generating Material | Charge Transporting Material (Aromatic diethyl compound in Table 5) |
|---|---|---|
| No. 5 | 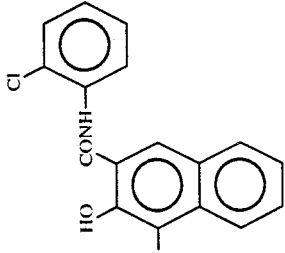<br>CG-5 | No. 24 |
| No. 6 | 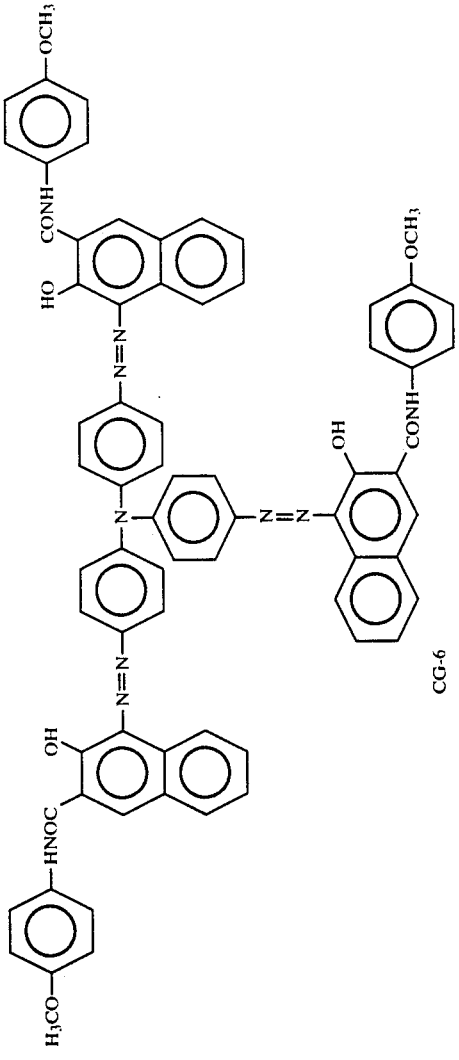<br>CG-6 | No. 24 |
| No. 7 | β-type copper phthalocyanine | No. 24 |

TABLE 6-continued

| Photo-Conductor | Charge Generating Material | Charge Transporting Material (Aromatic diethyl compound in Table 5) |
|---|---|---|
| No. 8 | (structure shown) | No. 22 |
| No. 9 | CG-7 | |
| No. 10 | CG-2 | 22 |
| No. 11 | CG-3 | 22 |
| No. 12 | CG-5 | 22 |
| No. 13 | CG-3 | 12 |
| No. 14 | CG-5 | 12 |
| No. 15 | CG-5 | 23 |
| No. 16 | CG-3 | 23 |
| No. 17 | CG-5 | 25 |
| No. 18 | CG-3 | 25 |
| No. 19 | CG-5 | 26 |
| No. 20 | CG-3 | 26 |
| No. 21 | CG-5 | 32 |
| No. 22 | CG-3 | 32 |
| No. 23 | CG-5 | 33 |
| No. 24 | CG-3 | 33 |
| No. 25 | CG-5 | 47 |
| No. 26 | CG-3 | 47 |
| No. 27 | CG-5 | 75 |
| | CG-3 | 75 |

EXAMPLE P-28

Selenium was vacuum-evaporated with a thickness of about 1.0 μm on an about 300 μm thick aluminum plate so that a charge generating layer was formed on the aluminum plate.

A charge transporting layer coating liquid was prepared by mixing and dispersing the following components:

|  | Parts by Weight |
|---|---|
| Aromatic diethyl compound No. 24 in Table 4 | 2 |
| Polyester resin (Polyester Adhesive 49000 made by Du Pont Co.) | 3 |
| Tetrahydrofuran | 45 |

The thus prepared charge transporting layer coating liquid was coated on the aforementioned selenium charge generating layer by a doctor blade, dried at room temperature and further dried under reduced pressure, so that a charge transporting layer about 10 μm thick was formed on the charge generating layer; thus, an electrophotographic photoconductor No. 28 according to the present invention was prepared.

EXAMPLE P-29

A perylene pigment C.I. Vat Red 23 (C.I. 71130) of the following formula was vacuum-evaporated with a thickness of about 0.3 μm on an about 300 μm thick aluminum plate so that a charge generating layer was formed on the aluminum plate:

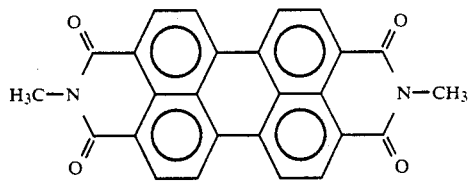

A charge transporting layer coating liquid was prepared by mixing and dispersing the following components:

|  | Parts by Weight |
|---|---|
| Aromatic diethyl compound No. 22 in Table 5 | 2 |
| Polyester resin (Polyester Adhesive 49000 made by Du Pont Co.) | 3 |
| Tetrahydrofuran | 45 |

The thus prepared charge transporting layer coating liquid was coated on the aforementioned charge generating layer by a doctor blade, dried at room temperature and further dried under reduced pressure, so that a charge transporting layer about 10 μm thick was formed on the charge generating layer; thus, an electrophotographic photoconductor No. 29 according to the present invention was prepared.

EXAMPLE P-30

One part by weight of Diane Blue (C.I. Pigment Blue 25, C.I. 21180) which was the same as that employed in Example P-1 was added to 158 parts by weight of tetrahydrofuran, and the mixture was ground and dispersed in a ball mill. To this mixture, 12 parts by weight of the aromatic diethyl compound No. 24 in Table 5 and 18 parts by weight of a polyester resin (Polyester Adhesive 49000 made by Du.Pont Co.) were added and mixed, whereby a photoconductive layer coating liquid was prepared.

The thus prepared photoconductive layer coating liquid was coated on an aluminum-evaporated polyester film by a doctor blade and dried at 100° C. for 30 minutes, so that a photoconductive layer with a thickness of about 16 μm was formed on the aluminum-evaporated polyester film, thus, an electrophotographic photoconductor No. 30 according to the present invention was prepared.

EXAMPLES P-31 THROUGH P-57

Example P-1 was repeated except that the charge generating material and the aromatic diethyl compound working as the charge transporting material employed in Example P-1 were respectively replaced by the charge generating materials and the aromatic diethyl compounds as listed in Table 7, whereby electrophotographic photoconductors No. 31 through No. 57 according to the present invention were prepared.

TABLE 7

| Photo-Conductor | Charge Generating Material | Charge Transporting Material (Aromatic diethyl compound in Table 5) |
|---|---|---|
| No. 31 | CG-1 | No. 269 |
| No. 32 | CG-2 | No. 269 |
| No. 33 | | No. 269 |

TABLE 7-continued

| Photo-Conductor | Charge Generating Material | Charge Transporting Material (Aromatic diethyl compound in Table 5) |
|---|---|---|
| No. 34 | CG-3 | No. 269 |
| No. 35 | CG-4 | No. 269 |
|  | CG-5 |  |

TABLE 7-continued

| Photo-Conductor | Charge Generating Material | Charge Transporting Material (Aromatic diethyl compound in Table 5) |
|---|---|---|
| No. 36 | (structure shown) | No. 269 |
| No. 37 | CG-6 | No. 269 |
| No. 38 | β-type copper phthalocyanine | No. 430 |
| No. 39 | CG-1 | No. 430 |
| No. 40 | CG-2 | No. 430 |
| No. 41 | CG-3 | No. 430 |
| No. 42 | CG-3 | No. 147 |
| No. 43 | CG-5 | No. 147 |
| No. 44 | CG-3 | No. 165 |
| No. 45 | CG-5 | No. 165 |
| No. 46 | CG-3 | No. 190 |
| No. 47 | CG-5 | No. 190 |

TABLE 7-continued

| Photo-Conductor | Charge Generating Material | Charge Transporting Material (Aromatic diethyl compound in Table 5) |
|---|---|---|
| No. 48 | CG-3 | No. 200 |
| No. 49 | CG-5 | No. 200 |
| No. 50 | CG-3 | No. 279 |
| No. 51 | CG-5 | No. 279 |
| No. 52 | CG-3 | No. 358 |
| No. 53 | CG-5 | No. 358 |
| No. 54 | CG-3 | No. 428 |
| No. 55 | CG-5 | No. 428 |
| No. 56 | CG-3 | No. 507 |
| No. 57 | CG-5 | No. 507 |

EXAMPLE 58

Example P-28 was repeated except that the charge transporting material employed in Example P-28 was replaced by aromatic diethyl compound No. 269 in Table 5, whereby an electrophotographic photoconductor No. 58 according to the present invention was prepared.

EXAMPLE 59

Example P-29 was repeated except that the charge transporting material employed in Example P-29 was replaced by aromatic diethyl compound No. 430 in Table 5, whereby an electrophotographic photoconductor No. 59 according to the present invention was prepared.

EXAMPLE 60

Example P-30 was repeated except that the charge transporting material employed in Example P-30 was replaced by aromatic diethyl compound No. 269 in Table 5, whereby an electrophotographic photoconductor No. 60 according to the present invention was prepared.

EXAMPLE P-61

The following components were mixed and dissolved, s that a charge transporting layer coating liquid was prepared:

|  | Parts by Weight |
|---|---|
| Aromatic diethyl compound No. 269 in Table 5 | 2 |
| Polycarbonate resin (Panlite K 1300 made by Teijin Limited.) | 2 |
| Tetrahydrofuran | 16 |

The thus prepared charge transporting layer coating liquid was coated by a doctor blade on the aluminum-evaporated surface of an aluminum-evaporated polyester base film, which served as an electroconductive support, so that a charge transporting layer was formed on the electroconductive support, with a thickness of about 20 μm when dried at room temperature.

Then the following components were ground and dispersed in a ball mill to prepare a dispersion:

|  | Parts by Weight |
|---|---|
| Bisazo Pigment (a charge generating pigment of the following formula (CG-5)) | 13.5 |
| Polyvinyl butyral (Trademark "XYHL" made by Union Carbide Plastic Co., Ltd.) | 5.4 |
| Tetrahydrofuran | 680 |
| Ethyl cellosolve | 1020 |

To the above dispersion, 1700 parts by weight of ethyl cellosolve were further added and the mixture was dispersed, whereby a charge generating layer coating liquid was prepared.

The thus prepared charge generating layer coating liquid was coated on the aforementioned charge transporting layer by spray coating and dried at 100° C. for 10 minutes, whereby a charge generating layer having a thickness of about 0.2 μm was formed on the charge transporting layer.

Then a methanol/n-buthanol solution of a polyaminde resin (Trademark "CM-8000" made by Toray Industries, Inc.) was coated on the charge generating layer by spray coating and dried at 120° C. for 30 minutes, whereby a protective layer having a thickness of about 0.5 μm was formed on the charge generating layer. Thus an electrophotographic photoconconductor No. 61 according to the present invention was prepared.

The thus prepared electrophotographic photoconductors No. 2 to No. 61 were charged negatively or positively in the dark under application of −6 kV or +6 kV of corona charge for 20 seconds and then allowed to stand in the dark for 20 seconds without applying any charge thereto. At this moment, the surface potential $V_{po}(V)$ of each photoconductor was measured by a Paper Analyzer (Kawaguchi Electro Works, Model SP-428). Each photoconductor was then illuminated by a tungsten lamp in such a manner that the illuminance on the illuminated surface of the photoconductor was 20 lux, so that the exposure $E_{\frac{1}{2}}$ (lux seconds) required to reduce the initial surface potential $V_{po}(V)$ to $\frac{1}{2}$ the initial surface potential $V_{po}(V)$ was measured.

The results are shown in in Table 8.

TABLE 8

| Photoconductors | $V_{po}$ (volt) | $E_{\frac{1}{2}}$ (lux · sec) |
|---|---|---|
| No. 1 | −1010 | 2.50 |
| No. 2 | −1250 | 2.04 |
| No. 3 | −1196 | 1.03 |
| No. 4 | −1320 | 3.11 |
| No. 5 | −1223 | 1.23 |
| No. 6 | −1015 | 1.87 |
| No. 7 | −982 | 2.10 |
| No. 8 | −1256 | 3.23 |
| No. 9 | −1125 | 2.98 |
| No. 10 | −1008 | 1.27 |
| No. 11 | −973 | 1.54 |
| No. 12 | −1440 | 1.31 |
| No. 13 | −1328 | 2.36 |
| No. 14 | −1412 | 1.24 |
| No. 15 | −1092 | 1.32 |
| No. 16 | −1349 | 1.19 |
| No. 17 | −995 | 1.21 |
| No. 18 | −1274 | 1.15 |
| No. 19 | −719 | 0.87 |
| No. 20 | −1292 | 1.16 |
| No. 21 | −1180 | 1.45 |
| No. 22 | −1047 | 1.20 |
| No. 23 | −707 | 1.06 |

TABLE 8-continued

| Photoconductors | $V_{po}$ (volt) | $E_{\frac{1}{2}}$ (lux · sec) |
| --- | --- | --- |
| No. 24 | −918 | 1.31 |
| No. 25 | −893 | 1.60 |
| No. 26 | −951 | 1.33 |
| No. 27 | −861 | 1.85 |
| No. 28 | −921 | 3.12 |
| No. 29 | −1181 | 3.45 |
| No. 30 | +1280 | 3.01 |
| No. 31 | −1012 | 2.80 |
| No. 32 | −1120 | 2.54 |
| No. 33 | −1236 | 1.21 |
| No. 34 | −1310 | 3.00 |
| No. 35 | −1330 | 1.53 |
| No. 36 | −1215 | 1.77 |
| No. 37 | −930 | 2.15 |
| No. 38 | −1121 | 3.10 |
| No. 39 | −1210 | 2.11 |
| No. 40 | −997 | 1.21 |
| No. 41 | −957 | 1.07 |
| No. 42 | −1310 | 3.11 |
| No. 43 | −1112 | 2.36 |
| No. 44 | −1120 | 2.01 |
| No. 45 | −960 | 1.96 |
| No. 46 | −1440 | 1.35 |
| No. 47 | −1240 | 1.58 |
| No. 48 | −1385 | 1.15 |
| No. 49 | −1190 | 1.20 |
| No. 50 | −1205 | 1.10 |
| No. 51 | −1010 | 1.16 |
| No. 52 | −1360 | 1.80 |
| No. 53 | −1290 | 1.60 |
| No. 54 | −1015 | 1.35 |
| No. 55 | −960 | 1.10 |
| No. 56 | −1112 | 1.18 |
| No. 57 | −998 | 1.06 |
| No. 58 | −862 | 3.15 |
| No. 59 | −914 | 2.98 |
| No. 60 | +1365 | 3.02 |
| No. 61 | +1218 | 1.61 |

Each of the above electrophotographic photoconductors No. 1 through No. 61 was incorporated in a commercially available electrophotographic copying machine and a latent electrostatic image was formed thereon by being exposed to a light image. The latent electrostatic image was developed with a dry type developer to a visible toner image, electrostatically transferred to a transfer sheet made of plain paper and fixed thereto. As a result, a clear transferred image was obtained by each of the photoconductors. When a liquid developer was employed instead of the dry type developer, clear transfer images were obtained likewise.

Of particular interest, in accordance with the present invention, are 1,4-divinylbenzene derivatives of the formula (I-3):

having 1 to 5 carbon atoms, an unsubstituted or substituted aryl group or a halogen.

Also, of particular interest are diethylbenzene derivatives having the formula (II-2):

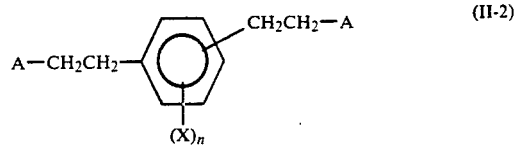

wherein A represents an N-substituted carbazolyl group, or

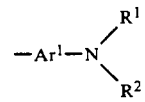

wherein $Ar^1$ represents an unsubstituted or substituted aromatic hydrocarbon group or a heterocyclic group, and $R^1$ and $R^2$ each represent an unsubstituted or substituted alkyl group, or an unsubstituted or substituted aryl group; X represents an alkyl group having 1 to 5 carbon atoms, an alkoxyl group having 1 to 5 carbon atoms or a halogen; and n is an integer of 0 to 2.

Within the general formula (II-2), however, the diethylbenzene derivatives of the formula (II-2a) are also of particular interest:

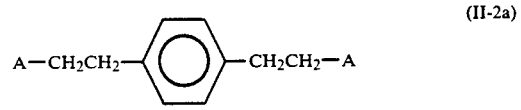

wherein A is:

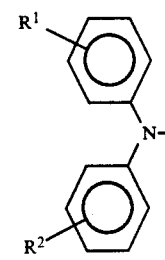

wherein R represents an alkyl group having 1 to 5 carbon atoms, a phenyl group, a p-$C_1$-$C_5$-alkylphenyl group or a p-$C_1$-$C_5$-alkoxyphenyl group. More particularly, R represents a methyl or an ethyl group.

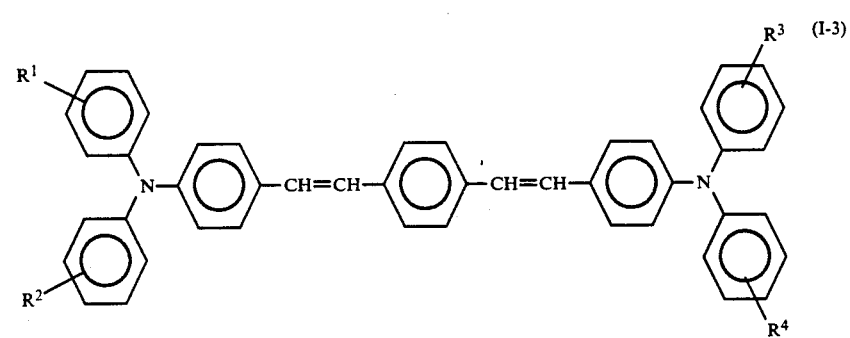

wherein $R^1$, $R^2$, $R^3$ and $R^4$ each represent an alkyl group having 1 to 5 carbon atoms, an alkoxyl group The present invention also provides diethylbenzene derivatives of the formula (II-3):

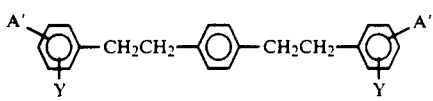

wherein Y is hydrogen, an alkyl group having 1 to 5 carbon atoms, and A' is:

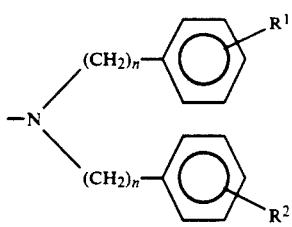

wherein $R^1$ and $R^2$ each represent hydrogen, an alkyl group having 1 to 5 carbon atoms, an alkoxy group having 1 to 5 carbon atoms, an unsubstituted or substituted aryl group, a halogen or a cyano group; and n is an integer of 0 to 1.

The present invention further provides diethylbenzene derivatives of the formula (II-3a):

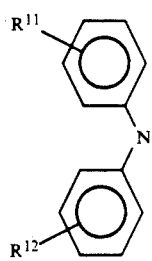

wherein $R^{11}$, $R^{12}$, $R^{13}$ and $R^{14}$ each represent hydrogen, an alkyl group having 1 to 5 carbon atoms, an alkoxyl group having 1 to 5 carbon atoms, an unsubstituted or substituted aryl group or a halogen.

Within the formula (II-3a), of particular interest are the compounds wherein $R^{11}$, $R^{12}$, $R^{13}$ and $R^{14}$ each represent a methyl group, a methoxy group, a phenyl group or chlorine.

Having described the present invention, it will be apparent to one skilled in the art that many changes and modifications can be made to the above-described embodiments without departing from the spirit and scope of the present invention.

What is claimed is:

1. Diethylbenzene derivatives having the formula:

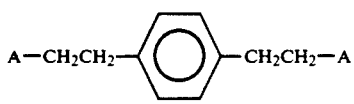

wherein A is:

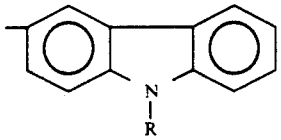

in which R represents an alkyl group having 1 to 5 carbon atoms, a phenyl group, a p-$C_1$-$C_5$-alkyl phenyl group or a p-$C_1$-$C_5$-alkoxyphenyl group.

2. The diethylbenzene derivatives as claimed in claim 1, wherein R represents a methyl group or an ethyl group.

3. The diethylbenzene derivatives as claimed in claim 1, wherein A is:

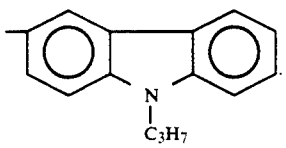

4. The diethylbenzene derivatives as claimed in claim 1, wherein A is:

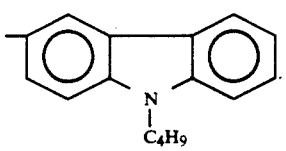

5. The diethylbenzene derivatives as claimed in claim 1, wherein A is:

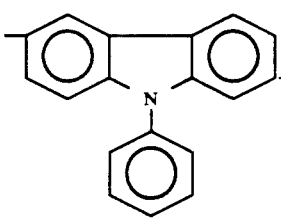

6. The diethylbenzene derivatives as claimed in claim 1, wherein A is:

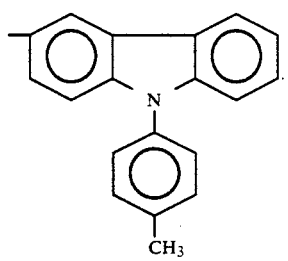
7. The diethylbenzene derivatives as claimed in claim 1, wherein A is:
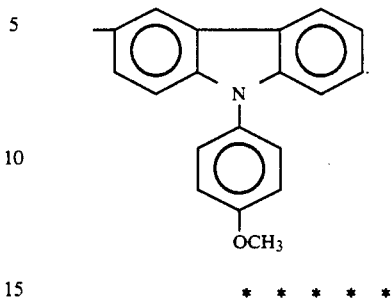
* * * * *

UNITED STATES PATENT AND TRADEMARK OFFICE
CERTIFICATE OF CORRECTION

PATENT NO. : 5,159,087
DATED : October 27, 1992
INVENTOR(S) : Tomoyuki Shimada, et al It is certified that error appears in the above-indentified patent and that said Letters Patent is hereby corrected as shown below:

Column 3, line 60, after "above" insert -- -- --;

Column 3, line 64, after "above" insert -- -- --;

Column 6, line 44, after "above" insert -- -- --'

Column 7, line 30, after "For example," insert --dioxane, tetrahydrofuran and N,N-dimethyl formamide, are preferred.--

Column 11, line 47, delete "-iyl" and insert therefor --diyl--;

Column 229, line 25, after "invention" insert --.--;

Column 251, line 28, delete "s" and insert therefor --so--;

Column 256, line 10, in Claim 1, delete "alkyl phenyl" and insert therefor --alkylphenyl--.

Signed and Sealed this

Sixth Day of September, 1994

Attest:

BRUCE LEHMAN

*Attesting Officer*    *Commissioner of Patents and Trademarks*